United States Patent [19]

Lange et al.

[11] Patent Number: 5,631,209
[45] Date of Patent: May 20, 1997

[54] HERBICIDAL GLUTARIMIDES

[75] Inventors: Barry C. Lange; John W. Ashmore; Jane Wissinger-Cornille, all of Lansdale; Colin M. Tice, Elkins Park, all of Pa.

[73] Assignee: Rohm and Haas Company, Philadelphia, Pa.

[21] Appl. No.: 470,197

[22] Filed: Jun. 6, 1995

Related U.S. Application Data

[62] Division of Ser. No. 323,292, Oct. 14, 1994, Pat. No. 5,502,027, which is a division of Ser. No. 129,483, Sep. 30, 1993, Pat. No. 5,393,735, which is a continuation of Ser. No. 563,780, Aug. 9, 1990, abandoned, which is a continuation-in-part of Ser. No. 401,329, Aug. 31, 1989, abandoned.

[51] Int. Cl.$^6$ .................... C07D 221/02; C07D 211/88; C07D 211/84; A01N 43/42; A01N 43/40
[52] U.S. Cl. .................................. 504/248; 546/220
[58] Field of Search .................... 504/248; 546/142, 546/220

[56] References Cited

U.S. PATENT DOCUMENTS

| | | | |
|---|---|---|---|
| 3,862,172 | 1/1975 | Collins | 540/485 |
| 3,903,078 | 9/1975 | Houter | 546/191 |
| 3,903,085 | 9/1975 | Woods | 544/166 |
| 3,992,389 | 11/1976 | Cavalla | 546/224 |
| 4,097,260 | 6/1978 | D'Amico | 504/247 |
| 4,110,105 | 8/1978 | Teach | 504/283 |
| 4,400,202 | 8/1983 | Teach | 504/248 |
| 4,595,408 | 6/1986 | Teach | 504/248 |
| 4,642,307 | 2/1987 | Aoyagi et al. | 514/252 |
| 5,223,018 | 6/1993 | Moser | 504/221 |

FOREIGN PATENT DOCUMENTS

| | | |
|---|---|---|
| 39184 | 10/1990 | European Pat. Off. |
| 253084 | 10/1988 | Japan. |
| 1237 | 1/1990 | Switzerland. |
| 3869 | 1/1990 | Switzerland. |

OTHER PUBLICATIONS

Modena et al., 2[(Arylamino)Carbonyl]benzeneacetic . . . , Farmaco 44, pp. 721–729 (1989).

Gootjes, J.; Nauta, W. Th., Rec. Trav. Chem., 1965, 84, 1183.

*Primary Examiner*—C. Warren Ivy
*Assistant Examiner*—Lyman H. Smith
*Attorney, Agent, or Firm*—Joseph F. Leightner

[57] ABSTRACT

This invention relates to glutarimide compounds exhibiting herbicidal activity having the structure

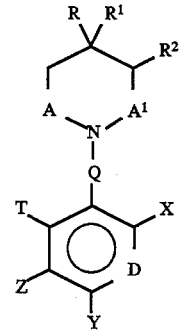

wherein A is carbonyl, thiocarbonyl or methylene, $A^1$ is carbonyl or methylene, Q is O or $(CH_2)_n$, where n is 0 or 1, D is CH or N and R, $R^1$, $R^2$, T, X, Y and Z are as defined within, compositions containing these compounds and methods of using these compounds as herbicides and algicides.

20 Claims, No Drawings

HERBICIDAL GLUTARIMIDES

STATUS OF RELATED APPLICATIONS

This application is a divisional application of U.S. Ser. No. 08/323,292 filed Oct. 14, 1994, now U.S. Pat. No. 5,502,027; which is a divisional application of U.S. Ser. No. 08/129,483 filed Sep. 30, 1993, now U.S. Pat. No. 5,393,735; which is a continuation of U.S. Ser. No. 07/563,780 filed Aug. 9, 1990, now abandoned; which is a continuation-in-part of Ser. No. 07/401,329 filed Aug. 31, 1989, now abandoned.

This invention relates to novel glutarimides which have activity as herbicides and algicides, to compositions which contain these compounds and to methods of use of these compounds.

BACKGROUND OF THE INVENTION

During the past years, there has been an intensified search for herbicides to control unwanted plants. U.S. Pat. No. 4,400,202 discloses N-(m-phenylglutarimido)ureas and N-(m-phenylsuccinimido)ureas and their use as herbicides. No other substitution on the phenyl ring is disclosed.

U.S. Pat. No. 4,595,408 discloses N-(m-amidophenyl) succinimides and N-(m-amidophenyl)glutarimides and their use as herbicides. No other substitution on the phenyl ring is disclosed.

There remains a need for additional herbicidal agents which are as effective or more effective than presently existing compounds.

SUMMARY OF THE INVENTION

The present invention is a new class of substituted cyclic imides of the formula

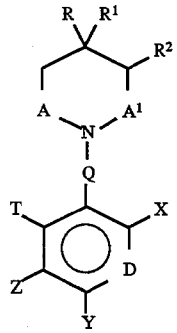

wherein

A is carbonyl (C=O), thiocarbonyl (C=S) or methylene ($CH_2$);

$A^1$ is carbonyl (C=O) or methylene ($CH_2$);

provided that when Z is hydrogen (H), A and $A^1$ are not both $CH_2$;

D is CH or, when X is hydrogen, nitrogen (N);

Q is methylene (($CH_2)_n$), where n is 0 or 1, or oxygen (O);

R is ($C_1$–$C_4$)alkyl, ($C_1$–$C_4$)haloalkyl containing from one to nine halo atoms, or phenyl;

$R^1$ is hydrogen or ($C_1$–$C_2$)alkyl; provided $R^1$ is hydrogen when X and Z are independently hydrogen or halogen and Y is halogen;

$R^2$ is hydrogen; or

R, $R^1$ and $R^2$ taken together form a fused phenyl ring;

X is hydrogen, cyano (CN) or halogen;

Y is hydrogen, halogen, cyano (CN), ($C_1$–$C_3$)alkylthio, halo($C_1$–$C_3$)alkylthio, ($C_1$–$C_3$)alkyl, halo($C_1$–$C_3$)alkyl, nitro, halo($C_1$–$C_3$)alkoxy or ($C_1$–$C_3$)alkoxy;

provided when Y is hydrogen, R is trifluoromethyl ($CF_3$), $R^1$ and $R^2$ are hydrogen and Z is not hydrogen;

T is hydrogen or fluorine; and

Z is hydrogen; hydroxy (OH); halogen; cyano; thiol (SH); alkylsulfonyloxy (—$OSO_2$alkyl); phenylsulfonyloxy (—$OSO_2$phenyl); alkyl; alkoxy; alkenyloxy; alkynyloxy; cycloalkoxy; cycloalkylalkoxy; phenylalkoxy; alkylthio; alkenylthio; alkynylthio; cycloalkylthio; cycloalkylalkylthio; phenylalkylthio; alkanoyloxy; alkanoylthio; alkoxycarbonylalkylthio; alkoxycarbonylalkoxy; alkoxycarbonyl(alkoxy)alkoxy; alkoxyalkoxy; (alkylthio)alkoxy; alkoxyalkylthio; alkylthioalkylthio; (phenylthio)alkoxy; phenoxyalkoxy; phenylthioalkylthio; phenoxyalkylthio; carboxyalkylthio; carboxyalkoxy; heterocyclyloxy; heterocyclylalkyloxy; carboxy; formyl; alkylcarbonyl; alkoxycarbonyl; (alkylthio)carbonyl; alkoxycarbonylalkoxycarbonyl; phenoxycarbonyl; alkoxyalkoxycarbonyl; alkenyloxycarbonyl; alkynyloxycarbonyl; cycloalkoxycarbonyl; cycloalkylalkoxycarbonyl; (alkenylthio)carbonyl; (alkynylthio)carbonyl; (cycloalkylthio)carbonyl; (cycloalkylalkylthio) carbonyl; heterocyclylcarbonyl; heterocyclylalkoxycarbonyl; heterocyclyloxycarbonyl; trialkylsilylalkoxycarbonyl; dialkoxyphosphonylalkoxycarbonyl (—C(=O)OalkylP(=O)(alkoxy)$_2$); dialkyliminooxycarbonyl (—C(=O)ON=C(alkyl)$_2$); alkyliminooxycarbonyl; alkyl(alkoxy)iminooxycarbonyl; alkyl(alkylthio)iminooxycarbonyl; phenylaminocarbonyl; aminocarbonyl; alkylaminocarbonyl; alkenylaminocarbonyl; alkynylaminocarbonyl; alkoxyaminocarbonyl; alkoxyalkyl; alkenyloxyalkyl; alkynyloxyalkyl; cycloalkoxyalkyl; cycloalkylalkoxyalkyl; alkanoyloxyalkyl; alkylthioalkyl; alkenylthioalkyl; alkynylthioalkyl; cycloalkylthioalkyl; cycloalkylalkylthioalkyl; (alkanoylthio)alkyl; phenoxyalkyl; phenylthioalkyl; alkoxycarbonylalkoxyalkyl; oximyl (—CH=NOH); alkyloximyl (—CH=NOalkyl); alkenyloximyl (—CH=NOalkenyl); alkynyloximyl (—CH=NOalkynyl); alkoxycarbonylalkyloximyl (—CH=NO(alkoxycarbonyl)alkyl); alkyl(alkoxy)oximyl (—C(alkoxy)=NOalkyl); alkenyl(alkoxy)oximyl (—C(alkoxy)=NOalkenyl); alkynyl(alkoxy)oximyl (—C(alkoxy)=NOalkynyl); alkoxycarbonylalkyl(alkoxy) oximyl (—C(alkoxy)=NO(alkoxycarbonyl)alkyl); alkyl(alkyl)oximyl (—C(alkyl)=NOalkyl); alkenyl(alkyl) oximyl (—C(alkyl)=NOalkenyl); alkynyl(alkyl)oximyl (—C(alkyl)=NOalkynyl); alkoxycarbonylalkyl(alkyl) oximyl (—C(alkyl)=NO(alkoxycarbonyl)alkyl); alkyl (alkylthio)oximyl (—C(alkylthio)=NOalkyl); alkenyl (alkylthio)oximyl (—C(alkylthio)=NOalkenyl); alkynyl (alkylthio)oximyl (—C(alkylthio)=NOalkynyl); alkoxycarbonylalkyl(alkylthio)oximyl (—C(alkylthio) =NO(alkoxycarbonyl)alkyl); heterocyclyl; alkylamino; alkenylamino; alkynylamino; or alkanoylamino;

provided Z is not hydrogen when X and Y are both bromine (Br) or chlorine (Cl) and D is CH; or Z and Y together form a 5- or 6-membered heterocyclic ring fused to the phenyl ring structure to form a bicyclic moiety having the structure

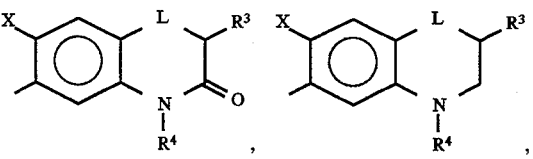

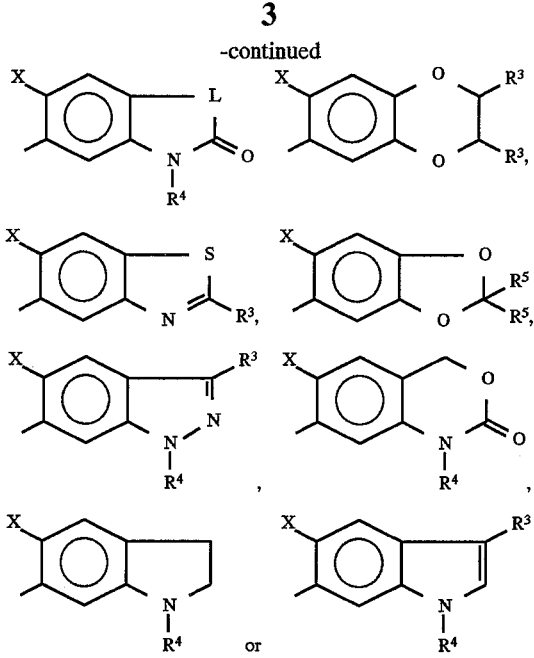

wherein

L is oxygen (O) or sulfur (S);

R³ is hydrogen or alkyl;

R⁴ is hydrogen; alkyl; alkenyl; alkynyl; alkoxyalkyl; alkenyloxyalkyl; alkynyloxyalkyl; cyanoalkyl; alkoxycarbonylalkyl; cycloalkyl; cycloalkylalkyl; phenylalkyl; alkylthioalkyl; alkenylthioalkyl; alkynylthioalkyl; heterocyclyl; heterocyclylalkyl; alkylaminoalkyl; alkylaminocarbonylalkyl; alkoxycarbonyl; or alkanoyl; and R⁵ is hydrogen, (C₁–C₃)alkyl or fluorine. Also included are the agronomically acceptable salts thereof.

Alkyl means straight and branched alkyl groups, for example (C₁–C₈)alkyl such as methyl, ethyl, n-propyl, isopropyl, n-butyl, isobutyl, s-butyl, 1-ethylpropyl or n-octyl. An alkyl portion of any one of the substituents listed above for Z is optionally substituted by one to five halogens to form groups such as trifluoromethyl, 1,1,1,2,2-pentafluoroethyl or (trifluoromethyl)methyl; optionally substituted by phenyl to form groups such as benzyl or phenethyl; or optionally substituted by cyano to form groups such as cyanomethyl, 2-cyanoethyl or 1-cyanoethyl. Cycloalkyl is, for example, cyclopropyl, cyclobutyl, cyclopentyl, cyclohexyl and includes cycloalkyl optionally substituted by (C₁–C₄)alkyl, for example 2-methylcyclopropyl, or halo, for example 2,2-dichlorocyclopropyl. Phenyl is optionally substituted with one or two substituents such as (C₁–C₃)alkyl, halogen, (C₁–C₃)alkoxy or trifluoromethyl. Haloalkyl for R is, for example, fluoromethyl, difluoromethyl, trifluoromethyl, or pentafluoroethyl.

Heterocyclyl means a three to six membered heterocyclic ring containing one, two or three heteroatoms such as oxygen, nitrogen or sulfur and includes saturated and unsaturated rings, for example tetrahydrofuryl, furyl, epoxy, pyridyl, piperidyl, dioxolanyl, isoxazolidinyl, triazolyl, thienyl, thiazolyl or piperazyl, optionally substituted by one to three (C₁–C₆)alkyl groups for example, 5,5-dimethyloxazolinyl.

Halogen means fluorine, chlorine, bromine and iodine.

When listed for Y and Z, thio means thio (—S—). When not bonded to carbonyl, thio also includes sulfinyl (—SO—) and sulfonyl (—SO₂—).

Substituted amino groups such as alkylamino include mono- and di-substituted groups for example monoalkylamino and dialkylamino.

Oximes are in either the syn or anti configuration or are mixtures thereof.

Agronomically acceptable salts include those known in the art, for example, metal salts such as sodium, potassium, calcium and magnesium, ammonium salts such as isopropylammonium and trialkylsulfonium salts such as trimethylsulfonium.

Alkoxy is, for example, (C₁–C₆)alkoxy such as methoxy, ethoxy, n-propyloxy, isopropyloxy, n-butyloxy, isobutyloxy, or s-butyloxy. Alkenyloxy is, for example, (C₃–C₆) alkenyloxy such as allyloxy, 2-chloroallyloxy or 3,3-dichloroallyloxy. Alkynyloxy is, for example, (C₃–C₆) alkynyloxy such as propargyloxy, 1-methylpropargyloxy, 1-(3-butynyl)oxy or 1-(2-butynyl)oxy. Phenylalkoxy is, for example, phenyl(C₁–C₆)alkoxy such as phenylmethoxy. Alkylthio is, for example, (C₁–C₆)alkylthio such as methylthio, ethylthio, propylthio, butylthio. Alkenylthio is, for example, (C₃–C₆)alkenylthio. Alkynylthio is, for example, (C₃–C₆)alkynylthio. Phenylalkylthio is, for example, phenyl(C₁–C₆)alkylthio. Alkanoyloxy is, for example, (C₁–C₆)alkanoyloxy. Alkanoylthio is, for example, (C₁–C₆)alkanoylthio such as acetylthio. Alkoxycarbonylalkylthio is, for example, (C₁–C₆)alkoxycarbonyl(C₁–C₄) alkylthio such as methoxycarbonylmethylthio or isopropyloxycarbonylmethylthio. Alkoxycarbonylalkoxy is, for example, (C₁–C₆)alkoxycarbonyl(C₁–C₄)alkoxy such as methoxycarbonylmethoxy. Alkoxycarbonyl(alkoxy)alkoxy is, for example, (C₁–C₆)alkoxycarbonyl((C₁–C₆)alkoxy) (C₁–C₆)alkoxy such as methoxycarbonyl(methoxy) methoxy. Alkoxyalkoxy is, for example, (C₁–C₆)alkoxy (C₁–C₆)alkoxy such as methoxymethoxy or 2-methoxyethoxy. (Alkylthio)alkoxy is, for example, ((C₁–C₆)alkylthio)(C₁–C₆)alkoxy. Alkoxyalkylthio is, for example, (C₁–C₆)alkoxy(C₁–C₆)alkylthio. Alkylthioalkylthio is, for example, (C₁–C₆)alkylthio(C₁–C₆)alkylthio. (Phenylthio)alkoxy is, for example, (phenylthio)(C₁–C₆) alkoxy such as (phenylthio)methoxy. Phenoxyalkoxy is, for example, phenoxy(C₁–C₆)alkoxy. Phenylthioalkylthio is, for example, phenylthio(C₁–C₆)alkylthio. Phenoxyalkylthio is, for example, phenoxy(C₁–C₆)alkylthio. Carboxyalkylthio is, for example, carboxy(C₁–C₆)alkylthio. Carboxyalkoxy is, for example, carboxy(C₁–C₆)alkoxy such as carboxymethoxy. Alkylcarbonyl is, for example (C₁–C₆) alkylcarbonyl such as methylcarbonyl, i.e. acetyl. Alkoxycarbonyl is, for example, (C₁–C₆)alkoxycarbonyl such as methoxycarbonyl, ethoxycarbonyl, n-propyloxycarbonyl, isopropyloxycarbonyl, 1-cyanoethoxycarbonyl, isobutyloxycarbonyl or s-butyloxycarbonyl. (Alkylthio)carbonyl is, for example, ((C₁–C₆)alkylthio)carbonyl such as (ethylthio)carbonyl or (isopropylthio)carbonyl. Alkoxycarbonylalkoxycarbonyl is, for example, (C₁–C₆)alkoxycarbonyl(C₁–C₆) alkoxycarbonyl such as methoxycarbonyl(methyl) methoxycarbonyl or ethoxycarbonyl-methoxycarbonyl. Alkoxyalkoxycarbonyl is, for example, (C₁–C₆)alkoxy (C₁–C₆)alkoxycarbonyl such as (2-methoxy)ethoxycarbonyl or (2-methoxy-1-methyl)ethoxycarbonyl. Alkenyloxycarbonyl is, for example, (C₃–C₆)alkenyloxycarbonyl. Alkynyloxycarbonyl is, for example, (C₃–C₆)alkynyloxycarbonyl such as propargyloxycarbonyl, 3-iodopropargyloxycarbonyl, 1-methylpropargyloxycarbonyl or 3-butynyloxycarbonyl. Cycloalkoxycarbonyl is, for example, (C₃–C₆) cycloalkoxycarbonyl such as cyclobutyloxycarbonyl, cyclopentyloxycarbonyl or cyclohexyloxycarbonyl. Cycloalkylalkoxycarbonyl is, for example, (C₃–C₆)cycloalkyl(C₁–C₆) alkoxycarbonyl. (Alkenylthio)carbonyl is, for example, ((C₃–C₆)alkenylthio)carbonyl. (Alkynylthio)carbonyl is, for example, ((C$_3$–C$_6$)alkynylthio)carbonyl. (Cycloalkylthio) carbonyl is, for example, ((C$_3$–C$_6$)cycloalkylthio)carbonyl. (Cycloalkylalkylthio)carbonyl is, for example, ((C$_3$–C$_6$) cycloalkyl(C$_1$–C$_6$)alkylthio)carbonyl. Heterocyclylalkoxycarbonyl is heterocyclyl(C$_1$–C$_6$)alkoxycarbonyl. Heterocyclyloxycarbonyl is, for example, 3-tetrahydrofuryloxycarbonyl. Trialkylsilylalkoxycarbonyl is, for example, tri(C$_1$–C$_6$)alkylsilyl(C$_1$–C$_6$)alkoxycarbonyl such as trimethylsilylmethoxycarbonyl. Dialkoxyphosphonylalkoxycarbonyl is, for example, di(C$_1$–C$_6$) alkoxyphosphonyl(C$_1$–C$_6$)alkoxycarbonyl such as diethoxyphosphonylmethoxycarbonyl. Dialkyliminooxycarbonyl is, for example, di(C$_1$–C$_6$)alkyliminooxycarbonyl such as dimethyliminooxycarbonyl. Alkyliminooxycarbonyl is, for example, (C$_1$–C$_6$)alkyliminooxycarbonyl. Alkyl(alkoxy)iminooxycarbonyl is, for example, (C$_1$–C$_6$)alkyl((C$_1$–C$_6$) alkoxy)iminooxycarbonyl. Alkyl(alkylthio) iminooxycarbonyl is, for example, (C$_1$–C$_6$)alkyl((C$_1$–C$_6$) alkylthio)iminooxycarbonyl. Alkylaminocarbonyl is, for example, mono(C$_1$–C$_6$)alkylaminocarbonyl such as isopropylaminocarbonyl or di(C$_1$–C$_6$)alkylaminocarbonyl. Alkenylaminocarbonyl is, for example, mono(C$_3$–C$_6$) alkenylaminocarbonyl. Alkynylaminocarbonyl is, for example, mono(C$_3$–C$_6$)alkynylaminocarbonyl such as propargylaminocarbonyl. Alkoxyaminocarbonyl is, for example, mono(C$_1$–C$_6$)alkoxyaminocarbonyl such as methoxyaminocarbonyl. Alkoxyalkyl is, for example, (C$_1$–C$_6$) alkoxy(C$_1$–C$_6$)alkyl such as methoxymethyl, ethoxymethyl or isopropyloxymethyl. Alkenyloxyalkyl is, for example, (C$_3$–C$_6$)alkenyloxy(C$_1$–C$_6$)alkyl. Alkynyloxyalkyl is, for example, (C$_3$–C$_6$)alkynyloxy(C$_1$–C$_6$)alkyl such as propargyloxymethyl or 1-methylpropargyloxymethyl. Cycloalkoxyalkyl is, for example, (C$_3$–C$_6$)cycloalkoxy (C$_1$–C$_6$)alkyl. Cycloalkylalkoxyalkyl is, for example, (C$_3$–C$_6$)cycloalkyl(C$_1$–C$_6$)alkoxy(C$_1$–C$_6$)alkyl. Alkanoyloxyalkyl is, for example, (C$_1$–C$_6$)alkanoyloxy(C$_1$–C$_6$)alkyl such as acetoxymethyl. Alkylthioalkyl is, for example, (C$_1$–C$_6$)alkylthio(C$_1$–C$_6$)alkyl such as methylthiomethyl, isopropylthiomethyl or ethylthiomethyl. Alkenylthioalkyl is, for example, (C$_3$–C$_6$)alkenylthio(C$_1$–C$_6$)alkyl. Alkynylthioalkyl is, for example, (C$_3$–C$_6$)alkynylthio(C$_1$–C$_6$)alkyl. Cycloalkylthioalkyl is, for example, (C$_3$–C$_6$)cycloalkylthio (C$_1$–C$_6$)alkyl. Cycloalkylalkylthioalkyl is, for example, (C$_3$–C$_6$)cycloalkyl(C$_1$–C$_6$)alkylthio(C$_1$–C$_6$)alkyl. (Alkanoylthio)alkyl is, for example, ((C$_1$–C$_6$)alkanoylthio) (C$_1$–C$_6$)alkyl. Phenoxyalkyl is, for example, phenoxy (C$_1$–C$_6$)alkyl such as phenoxymethyl. Phenylthioalkyl is, for example, phenylthio(C$_1$–C$_6$)alkyl such as phenylthiomethyl. Alkoxycarbonylalkoxyalkyl is, for example, (C$_1$–C$_6$) alkoxycarbonyl(C$_1$–C$_6$)alkoxy(C$_1$–C$_6$)alkyl such as ethoxycarbonyl(methyl)methoxymethyl. Alkylaminoalkyl is, for example, di(C$_1$–C$_6$)alkylamino(C$_1$–C$_6$)alkyl such as dimethylaminoethyl. Alkenyl is, for example, (C$_3$–C$_6$) alkenyl such as allyl. Alkynyl is, for example, (C$_3$–C$_6$) alkynyl such as propargyl or 1-methylpropargyl. Alkyloximyl is, for example, (C$_1$–C$_6$)alkyloximyl such as methyloximyl, isopropyloximyl or t-butyloximyl. Alkenyloximyl is, for example, (C$_3$–C$_6$)alkenyloximyl such as allyloximyl. Alkynyloximyl is, for example, (C$_3$–C$_6$) alkynyloximyl such as propargyloximyl. Alkoxycarbonylalkyloximyl is, for example, (C$_1$–C$_6$)alkoxycarbonyl(C$_1$–C$_6$) alkyloximyl. Phenylalkyloximyl is, for example, phenyl (C$_1$–C$_6$)alkyloximyl such as benzyloximyl. Alkyl(alkyl) oximyl is, for example, (C$_1$–C$_6$)alkyl((C$_1$–C$_6$)alkyl)oximyl. Alkenyl(alkyl)oximyl is, for example, (C$_3$–C$_6$)alkenyl( (C$_1$–C$_6$)alkyl)oximyl. Alkynyl(alkyl)oximyl is, for example (C$_3$–C$_6$)alkynyl((C$_1$–C$_6$)alkyl)oximyl. Alkoxycarbonylalkyl (alkyl)oximyl is, for example, (C$_1$–C$_6$)alkoxycarbonyl (C$_1$–C$_6$)alkyl((C$_1$–C$_6$)alkyl)oximyl. Alkyl(alkoxy)oximyl is, for example, (C$_1$–C$_6$)alkyl((C$_1$–C$_6$)alkoxy)oximyl. Alkenyl(alkoxy)oximyl is, for example, (C$_3$–C$_6$)alkenyl( (C$_1$–C$_6$)alkoxy)oximyl. Alkynyl(alkoxy)oximyl is, for example, (C$_3$–C$_6$)alkynyl((C$_1$–C$_6$)alkoxy)oximyl. Alkoxycarbonylalkyl(alkoxy)oximyl is, for example, (C$_1$–C$_6$)alkoxycarbonyl(C$_1$–C$_6$)alkyl((C$_1$–C$_6$)alkoxy) oximyl. Alkyl(alkylthio)oximyl is, for example, (C$_1$–C$_6$) alkyl((C$_1$–C$_6$)alkylthio)oximyl. Alkenyl(alkylthio)oximyl is, for example, (C$_3$–C$_6$)alkenyl((C$_1$–C$_6$)alkylthio)oximyl. Alkynyl(alkylthio)oximyl is, for example, (C$_3$–C$_6$)alkenyl( (C$_1$–C$_6$)alkylthio)oximyl. Alkoxycarbonylalkyl(alkylthio) oximyl is, for example, (C$_1$–C$_6$)alkoxycarbonyl(C$_1$–C$_6$) alkyl((C$_1$–C$_6$)alkylthio)oximyl. Alkylamino is, for example, mono(C$_1$–C$_6$)alkylamino or di(C$_1$–C$_6$)alkylamino. Alkenylamino is, for example, mono(C$_3$–C$_6$)alkenylamino or di(C$_3$–C$_6$)alkenylamino. Alkynylamino is, for example, mono(C$_3$–C$_6$)alkynylamino. Alkanoylamino is, for example, mono(C$_1$–C$_6$)alkanoylamino such as acetamido. Alkoxycarbonylalkyl is, for example, (C$_1$–C$_6$)alkoxycarbonyl(C$_1$–C$_6$) alkyl such as isopropyloxycarbonylmethyl. Cyanoalkyl is, for example, cyano(C$_1$–C$_6$)alkyl such as cyanomethyl or 1-cyanoethyl. Phenylalkyl is, for example, phenyl(C$_1$–C$_6$) alkyl such as benzyl. Heterocyclylalkyl is, for example, heterocyclyl(C$_1$–C$_6$)alkyl such as epoxymethyl or 2-tetrahydrofuranylmethyl. Heterocyclylcarbonyl is, for example, isoxazolidinylcarbonyl. Heterocyclylalkoxy is, for example, heterocyclyl(C$_1$–C$_6$)alkoxy such as epoxymethoxy, 2-pyridylmethoxy or 2-tetrahydrofuranylmethoxy. Heterocyclyloxy is, for example, 3-tetrahydrofuranyloxy.

In a preferred embodiment of the invention are compounds of the formula

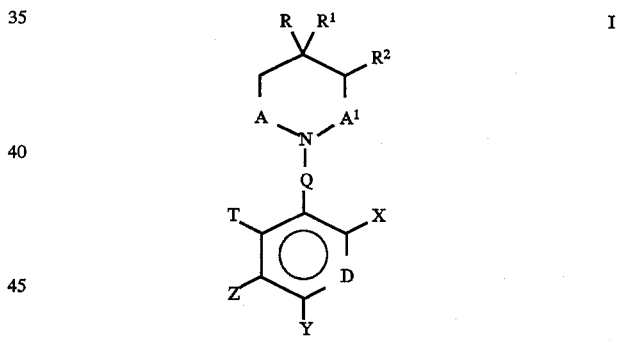

wherein
A is C=O, C=S or CH$_2$;
A$^1$ is C=O or CH$_2$;
provided when Z is hydrogen, A and A$^1$ are not both CH$_2$;
D is CH or, when X is H, N;
Q is (CH$_2$)$_n$, where n is 0 or 1, or oxygen;
R is (C$_1$–C$_4$)alkyl, (C$_1$–C$_4$)haloalkyl or phenyl;
R$^1$ is H or (C$_1$–C$_2$)alkyl, provided R$^1$ is H when X and Z are independently hydrogen or halogen and Y is halogen;
R$^2$ is H or, together with R and R$^1$, fused phenyl;
X is H, Cl, Br, CN or F;
Y is H, Cl, Br, F, I, CH$_3$, SCH$_3$, nitro, or OCH$_3$;
provided when Y is hydrogen, R is trifluoromethyl, R$^1$ and R$^2$ are hydrogen and Z is not hydrogen;
T is H or F;
Z is H; OH; halogen; CN; SH; (C$_1$–C$_6$)alkyl; (C$_1$–C$_6$) haloalkyl; —OSO$_2$(C$_1$–C$_6$)alkyl; —OSO$_2$phenyl; carboxy; formyl; phenoxycarbonyl; (C$_1$–C$_6$)alkoxy; (C$_3$–C$_6$) alkenyloxy; (C$_3$–C$_6$)alkynyloxy; cyano(C$_1$–C$_6$)alkoxy; phenyl(C$_1$–C$_6$)alkoxy; (C$_1$–C$_6$)alkylthio; (C$_1$–C$_6$)

alkanoyloxy; $(C_1-C_6)$alkanoylthio; $(C_1-C_6)$alkoxycarbonyl$(C_1-C_4)$alkylthio; $(C_1-C_6)$alkoxycarbonyl$(C_1-C_4)$alkoxy; $(C_1-C_6)$alkoxycarbonyl$((C_1-C_6)$alkoxy)$(C_1-C_6)$alkoxy; $(C_1-C_6)$alkoxy$(C_1-C_6)$alkoxy; (phenylthio)$(C_1-C_6)$alkoxy; carboxy$(C_1-C_6)$alkoxy; heterocyclyloxy; heterocyclyl $(C_1-C_6)$alkoxy; $(C_1-C_6)$alkylcarbonyl; $(C_1-C_6)$alkoxycarbonyl; $((C_1-C_6)$alkylthio)carbonyl; $(C_1-C_6)$alkoxycarbonyl$(C_1-C_6)$alkoxycarbonyl; $(C_1-C_6)$alkoxy$(C_1-C_6)$alkoxycarbonyl; cyano$(C_1-C_6)$alkoxycarbonyl; $(C_3-C_6)$alkenyloxycarbonyl; $(C_3-C_6)$alkynyloxycarbonyl; halo$(C_3-C_6)$alkenyloxycarbonyl; $(C_3-C_6)$cycloalkoxycarbonyl; heterocyclylcarbonyl; heterocyclyloxycarbonyl; tri$(C_1-C_6)$alkylsilyl$(C_1-C_6)$alkoxycarbonyl; di$(C_1-C_6)$alkoxyphosphonyl$(C_1-C_6)$alkoxycarbonyl; di$(C_1-C_6)$alkyliminooxycarbonyl; mono$(C_1-C_6)$alkylaminocarbonyl; mono$(C_3-C_6)$alkynylaminocarbonyl; phenylaminocarbonyl; mono$(C_1-C_6)$alkoxyaminocarbonyl; $(C_1-C_6)$alkoxy$(C_1-C_6)$alkyl; $(C_3-C_6)$alkenyloxy$(C_1-C_6)$alkyl; $(C_3-C_6)$alkynyloxy$(C_1-C_6)$alkyl; $(C_1-C_6)$alkanoyloxy$(C_1-C_6)$alkyl; $(C_1-C_6)$alkylthio$(C_1-C_6)$alkyl; phenoxy$(C_1-C_6)$alkyl; phenylthio$(C_1-C_6)$alkyl; $(C_1-C_6)$alkoxycarbonyl$(C_1-C_6)$alkoxy$(C_1-C_6)$alkyl; $(C_1-C_6)$alkyloximyl; $(C_3-C_6)$alkenyloximyl; $(C_3-C_6)$alkynyloximyl; phenyl$(C_1-C_6)$alkyloximyl; heterocyclyl; mono$(C_1-C_6)$alkanoylamino; or Z and Y together form a 5- or 6-membered heterocyclic ring fused to the phenyl ring structure to form a bicyclic moiety having the structure

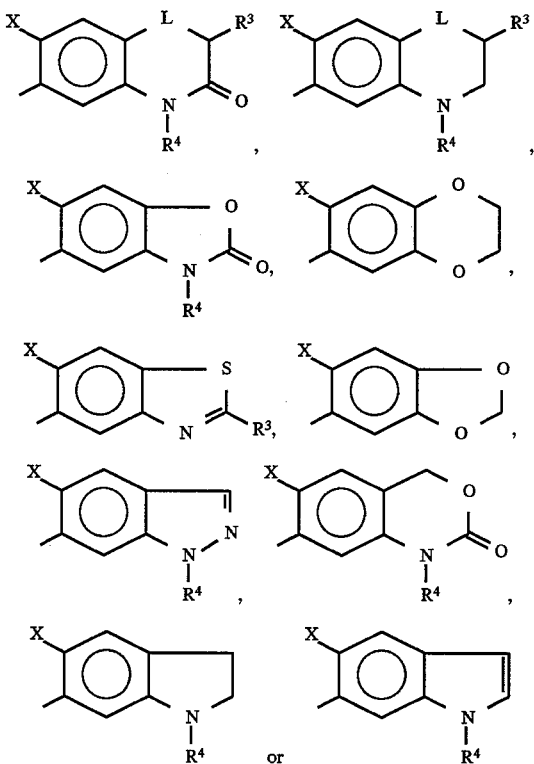

wherein

L is oxygen or sulfur;

$R^3$ is hydrogen or $(C_1-C_3)$alkyl; and $R^4$ is hydrogen; $(C_1-C_8)$alkyl; $(C_3-C_6)$alkenyl; $(C_3-C_6)$alkynyl; $(C_1-C_6)$alkoxy$(C_1-C_6)$alkyl; $(C_3-C_6)$cycloalkyl; $(C_3-C_6)$cycloalkyl$(C_1-C_6)$alkyl; $(C_1-C_6)$alkylthio$(C_1-C_6)$alkyl; phenyl$(C_1-C_6)$alkyl; cyano$(C_1-C_6)$alkyl; $(C_1-C_6)$alkoxycarbonyl$(C_1-C_6)$alkyl; $(C_1-C_6)$alkoxycarbonyl; heterocyclyl; heterocyclyl$(C_1-C_6)$alkyl; di$(C_1-C_6)$alkylamino$(C_1-C_6)$alkyl; di$(C_1-C_6)$alkylaminocarbonyl$(C_1-C_6)$alkyl; or $(C_1-C_6)$alkanoyl.

In one class of the preferred embodiment of the invention are ether and thioether glutarimides of Formula I wherein A is C=O or $CH_2$;

$A^1$ is C=O or $CH_2$;

D is CH or, when X is H, N;

Q is $(CH_2)_n$, where n is 0 or 1;

R is $(C_1-C_4)$alkyl, $(C_1-C_4)$haloalkyl or phenyl;

$R^1$ is H or $(C_1-C_2)$alkyl;

$R^2$ is H or, together with R and $R^1$, fused phenyl;

X is H, Cl, Br or F;

Y is H, Cl, Br, F or $CH_3$;

T is H or F; and

Z is $(C_1-C_6)$alkoxy; $(C_3-C_6)$alkenyloxy; $(C_3-C_6)$alkynyloxy; phenyl$(C_1-C_6)$alkoxy; $(C_1-C_6)$alkylthio; $(C_1-C_6)$alkanoyloxy; $(C_1-C_6)$alkanoylthio; $(C_1-C_6)$alkoxycarbonyl$(C_1-C_4)$alkylthio; $(C_1-C_6)$alkoxycarbonyl$(C_1-C_4)$alkoxy; cyano$(C_1-C_6)$alkoxy; $(C_1-C_6)$alkoxy$(C_1-C_6)$alkoxy; (phenylthio)$(C_1-C_6)$alkoxy; carboxy$(C_1-C_6)$alkoxy; heterocyclyloxy; heterocyclyl$(C_1-C_6)$alkoxy; $(C_3-C_6)$cycloalkoxy; $(C_3-C_6)$cycloalkyl$(C_1-C_6)$alkoxy; or $(C_1-C_6)$alkoxycarbonyl$[(C_1-C_6)$alkoxy]$(C_1-C_6)$alkoxy.

Preferred compounds of these ether and thioether glutarimides are compounds of Formula I wherein A and $A^1$ are C=O; D is CH; Q is $(CH_2)_n$; n is 0; R is $CH_3$, $CHF_2$ or $CF_3$; $R^1$ is H; $R^2$ is H; X is Cl or F; Y is Br, F, or Cl; T is H; and Z is $(C_1-C_6)$alkoxy, $(C_3-C_6)$alkenyloxy, $(C_3-C_6)$alkynyloxy, $(C_3-C_6)$cycloalkoxy, $(C_3-C_6)$cycloalkyl $(C_1-C_6)$alkoxy or $(C_1-C_6)$alkyloxy$(C_1-C_6)$alkyloxy.

More preferably when R is $CF_3$, $R^1$ and $R^2$ are hydrogen, X is fluoro, and Y is chloro, Z is allyloxy, isopropyloxy, s-butyloxy, propargyloxy, 1-methylpropargyloxy, cyclopentyloxy, cyclopropylmethoxy, 3-tetrahydrofuranyloxy, or methoxymethoxy.

More preferably when R is $CHF_2$, $R^1$ and $R^2$ are hydrogen, X is fluoro and Y is chloro, Z is propargyloxy.

More preferably when R is $CF_3$, $R^1$ and $R^2$ are hydrogen, X is fluoro, and Y is bromo, X is propargyloxy.

In a second class of the preferred embodiment of the invention are ester glutarimides of Formula I wherein A is C=O or $CH_2$;

$A^1$ is C=O or $CH_2$;

D is CH or, when X is H, N;

Q is $(CH_2)_n$, where n is 0 or 1;

R is $(C_1-C_4)$alkyl, $(C_1-C_4)$haloalkyl or phenyl;

$R^1$ is H or $(C_1-C_2)$alkyl;

$R^2$ is H or, together with R and $R^1$, fused phenyl;

X is H, Cl, Br or F;

Y is H, Cl, Br, F or $CH_3$;

T is H or F;

Z is carboxy; formyl; $(C_1-C_6)$alkoxycarbonyl; $(C_1-C_6)$alkoxycarbonyl$(C_1-C_6)$alkoxycarbonyl; cyano$(C_1-C_6)$alkoxycarbonyl; $(C_1-C_6)$alkoxy$(C_1-C_6)$alkoxycarbonyl; $((C_1-C_6)$alkylthio)carbonyl; $(C_1-C_6)$alkylcarbonyl; $(C_3-C_6)$alkenyloxycarbonyl; halo$(C_3-C_6)$alkynyloxycarbonyl; $(C_3-C_6)$alkynyloxycarbonyl; $(C_3-C_6)$cycloalkoxycarbonyl; heterocyclyloxycarbonyl; tri$(C_1-C_6)$alkylsilyl$(C_1-C_6)$alkoxycarbonyl; di$(C_1-C_6)$alkoxyphosphonyl$(C_1-C_6)$alkoxycarbonyl; di$(C_1-C_6)$alkyliminooxycarbonyl; monoalkylaminocarbonyl; mono$(C_1-C_6)$alkoxyaminocarbonyl; mono$(C_3-C_6)$alkynylaminocarbonyl; or phenylaminocarbonyl.

Preferred compounds of these ester glutarimides are compounds wherein A and $A^1$ are C=O; D is CH; Q is $(CH_2)_n$; n is 0; R is $CH_3$, $CHF_2$ or $CF_3$; $R^1$ is H; $R^2$ is H; X is Cl or F; Y is Br, F, or Cl; T is H; and Z is $CO_2$ H, $(C_1-C_6)$ alkoxycarbonyl, $(C_3-C_6)$cycloalkoxycarbonyl, $(C_3-C_6)$alkenyloxycarbonyl or $(C_3-C_6)$alkynyloxycarbonyl.

More preferably when R is $CF_3$, $R^1$ and $R^2$ are hydrogen, X is fluoro, and Y is chloro, Z is carboxy, methoxycarbonyl, n-propyloxycarbonyl, isopropyloxycarbonyl, s-butyloxycarbonyl, cyclobutyloxycarbonyl or ethoxycarbonyl.

More preferably when R is $CF_3$, $R^1$ and $R^2$ are hydrogen, X is fluoro, and Y is bromo, Z is isopropyloxycarbonyl.

More preferably when R is $CHF_2$, $R^1$ and $R^2$ are hydrogen, X is fluoro, and Y is chloro, Z is isopropyloxycarbonyl.

More preferably when R is $CH_3$, $R^1$ and $R^2$ are hydrogen, X is fluoro, and Y is chloro, Z is isopropyloxycarbonyl.

In a third class of the preferred embodiment of the invention are alkyl and oximyl glutarimides of Formula I wherein A is C=O or $CH_2$;
$A^1$ is C=O or $CH_2$;
D is CH or, when X is H, N;
Q is $(CH_2)_n$, where n is 0 or 1;
R is $(C_1-C_4)$alkyl, $(C_1-C_4)$haloalkyl or phenyl;
$R^1$ is H or $(C_1-C_2)$alkyl;
$R^2$ is H or, together with R and $R^1$, fused phenyl;
X is H, Cl, Br or F;
Y is H, Cl, Br, F or $CH_3$;
T is H or F;
Z is $(C_1-C_6)$alkyl; $(C_1-C_6)$alkoxy$(C_1-C_6)$alkyl; $(C_3-C_6)$alkenyloxy$(C_1-C_6)$alkyl; $(C_3-C_6)$alkynyloxy$(C_1-C_6)$alkyl; $(C_1-C_6)$alkanoyloxy$(C_1-C_6)$alkyl; $((C_1-C_6)$alkylthio)$(C_1-C_6)$alkyl; phenoxy$(C_1-C_6)$alkyl; phenylthio$(C_1-C_6)$alkyl; $(C_1-C_6)$alkoxycarbonyl$(C_1-C_6)$alkoxy$(C_1-C_6)$alkyl; $(C_1-C_6)$alkyloximyl; $(C_3-C_6)$alkenyloximyl; $(C_3-C_6)$alkynyloximyl; or phenyl$(C_1-C_6)$alkyloximyl.

Preferred compounds of this class of alkyl and oximyl glutarimides are compounds wherein A and $A^1$ are C=O; D is CH; Q is $(CH_2)_n$; n is 0; R is $CH_3$, $CHF_2$ or $CF_3$; $R^1$ is H; $R^2$ is H; X is Cl or F; Y is Br, F, or Cl; T is H; and Z is $(C_1-C_6)$alkyl, $(C_1-C_6)$alkoxymethyl, $(C_3-C_6)$alkenyloxymethyl, $(C_3-C_6)$alkynyloxymethyl, $(C_1-C_6)$alkyloximyl or $(C_3-C_6)$alkynyloximyl.

More preferably R is $CF_3$, $R^1$ and $R^2$ are hydrogen, X is fluoro, Y is chloro and Z is isopropyloxymethyl, 1-methylpropargyloxymethyl, methyloximyl, isopropyloximyl, propargyloximyl or t-butyloximyl.

In yet a fourth class of the preferred embodiment of the invention are heterocyclic glutarimides of Formula I wherein Z and Y form a heterocyclic ring of the formula

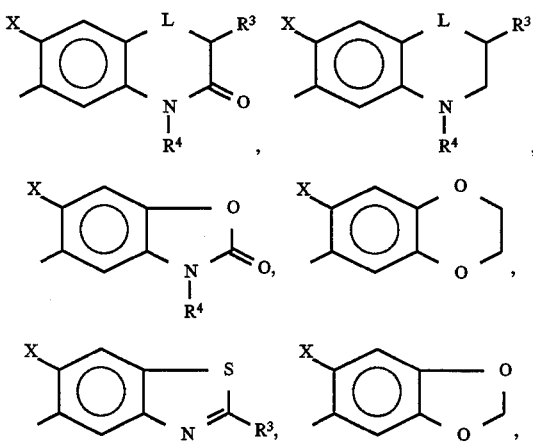

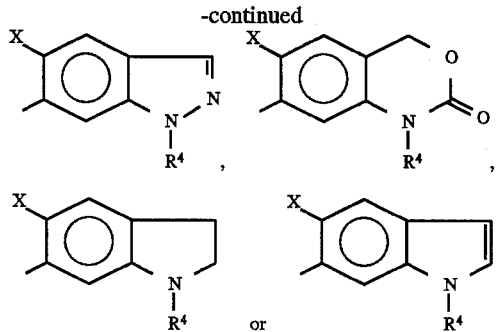

wherein
A and $A^1$ are C=O;
D is CH;
Q is $(CH_2)_n$, where n is 0;
L is O or S;
X is H or F;
R is $(C_1-C_4)$alkyl, $(C_1-C_4)$haloalkyl or phenyl;
$R^1$ is H or $(C_1-C_2)$alkyl;
$R^2$ is H or, together with R and $R^1$, fused phenyl;
$R^3$ is H or $(C_1-C_3)$alkyl; and
$R^4$ is hydrogen, $(C_1-C_8)$alkyl, $(C_3-C_6)$alkenyl, $(C_3-C_6)$alkynyl, $(C_1-C_6)$alkoxy$(C_1-C_6)$alkyl, $(C_1-C_6)$alkylthio$(C_1-C_6)$alkyl, $(C_3-C_6)$cycloalkyl, $(C_3-C_6)$cycloalkyl$(C_1-C_6)$alkyl, phenyl$(C_1-C_6)$alkyl, cyano$(C_1-C_6)$alkyl, $(C_1-C_6)$alkoxycarbonyl$(C_1-C_6)$alkyl, heterocyclyl, heterocyclyl$(C_1-C_6)$alkyl, di$(C_1-C_6)$alkylamino$(C_1-C_6)$alkyl, di$(C_1-C_6)$alkylaminocarbonyl$(C_1-C_6)$alkyl, $(C_1-C_6)$alkoxycarbonyl or $(C_1-C_6)$alkanoyl.

Preferred compounds of this class of the preferred embodiment are compounds of the formula

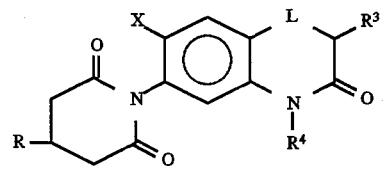

wherein
L is O or S;
X is H or F;
R is $CH_3$, $CHF_2$ or $CF_3$;
$R^3$ is H or $(C_1-C_3)$alkyl; and
$R^4$ is hydrogen, $(C_1-C_6)$alkyl, $(C_3-C_6)$alkenyl, halo $(C_3-C_6)$alkenyl, $(C_3-C_6)$alkynyl, $(C_3-C_6)$cycloalkyl, $(C_3-C_6)$cycloalkyl$(C_1-C_6)$alkyl, $(C_1-C_6)$alkoxymethyl, $(C_1-C_6)$alkylthiomethyl, cyano$(C_1-C_6)$alkyl, heterocyclyl, heterocyclyl$(C_1-C_6)$alkyl, di$(C_1-C_6)$alkylamino$(C_1-C_6)$alkyl or di$(C_1-C_6)$alkylaminocarbonyl$(C_1-C_6)$alkyl.

More preferably X is H or F, R is $CH_3$ $CHF_2$ or $CF_3$, $R^3$ is H, $CH_3$ or $CH_2CH_3$ and $R^4$ is propargyl, allyl, ethoxymethyl, ethyl, n-propyl, isopropyl, n-butyl, isobutyl, s-butyl, 1-ethylpropyl, 2-methoxyethyl, methoxymethyl, methylthiomethyl, 1-cyanoethyl, 1-methylpropargyl, 2-methylallyl, cyanomethyl, cyclopropylmethyl, cyclopentyl, dimethylaminocarbonylmethyl, 2-tetrahydrofuranylmethyl, 3-tetrahydrofuranyl, 2-chloroallyl, or 3,3-dichloroallyl.

Most preferably when R is $CH_3$, $R^3$ is H, L is oxygen and $R^4$ is propargyl, X is F.

Most preferably when R is $CF_3$, $R^3$ is $CH_3$, L is oxygen and $R^4$ is propargyl, X is H or F.

Most preferably when R is $CF_3$, $R^3$ and X are H, and L is oxygen, $R^4$ is propargyl, n-propyl, 1-methylpropargyl, allyl, s-butyl, methoxymethyl or 2-methoxyethyl.

Most preferably when R is $CF_3$, $R^3$ is H, L is oxygen and X is F, $R^4$ is propargyl, cyanomethyl, allyl, methoxymethyl, ethoxymethyl, n-propyl, isopropyl, n-butyl, isobutyl, s-butyl, 1-cyanoethyl, 2-methylallyl, methylthiomethyl, 2-ethylpropyl, cyclopropylmethyl, cyclopentyl, dimethylaminocarbonylmethyl, 2-tetrahydrofuranylmethyl, 3-tetrahydrofuranyl, 2-chloroallyl, 3,3-dichloroallyl or ethyl.

Most preferably when R is $CHF_2$, $R^3$ is H, L is oxygen and X is F, $R^4$ is allyl.

Most preferably when R is $CF_3$, $R^3$ is $CH_2CH_3$, L is oxygen and X is F, $R^4$ is propargyl.

Most preferably when R is $CF_3$, $R^3$ is H, L is sulfur and X is F, $R^4$ is propargyl.

Other preferred compounds of this class of the preferred embodiment are compounds of the formula

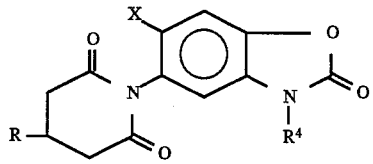

wherein R is $CF_3$ or $CH_3$, X is H or F and R4 is $(C_1-C_6)$ alkyl.

Most preferably, R is $CF_3$, X is F, and X is n-propyl.

The glutarimides of the instant invention can be prepared by a two-step sequence starting from an anilino or amino compound of the formula

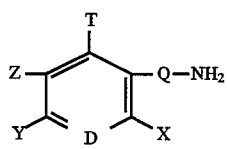

wherein D, T, X, Y, Z and Q are as defined in Formula I above. Compound II is reacted with about an equivalent of a suitably substituted glutaric anhydride having the formula

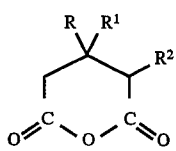

wherein R, $R^1$ and $R^2$ are as defined in Formula I above, to yield a compound having the formula

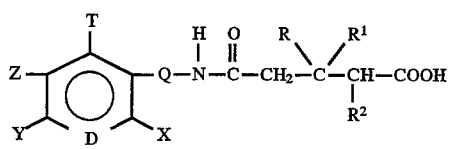

Examples of suitable solvents for this reaction include ethers, such as ethyl ether, tetrahydrofuran (THF) and glyme; hydrocarbons, such as toluene; acetonitrile; N,N-dialkylamides, such as dimethylformamide; and halocarbons such as methylene chloride and chloroform. A mixture of solvents can be used to achieve homogeniety. The reaction is generally carried out at about atmospheric pressure at a temperature of from about $-10°$ C. to about $100°$ C. Preferably the temperature employed is in the range of from about $0°$ C. to about $70°$ C.

The compound of Formula IV is then cyclized in the presence of acetic anhydride and sodium acetate, or acetyl chloride, or ethyl acetate with thionyl chloride and N,N-dimethylformamide to obtain the desired N-substituted glutarimide (Formula V) of the instant invention. The reaction is generally carried out at a temperature of from about $-10°$ C. to about $250°$ C. More preferably the reaction is carried out at a temperature of from about $30°$ C. to about $150°$ C.

The N-substituted glutarimide of Formula V,

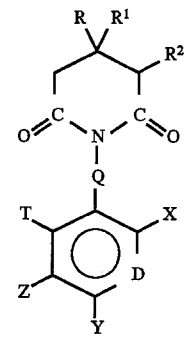

wherein Q is not oxygen, can be converted to the thioglutarimide of the invention (Formula VI),

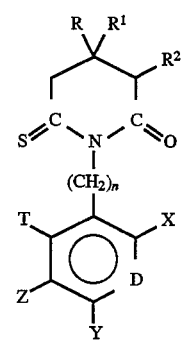

for example, by use of a thiocarbonyl conversion agent such as Lawesson's reagent (2,4-bis(4-methoxyphenyl)-1,3-dithia-2,4-diphosphetane-2,4-disulfide) or phosphorus pentasulfide in the presence of hexamethylphosphoramide or xylenes. The reaction is generally carried out at a temperature of from about $-10°$ C. to about $250°$ C., preferably from about $50°$ C. to about $150°$ C.

The N-substituted glutarimide V (wherein Q is not oxygen) can also be reduced to the corresponding N-substituted piperidine of the invention (Formula VII)

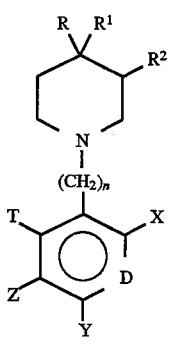

using, for example, a reducing agent such as lithium aluminum hydride. The reaction is generally carried out in an aprotic solvent such as ethyl ether or tetrahydrofuran. The reaction is generally carried out at a temperature range from about $-20°$ C. to about $100°$ C. Preferably the temperature is from about $0°$ C. to about $65°$ C.

The piperidones of the invention (Formula VIII)

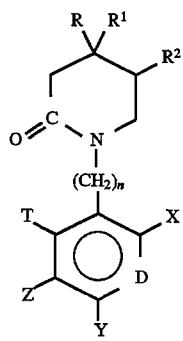

can be prepared by a three step sequence starting from the compound of Formula IV (wherein Q is not oxygen). The glutaramic acid of Formula IV is first reduced to the analogous 5-hydroxypentanamide. For example, a reducing agent such as borane-methyl sulfide complex in a solvent such as tetrahydrofuran or ethyl ether is used. The temperature range is from about −20° C. to about 150° C., preferably from about 0° C. to about 100° C.

The 5-hydroxypentanamide is converted to the corresponding 5-chloropentanamide, for example, by reacting the hydroxy compound with thionyl chloride in an aprotic solvent such as methylene chloride at a temperature range from about −20° C. to about 150° C., preferably from about 0° C. to about 100° C.

The 5-chloropentanamide is then cyclized to the piperidone of Formula VIII, for example, by treatment with base, such as sodium hydroxide in an aprotic solvent such as tetrahydrofuran at a temperature range from about −20° C. to about 150° C., preferably from about 0° C. to about 100° C.

In the case where Z is a substituted carbonyl moiety, the carboxylic acid of Formula V (Z=CO₂H, wherein Q is not oxygen) can be converted to the corresponding acid chloride (Z=C(O)Cl) by reaction with a chlorinating agent, for example thionyl chloride, in an inert solvent, preferably a hydrocarbon such as toluene or chloroform, at a temperature range between −20° C. and 200° C., preferably from about 50° C. to about 100° C. The acid halide is then reacted with the appropriate nucleophile (for example, alcohol, alkyl mercaptan, amine) in the presence of a suitable base, preferably triethylamine or pyridine, to yield the corresponding compound of Formula I. The reaction is carried out in an inert organic solvent, preferably THF or methylene chloride.

In the case where Y and Z together form a heterocyclic ring, the amino-substituted heterocycle is prepared by means known in the art and then reacted with the requisite glutaric anhydride (III) as described above. Alternatively, when the heterocycle contains a site which can be alkylated, the alkylation can be carried out after the reaction with glutaric anhydride and subsequent cyclization has taken place.

In some cases where Z is a substituted alkoxy moiety, the phenol of Formula V (Z=OH, when Q is not oxygen) is treated with a non-nucleophilic base such as sodium hydride and reacted with an appropriate alkylating agent to yield the corresponding glutarimide. The reaction is carried out in an inert organic solvent, for example, tetrahydrofuran or ethyl ether at a temperature range from about −20° C. to about 150° C., preferably from about 0° C. to about 100° C.

In the case where Z is an oximyl moiety, the benzaldehyde of Formula V (Z=CHO, when Q is not oxygen) is reacted with the appropriate alkoxyamine or alkoxyamine salt in a polar organic solvent such as ethanol at a temperature range from about −20° C. to about 150° C., preferably from about 0° C. to about 100° C. When a salt is used, a base such as pyridine may be added to the reaction mixture.

The starting glutaric anhydrides are prepared as is known in the art, for example, in J. Gootjes and W. Th. Nanto, Rec. Trav. Chem, 80, 1183 (1965). Alternatively, ethyl 4,4,4-trifluorocrotonate and sodio diethyl malonate are reacted in the presence of a catalytic amount of a catalyst such as tetrabutylammonium bromide to yield ethyl 2-(trifluoromethyl)propanetrioate which is in turn treated with a strong base such as potassium hydroxide, preferably between about 50° C. and about 150° C., then acidified and decarboxylated to yield 3-(trifluoromethyl)glutaric acid.

The starting anilino and amino are prepared by known methods, as disclosed for example, in U.S. Pat. Nos. 4,439,229, 4,484,940, 4,484,941, 4,594,099, and 4,640,707, and in PCT/EP87/00279 and PCT/US87/00056 and in the references cited therein.

The following examples will further illustrate this invention but are not intended to limit it in any way. In Tables I to IV examples of N-substituted glutarimides are listed with their melting points, when obtained. The proton NMR data are listed in Table V for those compounds for which no melting point is supplied. Specific illustrative preparations of the compounds are described after Table V.

TABLE I

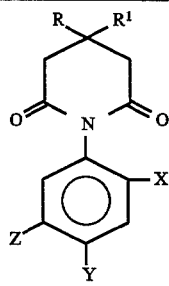

| No. | R,R¹ | X | Y | Z | m.p.(°C.) |
|---|---|---|---|---|---|
| 1. | CF₃,H | F | Cl | OCH₃ | 55–70 |
| 2. | CF₃,H | F | Cl | OCH₂CH₃ | 72–75 |
| 3. | CF₃,H | F | Cl | OCH₂CH₂CH₃ | 106–110 |
| 4. | CF₃,H | F | Cl | OCH₂CH₂CH₂CH₃ | 112–114 |

TABLE I-continued

| No. | R,R¹ | X | Y | Z | m.p.(°C.) |
|---|---|---|---|---|---|
| 5. | $CF_3$,H | F | Cl | $OCH(CH_3)_2$ | 88–90 |
| 6. | $CF_3$,H | F | Cl | $OCH(CH_3)CH_2CH_3$ | oil |
| 7. | $CF_3$,H | F | Cl | $OCH_2CH(CH_3)_2$ | 124–127 |
| 8. | $CF_3$,H | F | Cl | $OCOCH_3$ | 71–76 |
| 9. | $CF_3$,H | F | Cl | $OCH_2CH=CH_2$ | 80–83 |
| 10. | $CF_3$,H | F | Cl | $OCH_2C\equiv CH$ | 88–91 |
| 11. | $CF_3$,H | F | Cl | $OCH_2CN$ | 123.5–127 |
| 12. | $CF_3$,H | F | Cl | $OCH_2OCH_3$ | oil |
| 13. | $CF_3$,H | F | Cl | $OSO_2C_6H_5$ | 214–215 |
| 17. | $CF_3$,H | F | Br | H | 140–143 |
| 18. | $CF_3$,H | F | F | H | 108–113 |
| 19. | $CF_3$,H | F | Cl | OH | 112–114 |
| 20. | $CF_3$,H | H | Cl | Cl | 44–46 |
| 21. | $CF_3$,H | H | Br | $CF_3$ | 99–102 |
| 22. | $CF_3$,H | H | Br | H | 163–164 |
| 23. | $CF_3$,H | H | $CH_3$ | H | 179–182 |
| 24. | $CF_3$,H | H | Cl | $OCH_2C\equiv CH$ | 155–156 |
| 25. | $CF_3$,H | Cl | Cl | $OCH_2C\equiv CH$ | oil |
| 29. | $CH_3$,H | F | Cl | $OCH_2C\equiv CH$ | 130–133 |
| 30. | $CH_3$,H | F | Cl | $OCH(CH_3)_2$ | 104–107 |
| 31. | $CH_3$,H | Cl | Cl | $OCH_2C\equiv CH$ | 170–175 |
| 32. | $CH_3$,H | H | Cl | $OCH_2C\equiv CH$ | 171–174 |
| 33. | $CF_3$,H | F | H | $CO_2CH(CH_3)_2$ | 146–148 |
| 34. | $CH_3$,H | F | Br | H | 99–101 |
| 38. | $CH_3,CH_3$ | F | Cl | $OCH_2C\equiv CH$ | 101–102.5 |
| 39. | $CF_3$,H | CN | Cl | H | 135–138 |
| 40. | $CF_3$,H | H | $SCH_3$ | H | 144–145.5 |
| 41. | $CF_3$,H | F | Cl | $SCH(CH_3)_2$ | oil |
| 42. | $CH_3$,H | F | Cl | $OCOCH_3$ | 135–141 |
| 43. | $CH_2CH_3$,H | F | Cl | $OCH_2C\equiv CH$ | 102–107 |
| 44. | $CH_2CH_3$,H | F | Cl | $OCH(CH_3)_2$ | 81–84 |
| 45. | $CF_2CF_3$,H | F | Cl | $OCH_2C\equiv CH$ | 131–132 |
| 46. | $CF_2CF_3$,H | F | Cl | $OCH(CH_3)_2$ | 66–67.5 |
| 47. | $CH(CH_3)_2$,H | F | Cl | $OCH_2C\equiv CH$ | 103–106 |
| 48. | $CH(CH_3)_2$,H | F | Cl | $OCH(CH_3)_2$ | oil |
| 49. | $C_6H_5$,H | F | Cl | $OCH_2C\equiv CH$ | 188–190 |
| 50. | $CF_3$,H | F | Cl | $SCH_2CO_2CH(CH_3)_2$ | oil |
| 51. | $CF_3$,H | F | Cl | $CO_2CH(CH_3)_2$ | 96–98 |
| 52. | $CF_3$,H | F | Cl | $OCH_2SC_6H_5$ | 108–109.5 |
| 53. | $CF_3$,H | F | Cl | $OCH(CH_3)CN$ | 175–177(dec) |
| 54. | $CF_3$,H | F | Cl | $OCH_2CO_2CH_3$ | 90–91 |
| 55. | $CF_3$,H | F | Cl | $OCH(OCH_3)CO_2CH_3$ | 40.5–43 |
| 56. | $CF_3$,H | F | Cl | $SCH_2CO_2CH_3$ | oil |
| 57. | $CF_3$,H | F | Cl | $SCH_2CO_2H$ | 137–139 |
| 58. | $CF_3$,H | F | Cl | SH | 68–72 |
| 59. | $CF_3$,H | F | Cl | $SCOCH_3$ | oil |
| 60. | $CF_3$,H | F | Cl | $SCH_3$ | 114–116 |
| 61. | $CF_3$,H | F | Cl | $CO_2CH_3$ | 172–174 |
| 62. | $CF_3$,H | F | Cl | $CO_2H$ | 220–225 |
| 63. | $CH_2CH_3$,H | H | Br | H | 140–145 |
| 66. | $CH_3$,H | H | F | H | 125–127 |
| 67. | $CH_3$,H | H | Cl | H | 163–164 |
| 68. | $CH_3$,H | H | I | H | 174–177 |
| 69. | $CH_3$,H | H | $OCH_3$ | H | 112–113 |

TABLE I-continued

| No. | R,R¹ | X | Y | Z | m.p.(°C.) |
|---|---|---|---|---|---|
| 70. | CH₃,H | H | Cl | Cl | 156–159 |
| 71. | CF₃,H | F | Cl | CO₂CH₂CH₃ | 104–105 |
| 72. | CF₃,H | F | Cl | CO₂(CH₂)₂CH₃ | 79–80 |
| 73. | CF₃,H | F | Cl | OCH₂C₆H₅ | 121–122.5 |
| 74. | CF₃,H | F | Cl | CO₂CH(CH₃)CO₂CH₃ | 94–96 |
| 75. | CF₃,H | F | Cl | CO₂CH₂CH(CH₃)₂ | 82–85 |
| 76. | CF₃,H | F | Cl | OCH₂C≡CCH₃ | 95–97 |
| 77. | CF₃,H | F | Cl | CONHC₆H₅ | 55–60 |
| 78. | CF₃,H | F | Cl | CONHCH(CH₃)₂ | 95–112 |
| 79. | CF₃,H | F | Cl | CH₂OCOCH₃ | 115–116.5 |
| 80. | CF₃,H | Cl | Cl | CO₂CH(CH₃)₂ | oil |
| 81. | CF₃,H | F | Cl | CH₂OCH₃ | 86–88 |
| 82. | CF₃,H | F | Cl | CH₂OCH(CH₃)₂ | 77–79 |
| 83. | CF₃,H | F | Cl | CH₂OCH₂C≡CH | oil |
| 92. | CF₃,H | F | Cl | CH₃ | 119–120 |
| 93. | CF₃,H | F | Cl | CH=NOCH₃ | 150.5–152.5 |
| 94. | CF₃,H | F | Cl | CHO | 146–148.5 |
| 95. | CF₃,H | F | Cl | COCH₃ | 127–129 |
| 99. | CF₃,H | H | H | OCH₂C≡CH | 70.5–72 |
| 100. | CF₃,H | F | Cl | CO₂N=C(CH₃)₂ | 144–145 |
| 101. | CF₃,H | F | Cl | CO₂CH₂PO(OC₂H₅)₂ | oil |
| 102. | CF₃,H | F | Cl | COSC₂H₅ | 102–104 |
| 103. | CF₃,H | F | Cl | CO₂CH₂CO₂C₂H₅ | 139–140 |
| 104. | CF₃,H | F | Cl | COSCH(CH₃)₂ | 102–105 |
| 106. | CF₃,H | F | Cl | CH₂SCH(CH₃)₂ | 107–109 |
| 107. | CF₃,H | F | Cl | CH₂SC₂H₅ | oil |
| 108. | CF₃,H | F | Cl | CH₂OC₆H₅ | 120–122 |
| 109. | CF₃,H | F | Cl | CH₂SC₆H₅ | oil |
| 110. | CF₃,H | F | Cl | CO₂CH₂C≡CH | 120–123 |
| 111. | CF₃,H | F | Cl | CO₂CH(CH₃)C≡CH | 45–50 |
| 112. | CF₃,H | F | Cl | CO₂CH₂CH₂C≡CH | oil |
| 113. | CF₃,H | F | Cl | CO₂CH(CH₃)CN | oil |
| 114. | CF₃,H | F | Cl | CONHOCH₃ | 158–162 |
| 115. | CF₃,H | F | Cl | CH₂OCH(CH₃)CO₂C₂H₅ | oil |
| 116. | CF₃,H | F | Cl | CO₂CH₂CH₂OCH₃ | oil |
| 117. | CF₃,H | F | Cl | CO₂CH(CH₃)CH₂OCH₃ | oil |
| 118. | CF₃,H | F | Cl | CO₂CH(CH₃)CH₂CH₃ | oil |
| 127. | CF₃,H | F | Cl | CO₂-cyclopentyl | 77–78 |
| 130. | CF₃,H | F | Cl | CO₂-(tetrahydrofuran-yl) | 52–55 |
| 133. | CF₃,H | F | Cl | CONHC(CH₃)₂C≡CH | 166–170 |
| 135. | CF₃,H | F | Cl | CO₂-cyclobutyl | oil |
| 140. | CF₃,H | F | Cl | OCH₂CH₂C≡CH | 89–91 |
| 141. | CF₃,H | F | Cl | OCH(CH₃)C≡CH | 102–104 |

TABLE I-continued

| No. | R,R¹ | X | Y | Z | m.p.(°C.) |
|---|---|---|---|---|---|
| 144. | CF₃,H | F | Cl | CH₂OCH(CH₃)C≡CH | oil |
| 148. | CF₃,H | F | OCH₃ | NHCOCH₃ | 155–157 |
| 150. | CF₃,H | F | Cl | CH=NOCH₂CH=CH₂ | oil |
| 152. | CF₃,H | F | CN | H | 154–155 |
| 156. | CF₃,H | F | Cl | CH=NOCH₂C₆H₅ | 187–188 |
| 158. | CF₃,H | F | Cl | CH=NOC₂H₅ | 111.5–113.5 |
| 159. | CF₃,H | F | Cl | CH=NOH | 75–80(subl**) |
| 160. | CF₃,H | F | Cl | OCH₂CH₂OCH₃ | 95–97 |
| 161. | CF₃,H | F | Cl | CO₂C₆H₅ | 206–208 |
| 162. | CF₃,H | F | Cl | CO₂CH₂Si(CH₃)₃ | 95–98 |
| 163. | CF₃,H | F | Cl | CO₂-cyclohexyl | 53–55 |
| 164. | CF₃,H | F | Cl | CONHCH₂C≡CH | 63–65 |
| 168. | CF₃,H | F | Cl | CH=NOC(CH₃)₃ | 140–141.5 |
| 169. | CF₃,H | F | Cl | CN | 210–212 |
| 172. | CF₃,H | F | Cl | C(CH₃)=NOCH₃ | 130–135 |
| 173. | CF₃,H | F | Cl | C(CH₃)=NOH | 178–179.5 |
| 174. | CF₃,H | F | Cl | C(CH₃)=NOCH₂CH₃ | 106–109 |
| 175. | CF₃,H | F | Cl | C(CH₃)=NOC(CH₃)₃ | 132–134 |
| 176. | CF₃,H | F | Cl | C(CH₃)=NOCH₂CH=CH₂ | 95.5–98 |
| 177. | CF₃,H | F | Cl | CO₂⁻NH₃CH(CH₃)₂⁺ | 168–173 dec |
| 178. | CF₃,H | F | Cl | C(CH₃)=NOCH₂C₆H₅ | 92–97 |
| 180. | CF₃,H | H | OCF₃ | H | 113–116 |
| 183. | CF₃,H | H | Cl | N(CH₃)C(=O)CH₃ | 203–204 |
| 185. | CF₃,H | H | NO₂ | H | 133–134 |
| 186. | CF₃,H | F | Cl | CH=NOCH(CH₃)₂ | 140–141.5 |
| 187. | CF₃,H | F | Cl | CH=NOCH₂C≡CH | 57–61 |
| 190. | CF₃,H | F | Cl | OSO₂CH₂CH₃ | 41–44 |
| 191. | CF₃,H | H | CF₃ | H | 143–144 |
| 192. | CF₃,H | F | Cl | O-cyclopentyl | 63–65.5 |
| 193. | CF₃,H | F | Cl | —CH(O)—O (tetrahydrofuranyl) | 157–159 |
| 194. | CF₃,H | F | Cl | CO₂CH₂C₆H₅ | 50–55 |
| 195. | CF₃,H | F | Cl | CO₂CH₂CH=CH₂ | 107–108 |
| 196. | CF₃,H | F | Cl | OCH₂-cyclopropyl | 91–92 |
| 197. | CF₃,H | F | Cl | CO₂CH₂-cyclopropyl | 188–90 |
| 199. | CF₃,H | F | Cl | CO₂CH₂C≡CI | 55–60 |
| 201. | CH₃,H | F | Cl | CO₂CH(CH₃)₂ | 101–103 |
| 202. | CF₃,H | F | Cl | SO₂CH₂CH(CH₃)₂ | 48–51 |
| 203. | CF₃,H | F | Cl | SCH₂CH(CH₃)₂ | 71–74 |

TABLE I-continued

[Structure: glutarimide with R, R¹ substituents on carbon and N-phenyl with X, Y, Z substituents]

| No. | R,R¹ | X | Y | Z | m.p.(°C.) |
|---|---|---|---|---|---|
| 205. | CF₃,H | F | Cl | CH=NOCH₂—(4-Cl-phenyl) | 137.5–140 |
| 206. | CF₃,H | F | Br | CO₂CH(CH₃)₂ | 98–99 |
| 207. | CF₃,H | H | Cl | CO₂CH(CH₃)₂ | 113–115 |
| 209. | CF₃,H | F | F | F | 97–99 |
| 212. | CF₃,H | F | F | OCH₂C≡CH | 67–68 |
| 213. | CF₃,H | F | Cl | CO₂⁻K⁺ | 133–143 |
| 214. | CF₃,H | H | CH₃ | Cl | 148–149.5 |
| 215. | CF₃,H | F | Cl | isoxazolidinyl-C(=O)N (N,O-ring) | 175–178 |
| 216. | CF₃,H | F | Cl | tetrahydrofuran-3-yloxy | 125–128 |
| 218. | CF₃,H | F | Cl | CO₂N=CHCH(CH₃)₂ | 110–117 |
| 219. | CF₃,H | F | Cl | CO₂CH₂—(furan-2-yl) | 105–107 |
| 220. | CF₃,H | F | Cl | CO₂CH₂—(pyridin-2-yl) | oil |
| 221. | CF₃,H | F | Cl | CO₂N=C(CH₃)OCH₂CH₃ | oil |
| 222. | CF₃,H | F | Cl | NO₂ | 164–167 |
| 223. | CF₃,H | F | F | CO₂CH(CH₃)₂ | 127–129 |
| 224. | CF₃,H | F | Br | OCH₂C≡CH | 105–107.5 |
| 225. | CF₃,H | F | Cl | N(COCH₃)₂ | 164–169 |
| 227. | CF₃,H | F | Cl | —C=N-oxazoline with gem-diCH₃ (OCH₂C(CH₃)₂—) | 165–173 |
| 228. | CF₃,H | F | CF₃ | CO₂CH(CH₃)₂ | 89–92 |
| 229. | CF₃,H | F | OCH₃ | OCH₃ | 55–60 |
| 231. | CF₃,H | F | Cl | OCH₂—(pyridin-2-yl) | 152–153 |
| 232. | CF₃,H | F | Cl | OCH₂—(tetrahydrofuran-2-yl) | 84–86 |

TABLE I-continued

| No. | R,R¹ | X | Y | Z | m.p.(°C.) |
|---|---|---|---|---|---|
| 234. | $CF_3$,H | F | Cl | (cyclohexylmethoxy) $OCH_2$-cyclohexyl | 144–147 |
| 236. | $CF_3$,H | F | Cl | $OSO_2CH_3$ | 96–99 |
| 237. | $CHF_2$,H | F | Cl | $CO_2CH(CH_3)_2$ | oil |
| 240. | $CF_3$,H | F | Cl | $OCH(CH_3)CH=CH_2$ | oil |
| 241. | $CF_3$,H | F | Cl | $OCH_2C(Cl)=CH_2$ | 103–106 |
| 242. | $CF_3$,H | F | Cl | $CO_2CH(CH_3)CH=CH_2$ | 79–81 |
| 243. | $CF_2H$,H | F | Cl | $OCH_2C\equiv CH$ | 110–111.5 |
| 244. | $CF_3$,H | F | Cl | $OCH_2CH=C(Cl)_2$ | 106–108 |
| 245. | $CF_3$,H | F | Cl | $OCH_2$-(2-oxiranyl) | 121–123.3 |
| 246. | $CF_3$,H | F | Cl | $S(O)CH_2CH(CH_3)_2$ | 133–134 |
| 247. | $CH_2F$,H | F | Cl | $CO_2CH(CH_3)_2$ | |
| 248. | $CH_2F$,H | F | Cl | $OCH_2C\equiv CH$ | |
| 264. | $CF_3$,H | F | Cl | $NCH_2CH_2CH_3$ | |
| 265. | $CF_3$,H | F | $OCH_3$ | $NCH_2CH_2CH_3$ | |
| 266. | $CF_3$,H | F | Cl | $NCH_2C\equiv CH$ | |
| 267. | $CF_3$,H | F | Cl | $NCH_2CH=CH_2$ | |
| 268. | $CF_3$,H | F | Cl | $CO_2CH(CH_3)$-(2-oxiranyl) | |
| 269. | $CF_3$,H | F | Cl | $C(OCH_3)=NOCH_3$ | |
| 271. | $CF_3$,H | F | $OCH_3$ | $CO_2CH(CH_3)_2$ | |
| 272. | $CF_3$,H | F | $OCHF_2$ | $CO_2CH(CH_3)_2$ | |
| 273. | $CF_3$,H | F | $OCF_3$ | $CO_2CH(CH_3)_2$ | |

***"subl" means sublimes.

TABLE II

| No. | R,R¹ | X | Y | Z | A | A¹ | Q | T | D | m.p. (°C.) |
|---|---|---|---|---|---|---|---|---|---|---|
| 14. | $CF_3$,H | F | Cl | $OCH(CH_3)_2$ | $CH_2$ | C=O | — | H | CH | 98–102 |
| 15. | $CF_3$,H | F | Cl | $OCH_2C\equiv CH$ | $CH_2$ | $CH_2$ | — | H | CH | oil |

TABLE II-continued

| No. | R,R¹ | X | Y | Z | A | A¹ | Q | T | D | m.p. (°C.) |
|---|---|---|---|---|---|---|---|---|---|---|
| 16. | CF₃,H | F | F | H | C=O | C=O | — | F | CH | 94–97 |
| 26. | CF₃,H | H | Cl | H | C=O | C=O | — | H | N | 119–121 |
| 27. | CF₃,H | F | Cl | H | C=O | C=O | CH₂ | H | CH | 113–115 |
| 28. | CF₃,H | H | Cl | H | C=O | C=O | CH₂ | H | CH | 114–119 |
| 35. | CH₃,H | H | Cl | H | C=O | C=O | — | H | N | 154 |
| 36. | CH₃,H | H | F | H | C=S | C=O | — | H | CH | 84.5–87.5 |
| 37. | CH₃,H | H | F | CN | C=O | C=O | — | F | CH | 92–94 |
| 64. | CH₃,H | H | Cl | H | C=O | C=O | O | H | CH | 148–152 |
| 65. | CH₃,H | H | NO₂ | CO₂CH₃ | C=O | C=O | O | H | CH | 152–155 |
| 132. | CH₃,H | F | Cl | H | C=O | C=O | — | F | CH | 134–135 |

TABLE III

| No. | X | L | M | R | R³ | R⁴ | m.p. (°C.) |
|---|---|---|---|---|---|---|---|
| 84. | H | O | C=O | CF₃ | CH₃ | CH₂C≡CH | 100–102 |
| 85. | H | O | C=O | CF₃ | H | CH₂C≡CH | 203–204.5 |
| 88. | F | O | C=O | CF₃ | CH₃ | CH₂C≡CH | 147–148 |
| 89. | F | O | C=O | CF₃ | H | CH₂C≡CH | 182–183 |
| 96. | F | O | C=O | CF₃ | H | CH₂CN | 126–128 |
| 97. | F | O | C=O | CF₃ | H | CH₂CH=CH₂ | 126–128 |
| 98. | F | O | C=O | CF₃ | H | CH₂OCH₂CH₃ | 151–152 |
| 105. | H | O | C=O | CF₃ | H | CH₂CH₂CH₃ | 170–171 |
| 121. | F | O | C=O | CF₃ | H | CH₂SCH₃ | oil |
| 122. | F | O | C=O | CF₃ | H | CH₂CH₂CH₃ | oil |
| 124. | H | S | C=O | CF₃ | H | CH₂C≡CH | 165–168 |
| 126. | F | O | C=O | CF₃ | H | CH₂C₆H₅ | 212–216 |
| 128. | F | O | C=O | CF₃ | H | CH₂CH(CH₃)₂ | 180–181 |
| 129. | F | O | C=O | CF₃ | H | CH(CH₃)CH₂CH₃ | 108–109 |
| 131. | F | O | C=O | CF₃ | H | CH₃ | 170–173 |
| 134. | F | O | C=O | CF₃ | H | CH₂(CH₂)₆CH₃ | 91–94 |
| 136. | H | O | CH2 | CF₃ | H | CH₂CH₂CH₃ | 68–71 |
| 137. | F | O | C=O | CF₃ | H | CH₂CO₂CH(CH₃)₂ | 164–166 |
| 138. | F | O | C=O | CF₃ | H | H | oil |
| 139. | F | O | C=O | CF₃ | H | COCH₃ | oil |
| 142. | F | O | C=O | CF₃ | H | CO₂CH₃ | oil |
| 143. | F | O | C=O | CF₃ | H | CH(CH₃)₂ | oil |
| 145. | F | O | C=O | CH₃ | H | CH₂C≡CH | 192–194 |
| 146. | F | O | C=O | CF₃ | H | CH(CH₂CH₃)₂ | oil |
| 147. | H | O | C=O | CF₃ | H | CH(CH₃)C≡CH | 68–70 |
| 149. | F | O | C=O | CF₃ | H | CH(CH₃)CN | oil |
| 151. | H | O | C=O | CF₃ | H | CH₂OCH₃ | 138–140 |
| 154. | H | O | C=O | CF₃ | H | CH₂CH=CH₂ | 144–146 |

TABLE III-continued

| No. | X | L | M | R | R³ | R⁴ | m.p. (°C.) |
|---|---|---|---|---|---|---|---|
| 155. | F | O | C=O | CF₃ | H | CH₂C(CH₃)=CH₂ | 200–202 |
| 157. | H | O | C=O | CF₃ | H | CH(CH₃)CH₂CH₃ | 115–118 |
| 165. | F | O | C=O | CF₃ | H | CH₂CH₃ | 148–150 |
| 166. | F | O | C=O | CF₃ | H | CH₂CH₂CH₂CH₃ | 165–167 |
| 167. | H | O | C=O | CF₃ | H | CH₂CH₂OCH₃ | 143–146 |
| 171. | H | O | C=O | CH₃ | H | CH₂C≡CH | 200–204 |
| 179. | F | O | C=O | CF₃ | H | CH₂CH₂CH₂Cl | 138–140 |
| 182. | F | O | C=O | CF₃ | H | CH₂— | 146–148 |
| 184. | F | S | C=O | CF₃ | H | CH₂CH=CH₂ | 148–150 |
| 188. | F | O | C=O | CF₃ | H | CH₂OCH₃ | 175–176 |
| 189. | F | O | C=O | CF₃ | H | 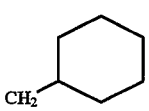 | oil |
| 200. | F | O | C=O | CF₃ | H | CH₂CON(CH₃)₂ | >200 |
| 204. | F | O | C=O | CF₃ | H | 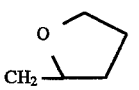 | 180–181 |
| 208. | F | O | C=O | CF₃ | H |  | foam |
| 210. | F | O | C=O | CF₃ | H | 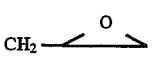 | foam |
| 211. | H | O | C=O | CF₃ | H | CH(CH₃)₂ | 153–155 |
| 217. | H | O | C=O | CF₃ | H | CH₂CH₂Cl | 109–110 |
| 226. | F | O | C=O | CF₃ | H | CH₂CH₂N(CH₃)₂ | 122–124 |
| 230. | F | O | C=O | CF₃ | H | CH₂C(Cl)=CH₂ | 178–180 |
| 233. | F | O | C=O | CF₃ | H | CH₂CH=CCl₂ | 173–175 |
| 235. | F | O | C=O | CF₃ | CH₂CH₃ | CH₂C≡CH | foam |
| 238. | F | O | C=O | CF₂H | H | CH₂C≡CH | >200 |
| 239. | F | O | C=O | CF₃ | H | CH₂—△O | foam |
| 249. | F | O | C=O | CFH₂ | H | CH₂C≡CH | |
| 250. | H | O | C=O | CFH₂ | H | CH₂C≡CH | |
| 251. | H | O | C=O | CF₂H | H | CH₂C≡CH | |
| 252. | F | O | C=O | CF₂H | H | CH₂CH=CH₂ | |
| 253. | F | O | C=O | CF₂H | H | CH(CH₃)₂ | |
| 254. | F | O | C=O | CF₂H | H | CH₂CH(CH₃)₂ | |
| 255. | F | O | C=O | CF₂H | H | CH₂OCH₃ | |
| 256. | F | O | C=O | CFH₂ | H | CH₂OCH₃ | |
| 257. | F | O | C=O | CFH₂ | H | CH(CH₃)₂ | |
| 258. | F | O | C=O | CFH₂ | H | CH₂CH(CH₃)₂ | |
| 259. | F | O | C=O | CFH₂ | H | CH₂CH=CH₂ | |
| 260. | F | O | C=O | CF₃ | H | CH₂C(=O)CH₃ | |
| 261. | F | O | C=O | CF₃ | H | CH₂CH(OH)CH₃ | |

TABLE IV

| No. | m.p. (°C.) |
|---|---|
| 86. | 178–179 |
| 87. | 197.5–199 |
| 90. | 152–155 |
| 91. | 132–137 |
| 119. | 165 |
| 120. | 177–178 |
| 123. | 195 |
| 125. | 185–186 |
| 153. | 222–223 |
| 170. | 95.5–98 |
| 181. | 148–152 |
| 198. | 158–160 |
| 262. | |
| 263. | |
| 270. | |
| 275. | 285–287 |

TABLE V

NMR DATA

| Ex. No. | Solvent | (200 MHz, delta scale in ppm, Tetramethylsilane (TMS) standard) |
|---|---|---|
| 6. | CDCl₃ | 1.0(t, 3H), 1.3(d, 3H), 1.6–1.9(m, 2H), 2.8–3.2(m, 5H), 4.1–4.3(m, 1H), 6.7(dd, 1H), 7.3(dd, 1H) |
| 12. | CDCl₃ | 3.0(m, 4H), 3.5(s, 3H), 3.5(m, 1H), 5.2(s, 2H), 7.0(d, 1H), 7.3(d, 1H) |
| 15. | CDCl₃ | 1.8(m, 4H), 2.2(m, 1H), 2.6(m, 1H), 2.7(t, 2H), 3.5(d, 2H), 4.7(s, 2H), 6.7(d, 1H), 7.1(d, 1H) |
| 25. | CDCl₃ | 2.6(t, 1H), 2.9–3.3(m, 5H), 4.9(d, 2H), 6.9(m, 1H), 7.6(m, 1H) |
| 41. | d₆-acetone | 1.3(d, 6H), 3.1(m, 4H), 3.4(m, 1H), 4.0(m, 1H), 7.4(t, 1H), 7.5(d, 1H) |
| 48. | d₆-acetone | 1.0(d, 6H), 1.4(d, 6H), 1.7(m, 1H), 2.5–3.0(m, 4H), 4.1(m, 1H), 4.6(m, 1H), 7.1(m, 1H), 7.4(m, 1H) |
| 50. | d₆-acetone | 1.2(d, 6H), 3.1(m, 4H), 3.5(m, 1H) 3.8(d, 2H), 4.9(m, 1H), 7.4(dd, 1H), 7.5(d, 1H) |
| 56. | d₆-acetone | 3.2(m, 4H), 3.7(s, 3H), 3.6(m, 1H), 3.8(d, 2H), 7.5(dd, 1H), 7.6(d, 1H) |
| 59. | d₆-acetone | 2.5(s, 3H), 3.2(m, 4H), 3.6(m, 1H), 7.5(t, 1H), 7.6(d, 1H) |
| 80. | CDCl₃ | 1.33(d, 6H), 2.80–3.23(m, 5H), 5.25(heptet, 1H), 7.65(m, 2H) |
| 83. | CDCl₃ | 2.5(s, 1H), 2.8–3.2(m, 5H), 4.25(d, 2H), 4.65(s, 2H), 7.2–7.4(m, 2H) |
| 101. | d₆-DMSO | 1.3(t, 6H), 2.9–3.2(m, 4H), 3.6(m, 1H), 4.1 (quintet, 4H), 4.7(d, 2H), 7.8–8.0(m, 2H) |
| 107. | CDCl₃ | 1.2–1.3(t, 3H), 2.5(q, 2H), 2.9–3.3(m, 5H), 3.8(s, 2H), 7.25(d, 1H), 7.30(d, 1H) |
| 109. | CDCl₃ | 2.8–3.2(m, 5H), 4.1 (s, 2H), 6.9–7.1(q, 1 H), 7.2–7.4(m, 6H) |
| 112. | CDCl₃ | 2.02(s, 1H), 2.64(td, 2H), 2.82–3.28(m, 5H), 4.39(t, 2H), 7.36(d, 1H), 7.80(dd, 1H) |
| 113. | d₆-DMSO | 1.70(d, 3H), 2.96–3.19(m, 5H), 5.78(m, 1H), 7.86–8.08(m, 2H) |
| 115. | CDCl₃ | 1.3(t, 3H), 1.4–1.5(d, 3H), 2.8–3.2(m, 5H), 4.1–4.2(q, 1H), 4.2–4.3(q, 2H), 4.55(d, 1H), 4.75(d, 1H), 7.2–7.3(d, 1H), 7.3–7.4(d, 1H) |
| 116. | CDCl₃ | 2.8–3.2(m, 5H), 3.37(s, 3H), 3.72(m, 2H), 4.45(t, 2H), 7.35(d, 1H), 7.78(d, 1H) |
| 117. | CDCl₃ | 1.35(d, 3H), 2.86–3.22(m, 5H), 3.38(s, 3H), 3.55(m, 2H), 5.35(m, 1H), 7.35(d, 1H), 7.73(d, 1H) |
| 118. | CDCl₃ | 0.92(t, 3H), 1.35(d, 3H), 1.70(heptet, 2H), 2.85–3.25(m, 5H), 5.10(sextet, 1H), 7.35(d, 1H), 7.7(dd, 1H) |
| 121. | d₆-acetone | 2.2(s, 3H), 3.1(m, 4H), 3.5(m, 1H), 4.8(s, 2H), 5.1(d, 2H), 6.9(d, 1H), 7.1(t, 1H) |
| 122. | d₆-acetone | 0.9(t, 3H), 1.7(m, 2H), 3.1(m, 4H), 3.5(m, 1H) 3.9(m, 2H), 4.7(s, 2H), 7.0(d, 1H), 7.1(d, 1H) |
| 135. | CDCl₃ | 1.65–2.00(m, 2H), 2.20(m, 2H), 2.45(m, 2H), 2.85–3.25(m, 5H), 5.20(quintet, 1H), 7.30(d, 1H), 7.75(d, 1H) |
| 138. | d₆-acetone | 3.1(m, 4H), 3.5(m, 1H), 4.7(s, 2H), 6.8(d, 1H), 6.9(d, 1H), 9.8(bs*, 1H) |
| 139. | d₆-acetone | 2.6(s, 3H), 3.2(bm**, 4H), 3.6(m, 1H), 4.9(s, 2H), 7.1(d, 1H), 7.7(d, 1H) |
| 142. | d₆-acetone | 3.1(bm, 4H), 3.6(m, 1H), 4.0(s, 3H), 4.8(s, 2H), 7.0(d, 1H), 7.4(d, 1H) |
| 143. | d₆-acetone | 1.5(d, 6H), 3.1(m, 4H), 3.5(m, 1H), 4.6(s, 2H), 4.7(m, 1H), 6.9(d, 1H), 7.2(d, 1H) |
| 144. | CDCl₃ | 1.55(d, 3H), 2.5(d, 1H), 2.8–3.3(m, 5H), 4.3(m, 1H), 4.55(d, 1H), 4.80(d, 1H), 7.2(d, 1H), 7.35(d, 1H) |
| 146. | d₆-acetone | 0.9(d, 6H), 1.8(m, 4H), 3.0(m, 4H), 3.5(m, 1H), 4.5(bm, 1H), 4.7(s, 2H), 6.9(d, 1H), 7.2(d, 1H) |
| 149. | d₆-DMSO | 0.9(d, 3H), 3.2(m, 4H), 3.6(m, 1H), 4.8(s, 2H), 6.0(quintet, 1H), 7.1(d, 1H), 7.3(d, 1H) |
| 150. | CDCl₃ | 2.75–3.25(m, 5H), 4.6(d, 2H), 5.3(t, 2H), 6.0–6.1(m, 1H), 7.2(t, 1H), 7.7(dd, 1H), 8.4(s, 1H) |
| 189. | d₆-acetone | 2.1(m, 4H), 2.3(m, 4H), 3.2(m, 4H), 3.5(m, 1H), 4.6(s, 2H), 4.7(m, 1H), 7.0(d, 1H), 7.4(d, 1H) |
| 208. | d₆-acetone | 1.8(m, 1H), 1.9(m, 3H), 3.1(m, 4H), 3.5(m, 1H), 3.8(m, 2H), 4.2(m, 3H), 4.7(s, 2H), 6.9(d, 1H), 7.2(d, 1H) |
| 210. | d₆-acetone | 2.2(m, 2H), 3.1(m, 4H), 3.5(m, 1H), 3.8(m, 2H), 3.9(m, 2H), 4.6(s, 2H), 5.5(m, 1H), 7.0(d, 1H), 7.3(dd, 1H) |
| 220. | d₆-acetone | 3.0–3.4(m, 4H), 3.55(m, 1H), 5.45(s, 2H), 7.35(dd, 1H), 7.53(d, 1H), 7.62(d, 1H), 7.85(td, 1H), 7.98(dd, 1H), 8.59(d, 1H) |
| 221. | d₆-acetone | 1.34(t, 3H), 2.13(s, 3H), 3.0–3.3(m, 4H), 3.55(m, 1H), 4.22(q, 2H), 7.65(d, 1H), 7.90(dd, 1H) |
| 235. | d₆-acetone | 1.1(t, 3H), 1.9(m, 2H), 2.8(d, 1H), 3.1(m, 4H), 3.5(m, 1H), 4.7(m, 3H), 7.0(m, 2H) |
| 237. | d₆-acetone | 1.5(d, 6H), 2.9–3.2(m, 5H), 5.2(heptet, 1H), 6.2(tdd, 1H), 7.5(dd, 1H), 7.8(dd, 1H) |
| 239. | d₆-acetone | 2.6(m, 1H), 2.7(m, 1H), 3.1(m, 4H), 3.5(m, b, 2H), 3.8(dt, 1H), 4.3(dt, 1H), 4.8(s, 2H), 6.9(d, 1H), 7.2(t, 1H) |
| 240. | CDCl₃ | 1.5(d, 3H), 3.0(m, 5H), 4.65 (t, 1H), 5.15(d, 1H), 5.25(d, 1H), 5.85(m, 1H), 6.65(dd, 1H), 7.25(d, 1H) |

*bs = broad singlet
**bm = broad multiplet

EXAMPLE A: Preparation of 4-chloro-2-fluoro-5-propargyloxyaniline

Into a 300 milliliter (ml), three-necked round-bottomed flask equipped with an overhead stirrer, dropping funnel and thermometer were placed 5-acetamido-2-chloro-4-fluorophenol (21.0 gram (g), 0.103 mole) and dimethyl sulfoxide (DMSO) (100 ml). The mixture was stirred at room temperature and aqueous potassium hydroxide (KOH) (7.0 g KOH, 88% w/w, 1.01 equivalents (eq) dissolved in 10 ml H₂O) was added dropwise over 10 minutes. An exotherm was noted (25° to 40° C.) during the addition. The solution was stirred for 1 hour, and then a solution of propargyl bromide (80% in toluene, 12.7 ml, 1.10 eq) was added dropwise. An exotherm from 25° to 40° C. was noted during addition. The mixture was stirred at ambient temperature overnight.

In the morning, thin layer chromatography (TLC) (silica gel, 1:1 v/v hexanes/ethyl acetate (EtOAc)) showed that the reaction was complete. The mixture was poured into ice water (600 ml), filtered, washed with water and dried in vacuo at 50° C. overnight to give the expected propargyloxyacetanilide as a tan powder (24.0 g, 96%, m.p. 142°–5° C.).

Into a 250 ml, three-necked round-bottomed flask equipped with an overhead stirrer, thermometer and condenser were placed the propargyloxyacetanilide (9.64 g, 40 mmol), ethanol (absolute, 43 ml), water (56 ml) and concentrated aqueous hydrochloric acid (HCl) (35% w/w, 37.5 ml). A heating mantle was used to heat the mixture to reflux with stirring. After 1 hour at reflux (92° C.), TLC (silica gel, 3:1 hexanes/EtOAc, v/v) of a basified aliquot indicated that the reaction was complete. The mixture was poured into ice water (200 ml) and brought to pH 10 using 50% aq. sodium hydroxide (NaOH) (25 ml) during which time a brown solid precipitated. The mixture was extracted with ether (3×100 ml) and the combined organic layers were washed (2×50 ml water, 1×50 ml brine), and dried over anhydrous magnesium sulfate (MgSO$_4$). The mixture was filtered, the solvent evaporated in vacuo and dried overnight at 25° C. to give the expected aniline as a brown oil.

EXAMPLE B: 3-(trifluoromethyl)glutaric anhydride

To 115 mg (5 mmol) of sodium metal (cut into small pieces and washed with hexanes) in 5 ml of THF was added a solution of diethyl malonate (800 mg, 5 mmol) in 10 ml THF. The mixture was stirred at room temperature until all of the sodium metal was consumed (2–3 hours). A catalytic amount of tetrabutylammonium bromide was added, followed by a THF solution (10 ml) of ethyl 4,4,4-trifluorocrotonate (0.84 g, 5 mmol). This mixture was warmed to 40° C. and stirred for 17 hours. after cooling to 10° C., glacial acetic acid (300 mg, 5 mmol) was added and the THF was removed in vacuo. The resulting residue was treated with a solution of 87.3% KOH (1.28 g, 20 mmol) in 10 ml water and refluxed for 4.5 hours. After cooling to 10° C., 2.5 ml (26 mmol) of conc. HCl was added dropwise via pipette and the mixture was again heated to reflux until CO$_2$ evolution had ceased (ca. 1 hour). The solution was cooled to 15° C. and extracted with Et$_2$O (3×10 ml). The combined organic phases were dried over Na$_2$SO$_4$, filtered and concentrated in vacuo to afford 3-(trifluoromethyl)glutaric acid as a white solid in 95% yield (m.p. 100°–100.5° C.).

Into a 2 liter 3-necked flask equipped with a mechanical stirrer and reflux condenser were added 320 g (1.6 mol) 3-(trifluoromethyl)glutaric acid and 775 ml acetic anhydride. The solution was refluxed for 2.5 hours and allowed to cool to room temperature. The majority of the acetic anhydride was removed in vacuo (80° C.) to afford a brown solid which was dissolved in 800 ml of CHCl$_3$ on a steam bath. Following the addition of 200 ml hexanes, a white precipitate began to form. Further crystallization was induced by storage in a refrigerator. The white flocculent solid was filtered and oven dried (50° C., 30 mm Hg) to afford 261 g (89% yield) of the desired product, m.p. 88°–91° C.

EXAMPLE 1: N-(4'-chloro-2'-fluoro-5'-proparglyoxyphenyl)-3-(trifluoromethyl)glutaramic acid Into a 1 liter three-necked round-bottomed flask equipped with overhead stirrer, dropping funnel, thermometer and nitrogen (N$_2$) inlet were placed 3-(trifluoromethyl)glutaric anhydride (18.2 g, 0.100 mol) and methylene chloride (CH$_2$Cl$_2$) (250 ml). The mixture was stirred to homogeneity and a solution of 4-chloro-2-fluoro-5-propargyloxyaniline (19.9 g, 0.100 mol) in CH$_2$Cl$_2$ (50 ml) was added dropwise over 10 minutes to give a clear solution. The mixture was stirred overnight at ambient temperature, during which time a thick white precipitate was formed.

In the morning, the reaction mixture was vacuum filtered and washed sparingly with CH$_2$Cl$_2$ to provide the glutaramic acid as a white solid, 36.6 g (96% yield), m.p. 140°–2° C.

EXAMPLE 2: N-(4'-chloro-2'-fluoro-5'-propargyloxyphenyl)-3-(trifluoromethyl)glutarimide (Compound 10)

Into a 500 ml, three-necked round-bottomed flask equipped with a magnetic stir bar, condenser, thermometer and nitrogen inlet adapter were placed N-(4'-chloro-2'-fluoro-5'-propargyloxyphenyl)-3-(trifluoromethyl) glutaramic acid (13.1 g, 0.034 mol), acetic anhydride (150 ml) and sodium acetate (0.45 g). The mixture was stirred and heated to 95° C. overnight. Volatile components were removed by distillation using a shortpath stillhead at a head temperature less than 50° C. (1–5 mm Hg). The residue was dissolved in EtOAc (150 ml) and washed (1×100 ml saturated aqueous sodium bicarbonate (NaHCO$_3$), 1×100 ml water, 1×100 ml brine), dried (MgSO$_4$), filtered and evaporated in vacuo to a brown oil. Drying in vacuo at 50° C. provided a light brown solid (9.8 g, 79% yield, m.p. 80°–82° C.). Recrystallization from methanol/water yielded the glutarimide as a tan solid, m.p. 88°–91° C.

Using the same procedures as described in Example 1 and Example 2, Compounds 1–9, 11, 16–18, 20, 21, 23–28, 33, 39–41, 50, 51, 56, 57, 59–62, 64, 65, 71, 72, 79–83, 86, 92, 94, 95, 99, 106–109, 115, 119, 120, 125, 132, 144, 152, 160, 180, 185, 191, 192, 203, 206, 207, 209, 212, 214, 223, 224, 228, 229, 241 and 275 as defined in Tables I, II and IV were prepared except the aniline or amine compound (Formula II) was: 4-chloro-2-fluoro-5-methoxyaniline, 4-chloro-2-fluoro-5-ethoxyaniline, 4-chloro-2-fluoro-5-n-propyloxyaniline, 4-chloro-2-fluoro-5-n-butyloxyaniline, 4-chloro-2-fluoro-5-isopropyloxyaniline, 4-chloro-2-fluoro-5-s-butyloxyaniline, 4-chloro-2-fluoro-5-isobutyloxyaniline, 4-chloro-2-fluoro-5-hydroxyaniline, 4-chloro-2-fluoro-5-allyloxyaniline, 4-chloro-2-fluoro-5-cyanomethoxyaniline, 2,4,6-trifluoroaniline, 4-bromo-2-fluoroaniline, 2,4-difluoroaniline, 3,4-dichloroaniline, 4-bromo-3-(trifluoromethyl)aniline, p-toluidine, 4-chloro-3-propargyloxyaniline, 2,4-dichloro-5-propargyloxyaniline, 5-amino-2-chloropyridine, 4-chloro-2-fluorobenzylamine, 4-chlorobenzylamine, 2-amino-5-chlorobenzonitrile, 4-(methylthio)aniline, 4-chloro-2-fluoro-5-(isopropylthio) aniline, 4-chloro-2-fluoro-5-[(isopropyloxycarbonyl) methylthio]aniline, isopropyl 5-amino-2-chloro-4-fluorobenzoate, 4-chloro-2-fluoro-5-[(methoxycarbonyl) methylthio]aniline, 4-chloro-2-fluoro-5-[(carboxy) methylthio]aniline, 5-amino-2-chloro-4-fluorothiophenol, 4-chloro-2-fluoro-5-(methylthio)aniline, methyl 5-amino-2-chloro-4-fluorobenzoate, 5-amino-2-chloro-4-fluorobenzoic acid, 4-chlorophenoxyamine, 3-methoxycarbonyl-4-nitrophenoxyamine, ethyl 5-amino-2-chloro-4-fluorobenzoate, n-propyl 5-amino-2-chloro-4-fluorobenzoate, 4-chloro-2-fluoro-5-(hydroxymethyl) aniline, isopropyl 5-amino-2,4-dichlorobenzoate, 4-chloro-2-fluoro-5-(methoxymethyl)aniline, 4-chloro-2-fluoro-5-(isopropyloxymethyl)aniline, 4-chloro-2-fluoro-5-(propargyloxymethyl)aniline, 6-aminoindazole, 5-amino-2-chloro-4-fluorotoluene, 5-amino-2-chloro-4-fluorobenzaldehyde, 3-(propargyloxy)aniline, 3,4-(methylenedioxy)aniline, 1,4-benzodioxan-6-amine, 5-amino-2-methylbenzothiazole, 4-chloro-2-fluoro-5-(isopropylthiomethyl)aniline, 4-chloro-2-fluoro-5-(ethylthiomethyl)aniline, 4-chloro-2-fluoro-5-(phenoxymethyl)aniline, 4-chloro-2-fluoro-5-(phenylthiomethyl)aniline, 4-chloro-2-fluoro-5-[(1-ethoxycarbonyl)ethoxymethyl]aniline, 4-chloro-2-fluoro-5-[(3-butynyl-2-oxy)methyl]aniline, 4-chloro-2-fluoro-5-(methoxyethoxy)aniline, isopropyl 3-amino-4-fluorobenzoate, 4-chloro-2,6-difluoroaniline, 4-cyano-2-fluoroaniline, 5-amino-2-chloro-4-fluoroacetophenone, 6-amino-3,4-benzocoumarin, 4-(trifluoromethoxy)aniline, 4-nitroaniline, 4-(trifluoromethyl)aniline, 4-chloro-5-cyclopentyloxy-2-fluoroaniline, 4-chloro-2-fluoro-5-(isobutylthio)aniline, isopropyl 5-amino-2-bromo-4-fluorobenzoate, isopropyl 5-amino-2-chlorobenzoate, 2,4,5- trifluoroaniline, 2,4-difluoro-5-propargyloxyaniline, 3-chloro-4-methylaniline, isopropyl 5-amino-2,4-difluorobenzoate, 4-bromo-2-fluoro-5-propargyloxyaniline, isopropyl 5-amino- 4-fluoro-2-(trifluoromethyl)benzoate, 2-fluoro-4,5-dimethoxyaniline or 4-chloro-5-(2-chloroallyloxy)-2-fluoroaniline.

In addition, the procedures of Examples 1 and 2 were used to prepare Compounds 30, 35, 38, 43–49, 91, 201, and 237 as described in Tables I, II and III except the appropriate glutaric anhydride of Formula III, i.e., 3-methylglutaric anhydride, 3-ethylglutaric anhydride, 3,3-dimethylglutaric anhydride, 3-(fluoromethyl)glutaric anhydride, 3-(difluoromethyl)glutaric anhydride, 3-(pentafluoroethyl) glutaric anhydride, 3-isopropylglutaric anhydride, 3-phenylglutaric anhydride or homophthalic anhydride, was reacted with an anilino compound (Formula II): 4-chloro-2-fluoro-5-isopropyloxyaniline, 4-chloro-2-fluoro-5-propargyloxyaniline, 4-bromo-2-fluoroaniline, isopropyl 5-amino-2-chloro-4-fluorobenzoate or 5-amino-2-chloropyridine.

EXAMPLE 3: N-(4'-chloro-2'-fluoro-5'-(methoxymethoxy)phenyl)-3-(trifluoromethyl) glutaramide (Compound 12)

a. 4-chloro-2-fluoro-5-(methoxymethoxy)nitrobenzene

To 1.12 g (5.9 mmol) of 2-chloro-4-fluoro-5-nitrophenol in 100 ml of $CH_2Cl_2$ was added 2 ml of dimethoxymethane followed by 7.48 g (53 mmol) of phosphorous pentoxide. The reaction was stirred at room temperature for 3 hours after which time an additional 100 ml of $CH_2Cl_2$ was added. The reaction was poured onto 200 ml of ice and the resulting layers were separated. The aqueous phase was extracted once more with $CH_2Cl_2$ (1×100 ml) and the combined organic phases were washed with water (2×100 ml), dried over $MgSO_4$ and concentrated to afford 1.16 g (95% yield) of a pale yellow solid 4-chloro-2-fluoro-5-(methoxymethoxy)nitrobenzene.

The nitrobenzene intermediate was converted to the corresponding aniline using iron and acetic acid as described in Example 13c. The aniline was converted to Compound 12 of Table I using the procedures described in Examples 1 and 2.

EXAMPLE 4: N-(4'-chloro-2'-fluoro-5'-(benzenesulphonyloxy)phenyl)-3-(trifluoromethyl) glutarimide (Compound 13)

To a solution of N-(4'-chloro-2'-fluoro-5'-hydroxyphenyl)- 3-(trifluoromethyl)glutarimide (1.64 g, 5.05 mmol, Compound 19) in about 20 ml of methylene chloride was added via syringe nearly 2.5 eq. of pyridine (1 ml) which had been freshly distilled from $CaH_2$. Then a solution of benzenesulfonyl chloride (0.64 ml, 5.0 mmol) in 4.5 ml of methylene chloride was slowly added dropwise to the reaction mixture with ice bath cooling. The reaction mixture was allowed to warm to room temperature and stirred for 12 hours. Then there was added 0.17 g of additional glutarimide and the reaction mixture was stirred at room temperature for an additional 12 hours. The reaction mixture was poured into 50 ml of water and the layers were separated. The organic layer was evaporated in vacuo and the residue was dried in the vacuum oven (20–50 Torr, 50° C.). The resulting brown solid was rinsed with approximately 5 ml of methylene chloride and suction filtered to yield 1.9 g (82% yield) of the desired product as an off-white powder (m.p. 214°–215° C.).

Using substantially the procedure described in this example, Compound 190 was prepared except ethanesulfonyl chloride was used in place of benzenesulfonyl chloride.

EXAMPLE 5: N-(4'-chloro-2'-fluoro-5'-isopropyloxyphenyl)-4-(trifluoromethyl)-2-piperidone (Compound 14)

a. N-(4'-chloro-2'-fluoro-5'-isopropyloxyphenyl)-5-hydroxy-3-(trifluoromethyl)pentanamide To a solution of N-(4'-chloro-2'-fluoro-5'-isopropyloxyphenyl)-3-(trifluoromethyl)glutaramic acid (4.32 g, 11.4 mmol) in 20 ml of tetrahydrofuran, (freshly distilled from sodium/benzophenone) was slowly added 10M borane-methyl sulfide complex (1.18 ml) via syringe. The temperature was maintained at 10°–20° C. with an ice bath while vigorous bubbling was evident. The mixture was allowed to warm slowly to room temperature and stirred 150 hrs while kept under nitrogen, heated to 55° C. for 6 hours, then cooled to room temperature and allowed to stand for 16 hours. The flask was cooled in an ice/water bath, then 7 ml of methanol (MeOH) were added slowly via addition funnel. The reaction mixture became too thick to continue stirring. It was allowed to warm slowly to room temperature, when the stir bar was again able to stir the mixture. The MeOH and THF were removed in vacuo (20–50 Torr) and the residue was flash chromatographed (2"×7" column, 3:1 hexanes/ethyl acetate, 75 ml fractions). Fractions 18–45 were combined and the solvent was removed in vacuo. The residue was dried in vacuo at 50° C. to yield 1.66 g (39% yield) of the pentanamide as a nearly colorless oil.

b. N-(4'-chloro-2'-fluoro-5'-isopropyloxyphenyl)-5-chloro-3-(trifluoromethyl)pentanamide To a solution of N-(4'-chloro-2'-fluoro-5'-isopropyloxyphenyl)-5-hydroxy- 3-(trifluoromethyl) pentanamide (1.2 g, 3.2 mmol) in 100 ml methylene chloride, was added thionyl chloride (0.24 ml) in one portion via pipette. The solution turned brown. It was heated to 40°–50° C. for about 7 hours, kept at room temperature for 64 hours, heated to 40° C. for 3 hours, then stirred at room temperature for 18 hours. Then additional thionyl chloride (0.1 ml) was added and heating to 40° C. was resumed for about 4 hours. The reaction mixture was cooled to room temperature and the solvent was removed in vacuo. The residue was dried in vacuo (50° C.) and the resulting golden brown, semi-solid mixture was purified via flash chromatography (20 ml fractions, 2'×7' column, 1:9 ethyl acetate/hexanes) to yield a brown solid, m.p. of 57°–63° C.

c. N-(4'-chloro-2'-fluoro-5'-isopropyloxyphenyl)-4-(trifluoromethyl)-2-piperidone To a tetrahydrofuran (16 ml) solution of 1.4 g (3.6 mmol) of N-(4'-chloro-2'-fluoro-5'-isopropyloxyphenyl)-5-chloro-3-(trifluoromethyl)pentanamide were added 16 ml water and 2 ml 50% NaOH (aq). The mixture was heated to 50° C. while stirring vigorously. After 6 hours the reaction was allowed to cool to room temperature, stirring was stopped and the aqueous layer was removed. The organic layer was evaporated in vacuo, then the residue was taken up in ether (50 ml), washed with water (2×50 ml) and then brine. The original aqueous layer was extracted with a second 50 ml portion of ether, the combined organic layers were washed with brine (50 ml) and dried ($MgSO_4$). The solvent was removed in vacuo to yield 1.3 g. of a brown solid which was recrystallized from hexanes to yield 0.81 g (64% yield) of a brown solid (m.p. 98°–102° C.).

EXAMPLE 6: N-(4'-chloro-2'-fluoro-5'-propargyloxyphenyl)-4-(trifluoromethyl)piperidine (Compound 15)

Into a three-necked round-bottomed flask were placed 0.56 g (15 mmol) lithium aluminum hydride and 60 ml tetrahydrofuran. A thimble containing 3.60 g (10.0 mmol) of N-(4'-chloro-2'-fluoro-5'-propargyloxyphenyl)-3-(trifluoromethyl)glutarimide was placed in a Soxhlet extractor and attached to the reaction flask. The oil bath was heated to 85° C. and 11 ml THF and 25 ml ether were added. After six hours the majority of the glutarimide had been extracted into the reaction mixture producing a grey solid in the reaction flask which prevented stirring. The reaction mixture was allowed to cool to room temperature. Water (0.56 ml) was added slowly followed by 15% NaOH (0.56 ml). Then additional water (1.68 ml) was added in order to precipitate lithium salts. The mixture was suction filtered and the solid was rinsed with ether. The filtrate was evaporated in vacuo to yield 3.4 g of a brown oil. The oil was chromatographed (silica gel, 3:1 hexanes/methylene chloride) to yield 100 mg (3% yield) of the desired product as an oil.

EXAMPLE 7: N-(4'-chloro-2'-fluoro-5'-hydroxyphenyl)-3-(trifluoromethyl)glutarimide (Compound 19)

a. N-(4'-chloro-2'-fluoro-5'-hydroxyphenyl)-3-(trifluoromethyl)glutaramic acid

Into a 1 liter, three-necked round-bottomed flask equipped with a magnetic stir bar, thermometer, dropping funnel, condenser and $N_2$ inlet were placed 4-chloro-2-fluoro-5-hydroxyaniline (25.7 g, 0.159 mol), water (24 ml), acetic acid (8.4 ml) and tetrahydrofuran (THF) (48 ml). The mixture was stirred to homogeneity, then heated to 40° C. and a solution of 3-(trifluoromethyl)glutaric anhydride (34.8 g, 0.191 mol) in THF (60 ml) was added drop wise via an addition funnel and an exotherm of about 3°–4° C. was noted. The resulting mixture was heated to 50° C. for three hours then cooled to ambient temperature.

The reaction mixture was poured onto 600 ml of ice. When the ice melted, the solid was isolated via suction filtration through a coarse sintered glass funnel. The solid was washed well with water and dried in vacuo at 50° C. to yield the glutaramic acid as a grey solid (51.91 g, 95% yield, m.p. 171°–174° C.).

b. N-(4'-chloro-2'-fluoro-5'-hydroxyphenyl)-3-(trifluoromethyl)glutarimide

Into a 250 ml three-necked round-bottomed flask equipped with stir bar, $N_2$ inlet and rubber septa were placed N-(4'-chloro-2'-fluoro-5'-hydroxyphenyl)-3-(trifluoromethyl)glutaramic acid (9.51 g, 24 mmol) and EtOAc (75 ml). The mixture was stirred to homogeneity and thionyl chloride (99+%, 3.87 ml, 2 eq) was added via syringe, followed by 0.25 equivalent of anhydrous N,N-dimethylformamide. The reaction was heated to about 80° C. for approximately 6 hours, and then allowed to stand overnight at room temperature.

The reaction mixture was poured into 125 ml water and was extracted twice with a total of 100 ml of EtOAc. The organic layers were combined, then washed two times with 100 ml of water and once with 50 ml of brine. The organic layer was separated, dried with $MgSO_4$, evaporated under reduced pressure, and dried in vacuo (20–50 Torr, 50° C.). The residue solidified on sitting to yield 8.6 g (99% yield) of the glutarimide as a dark brown solid, m.p. 112°–114° C.

Using the same procedure as used in this example, Compound 58 described in Table I above was also prepared except the anilino compound (Formula II) was 5-amino-2-chloro-4-fluorothiophenol.

EXAMPLE 8: N-(4'-bromophenyl)-3-(trifluoromethyl)glutarimide (Compound 22)

Into a 50 ml 1-necked, round-bottomed flask containing a stir bar were placed 2.50 g (7.96 mmol) N-(4'-bromophenyl)-3-(trifluoromethyl)glutaramic acid (prepared as described in Example 1 from the appropriate aniline and glutaric anhydride) and acetyl chloride (15 ml). The mixture was heated to reflux for 6 hours resulting in a clear, light grey solution. The acetyl chloride was removed via atmospheric distillation through a short path distillation head. The resulting light grey crystalline solid was triturated with hexanes, filtered and washed with hexanes to yield an off-white crystalline solid which was dried in vacuo at 50° C. to yield 2.10 g (89% yield) of product, m.p. 163°–4° C.

Using the same procedure as used in this example, Compounds 29, 34, 37, 42, 63, 66, 68, 69 and 70 described in Tables I and II were also prepared.

EXAMPLE 9: N-(4'-fluorophenyl)-3-methylthioglutarimide (Compound 36)

A mixture of 1.02 g (4.68 mmol) of N-(4'-fluorophenol)-3-methylglutarimide (Compound 66), 0.88 g (2.2 mmol) of 2,4-bis(4-methoxyphenyl)-1,3-dithia-2,4-diphosphetane-2,4-disulfide (known as Lawesson's Reagent), and 6 ml of hexamethylphosphoramide in a 50 ml round-bottomed flask was warmed to 95°–100° C. for 21 hours. An additional 1.05 g (2.5 mmol) of Lawesson's Reagent were added and heating to 100° C. was continued for an additional 30 hours. The mixture was allowed to cool to room temperature and water (50 ml) was added. The mixture was extracted with ether (4×50 ml). The organic portions were combined, dried over $MgSO_4$ and the solvent was removed in vacuo. The resulting 2 g of orange oil were purified via flash chromatography (silica gel, 1:1 hexanes/methylene chloride) to yield 300 mg (28% yield) of yellow oil which solidified to a solid: m.p. 84.5°–87.5° C.

EXAMPLE 10: N-[4'-chloro-2'-fluoro-5'-[(phenylthio)methoxy]-phenyl]-3-(trifluoromethyl)glutarimide (Compound 52)

While kept under $N_2$, 0.15 g (3.7 mmol, 60% dispersion in oil) sodium hydride was washed with pentanes (2×0.5 ml), then suspended in 2 ml of dry THF (fleshly distilled from sodium/benzophenone). To the suspension, cooled in an ice bath, were added 1.1 g (3.4 mmol) of N-(4'-chloro-2'-fluoro-5'-hydroxyphenyl)-3-(trifluoromethyl)glutarimide (Compound 19) dissolved in 3.5 ml of dry THF (freshly distilled from sodium/benzophenone) and two 1 ml rinses of dry THF. The reaction was then allowed to warm to room temperature and stirred for 15 minutes. The flask was again cooled in an ice bath while a solution of chloromethyl phenyl sulfide (0.46 ml, 0.54 g, 3.4 mmol) in 3 ml dry THF was added dropwise. The reaction mixture was allowed to warm slowly to room temperature and stirred for about 24 hours, then warmed to 50° C. for 54 hours. The THF was evaporated in vacuo (2–10 Torr) and the reaction mixture was taken up in 12 ml anhydrous dimethylformamide. The reaction was heated to 100° C. for 8 hours then cooled to room temperature. The reaction mixture was suction filtered through a short pad of neutral alumina and rinsed with 30 ml EtOAc. The filtrate was evaporated in vacuo and the residue was dried in the vacuum oven for 12 hours (20–50 Torr, 50° C.). The resulting oil was vacuum distilled (2–10 Torr, 70° C.). The residue was chromatographed (silica gel, 1:1 hexanes/methylene chloride) to yield 350 mg (23% yield) of the desired product as a white solid, m.p. 108°–109.5° C.

Using the procedure as used in this example, Compounds 53, 54, 55, 73, and 76 described in Table I were also prepared except the appropriately substituted alkyl halide (eg., benzyl chloride for Compound 73) was used in place of the chloromethyl phenyl sulfide.

EXAMPLE 11: N-(4'-chlorophenyl)-3-methylglutarimide (Compound 67)

Combined in a 500 ml one-necked round-bottomed flask containing a stir bar were 3-methylglutaric anhydride (6.41 g, 0.05 mol), p-chloroaniline (6.39 g, 0.05 mol) and tetrahydrofuran (50 ml). The mixture was stirred to homogeneity and had a delayed (about 5 min.) mild exotherm. The pale yellow solution was allowed to stand overnight.

The mixture was evaporated in vacuo, then dried under vacuum of about 2–10 Torr with additional heat, to give a tan solid. The solid was dried overnight in a vacuum oven to yield N-(4'-chlorophenyl)-3-methylglutaramic acid as a tan solid (12.72 g, 99.4%, m.p. 116°–118° C.).

The glutaramic acid was treated as described in Example 8 to yield N-(4'-chlorophenyl)-3-methylglutarimide (96% yield, m.p. 163°–164° C.).

Using the procedure as used in this example, Compounds 31 and 32 described in Table I were also prepared.

EXAMPLE 12: N-[5'-(2-methylpropyloxycarbonyl)-4'-chloro-2'-fluorophenyl]-3-(trifluoromethyl)glutarimide (Compound 75)

a. N-(5'-chlorocarbonyl-4'-chloro-2'-fluorophenyl)-3-(trifluoromethyl)glutarimide To a mixture of N-(5'-carboxy-4'-chloro-2'-fluorophenyl)-3-(trifluoromethyl)glutarimide (Compound 62) (3.0 g, 8.5 mmol) and 35 ml toluene was added thionyl chloride (0.80 ml, 1.3 g, 1.1 mmol) followed by 2 drops of N,N-dimethylformamide and the suspension was heated to 90° C. for two hours. The resulting clear, orange solution was cooled to room temperature and the solvents were removed in vacuo (1 mm Hg). The resulting N-(5'-chlorocarbonyl-4'-chloro-2'-fluorophenyl)-3-(trifluoromethyl)glutarimide, a dark semisolid, could be used without further purification.

b. N-[5'-(2-methylpropyloxycarbonyl)-4'-chloro-2'-fluorophenyl]-3-(trifluoromethyl)glutarimide A mixture of N-(5'-chlorocarbonyl-4'-chloro-2'-fluorophenyl)-3-(trifluoromethyl)glutarimide (3.1 g, 8.3 mmol) and 20 ml THF was cooled to 0°–10° C. and 2-methylpropanol (0.80 ml, 0.64 g, 8.6 mmol) was added followed by triethylamine (1.2 ml, 0.86 g, 8.5 mmol). A white precipitate began to form as the reaction mixture was allowed to warm to room temperature. The suspension was stirred at room temperature overnight, forming a thick white slurry. The reaction mixture was partitioned between water (50 ml) and ethyl acetate (50 ml) and the layers were separated. The aqueous phase was extracted with ethyl acetate (3×25 ml) and the combined organic layers were washed (1×25 ml sat'd NaHCO$_3$, 1×25 ml brine) and dried over MgSO$_4$. Concentration afforded 3.1 g of an orange-brown solid which was passed through a silica gel column (100 g) with 50% ethyl acetate/hexanes. Recrystallization from methanol/water yielded 2.8 g (82% yield from the carboxylic acid) of the expected product as a tan solid, m.p. 82°–85° C.

Using the same procedure as used in this example, Compounds 74, 77, 78, 100–104, 110–114, 116–118, 127, 130, 133, 135, 161–164, 194, 195, 197, 199, 215, 218–221 and 242 described in Table I were also prepared except the appropriately substituted alcohol, thiol, oxime, oximidate, amine or amine hydrochloride (eg. isopropylamine for Compound 78) was used in place of the 2-methylpropanol.

EXAMPLE 13: 4-propargyl-6-(N-(3-(trifluoromethyl)glutarimido))-2H-1,4-benzoxazin-3(4H)-one (Compound 85)

a. 6-nitro-2H-1,4-benzoxazin-3(4H)-one

To a mixture of 10.6 g (182 mmol) of potassium fluoride and 55 ml of anhydrous dimethylformamide was added 7.76 ml (72 mmol) of ethyl bromoacetate and the reaction mixture was stirred at room temperature for 15 minutes. Then 10.79 g (70.0 mmol) of 2-amino-4-nitrophenol was added and the reaction mixture was heated to 55° C. for 6 hours. The reaction mixture was cooled slowly to room temperature, stirred for 12 hours and poured onto 300 ml ice. The solid which formed was filtered off, washed with water and dried (20–50 Torr, 50° C., 16 hrs). The resulting orange solid was taken up in 100 ml EtOAc and 100 ml H$_2$O. The aqueous layer was extracted with EtOAc (2×100 ml). The organic layers were then combined and washed with water (3×150 ml) and 10% HCl and dried (MgSO$_4$). The solvent was removed in vacuo and the resulting solid was recrystallized from ethylene dichloride to yield 3.6 g (27% yield) of 6-nitro-2H-1,4-benzoxazin-3(4H)-one as an orange solid, m.p. 221°–223° C.

b. 6-nitro-4-propargyl-2H-1,4-benzoxazin-3(4H)-one

While kept under N$_2$, 0.81 g (20 mmol) of sodium hydride (60% dispersion in oil) was washed with 3 ml of pentanes and suspended in 20 ml of anhydrous dimethylformamide. While cooling with an ice/brine bath, 3.59 g (18.5 mmol) of 6-nitro-2H-1,4-benzoxazin-3(4H)-one was added through a dry powder funnel (exotherm of about 5° C.). An additional 10 ml of DMF was added and the mixture was stirred at 0° C. for 30 minutes. There was then added 2.06 ml (18.5 mmol) of an 80% solution of propargyl bromide in toluene and the mixture was stirred at room temperature for 12 hrs. The reaction mixture was poured into 50 ml of water and extracted with EtOAc (2×50 ml). The organic layers were combined, washed with water (2×50 ml) and dried (MgSO$_4$). The solvent was removed in vacuo to yield 6-nitro-4-propargyl-2H-1,4-benzoxazin-3(4H)-one as a yellow solid, 4 g (93% yield).

c. 6-amino-4-propargyl-2H-1,4-benzoxazin-3(4H)-one

To a slurry of 5.1 g (91 mmol) of iron powder in 42.5 ml of 5% aqueous acetic acid was added dropwise a solution of 4 g (17 mmol) of 6-nitro-4-propargyl-2H-1,4-benzoxazin-3 (4H)-one dissolved in 42.5 ml of glacial acetic acid and 42.5 ml of EtOAc. The reaction mixture was heated to gentle reflux for 1 hour then cooled to room temperature. The iron was removed by suction filtration. EtOAc (50 ml) was added to the filtrate and the layers were separated. The aqueous phase was extracted with EtOAc (2×50 ml) and the organic layers were combined, washed with saturated aqueous sodium bicarbonate solution (100), and dried (MgSO$_4$). The solvent was removed in vacuo to yield a thin brown oil which was taken up in 50 ml of water and reextracted with EtOAc (3×50 ml). The organic layers were combined, washed with water (2×50 ml) and then dried (MgSO$_4$). The solvent was removed in vacuo to yield 2.55 g (75% yield) of 6-amino-4-propargyl-2H-1,4-benzoxazin-3(4H)-one, a dark brown solid, m.p. 136°–140° C.

The 6-amino-4-propargyl-2H-1,4-benzoxazin-3(4H)-one was reacted with 3-(trifluoromethyl)glutaric anhydride as described in Examples 1 and 2 to yield the desired product, m.p. 203°–204.5° C.

Using the same procedure as used in this example, Compounds 84, 90 and 171 described in Tables III and IV were also prepared except methyl 2-chloropropionate was used in place of ethyl bromoacetate for Compound 84; phosgene in ethyl acetate was used to react with the 2-amino-4-nitrophenol for Compound 90; and 3-methylglutaric anhydride was used in place of 3-(trifluoromethyl)glutaric anhydride for Compound 171.

Using the same procedure as used in parts b and c of this example, Compounds 87, 123, 153, and 170 were prepared starting from 6-nitroindole, 6-nitroindoline and 6-nitroindazole.

EXAMPLE 14: 7-fluoro-2-methyl-4-propargyl-6-(N-(3-(trifluoromethyl)glutaramido))-2H-1,4-benzoxazin-3(4H)-one (Compound 88)

a. 2-(3'-fluorophenoxy)propionic acid

To a solution of m-fluorophenol (24.2 g, 0.22 mol) in 79.2 ml of 2.5% aqueous sodium hydroxide heated to 45° C. with an oil bath was added 29.5 ml (0.26 mol) methyl 2-chloropropionate. The reaction mixture was heated to 80° C. for 17 hours and then allowed to cool. When the temperature reached about 40° C., concentrated HCl (25 ml) was added and the reaction mixture was allowed to cool to room temperature. The reaction mixture was extracted twice with 100 ml ethyl ether. The organic layers were combined and washed with 200 ml of 1.5M aqueous sodium carbonate. The aqueous layer was separated and acidified to pH 1, by pH test paper, by adding concentrated HCl. The acidified aqueous layer was extracted with 200 ml ethyl ether. The organic layer was separated, dried with $MgSO_4$ and filtered. The solvent was removed in vacuo to yield 17 g (41% yield) of 2-(3'-fluorophenoxy)propionic acid as a yellow solid (m.p. 72.5°–74° C.).

b. 2-(2',4'-dinitro-5'-fluorophenyl)propionic acid

To a solution of 5 g (25 mmol) of 2-(3'-fluorophenoxy) propionic acid in 11.55 ml of concentrated sulfuric acid ($H_2SO_4$) was added slowly via an addition funnel a mixture of 3.59 ml of 70% nitric acid (2.1 eq.) and 3.2 ml of concentrated $H_2SO_4$ with ice bath cooling. The reaction mixture was then allowed to warm slowly to room temperature and stirred for 3 hours. The reaction mixture was poured onto 200 ml of ice water and the resulting solid was collected by filtration and dried (20–50 Torr, 50° C.) for 12 hours to yield 3.6 g (50% yield) of 2-(2',4'-dinitro-5'-fluorophenol)propionic acid, m.p. 141°–142° C.

c. 6-amino-7-fluoro-2-methyl-2H-1,4-benzoxazin-3(4H)-one

To a suspension of 5.05 g (90 mmol) of iron powder in 26.5 ml of 5% aqueous acetic acid was added dropwise a solution of 3.6 g (12.5 mmol) of 2-(2',4'-dinitro-5'-fluorophenyl)propionic acid in 26.5 ml of EtOAc and 26.5 ml of glacial acetic acid. The reaction mixture was heated to a gentle reflux for 1 hour and then allowed to cool to room temperature. The iron was removed by suction filtration through a small pad of Celite® and the filter pad was rinsed with 50 ml of EtOAc. The filtrate was transferred to a separatory funnel and the phases were separated. The aqueous layer was extracted with EtOAc (3×50 ml) and the combined organic phases were washed with sodium bicarbonate (2×50 ml), dried over $MgSO_4$ and filtered. The solvent was removed from the filtrate in vacuo to yield 1.5 g (61% yield) of 6-amino-7-fluoro-2-methyl-2H-1,4-benzoxazin-3(4H)-one as a brown solid, m.p. 208°–211° C.

d. 6-amino-7-fluoro-2-methyl-4-propargyl-2H-1,4-benzoxazin-3(4H)-one

While kept under $N_2$, 0.30 g (7.4 mmol) of sodium hydride (60% dispersion in oil) was washed with 1 ml pentanes and then suspended in 2 ml anhydrous dimethylformamide. A solution of 1.36 g (6.9 mmol) of 6-amino-7-fluoro-2-methyl-2H-1,4-benzoxazin-3(4H)-one in 10 ml of dimethylformamide was added to the sodium hydride slurry slowly by syringe with ice cooling and the reaction mixture was stirred at room temperature for 0.5 hr. There was then added 0.77 ml (8.6 mmol) of propargyl bromide by syringe with ice bath cooling. The reaction mixture was allowed to warm to room temperature, stirred for 84 hours and then poured into 50 ml of water. The resulting mixture was extracted with EtOAc (2×50 ml) and the organic layers were combined and washed with water (3×50 ml), dried over $MgSO_4$ and filtered. The solvent was removed in vacuo to yield a golden solid which was recrystallized from chloroform to yield 0.66 g of 6-amino-7-fluoro-2-methyl-4-propargyl-2H-1,4-benzoxazin-3(4H)-one as a brown solid, m.p. 142°–145° C.

The 6-amino-7-fluoro-2-methyl-4-propargyl-2H-1,4-benzoxazin-3(4H)-one was reacted with 3-(trifluoromethyl) glutaric anhydride as described in Examples 1 and 2 to obtain the desired product, m.p. 147°–148° C.

Using the same procedures as used in this example, Compounds 89, 97, 137–139, 155, 182, 208, 210, 226, 230 and 233 described in Table III were also prepared except that the procedure of Example 17a was used in place of part a and the appropriately substituted alkyl halide or mesylate (eg. allyl bromide for Compound 97) was used in place of propargyl bromide.

Using the same procedure as used in this example, Compound 235 was prepared except the procedure of Example 17a was used in place of part a and ethyl 2-bromobutyrate was used in place of methyl bromoacetate.

This procedure was also used to prepare Compound 145 except that 3-methylglutaric anhydride was used in place of 3-(trifluoromethyl)glutaric anhydride.

EXAMPLE 15: N-[4'-chloro-2'-fluoro-5'-(O-methyloximyl)phenyl]-3-trifluoromethyl)glutarimide (Compound 93)

To a suspension of methoxylamine hydrochloride (0.55 g, 6.6 mmol) in absolute ethanol (10 ml), was added pyridine (0.52 g, 6.6 ml) via pipette. The reaction was stirred for one hour at room temperature then N-(4'-chloro-2'-fluoro-5'-formylphenyl)-3-(trifluoromethyl)glutarimide (2.03 g, 6.0 mmol) (Compound 94) was added as a solid. Additional ethanol (31 ml) was added and the resulting amber solution was stirred under nitrogen overnight. The solvent was removed in vacuo and the residue was partitioned between ethyl acetate and water. The organic phase was washed with 2.5% HCl (1×25 ml), and brine (1×25 ml), then dried over $MgSO_4$. Concentration afforded a tan solid, which was recrystallized from $MeOH/H_2O$ to yield the desired glutarimide as tan crystals (1.33 g, 60% yield, m.p. 150.5°–152.5° C.).

Using the same procedure as used in this example, Compounds 150, 156, 158, 159, 168, 186, 187 and 205 described in Table I were also prepared using the appropriate alkoxy amine or alkoxy amine salt in place of methoxylamine hydrochloride.

Using the same procedure as used in this example, Compounds 172–176 and 178 were prepared except N-(4'-chloro-2'-fluoro-5'-acetylphenyl)-3-(trifluoromethyl) glutarimide (Compound 95) was used in place of Compound 94 and was reacted with the appropriate alkoxy amine or alkoxy amine salt.

EXAMPLE 16: 4-propargyl-6-(N-(3-(trifluoromethyl)glutarimido))-2H-1,4-benzthiazin-3(4H)-one (Compound 124)

a. ethyl S-(2,4-dinitrophenyl)mercaptoacetate

Into a 100 ml round-bottomed flask were placed 14.8 g (10 ml, 79.6 mmol) 2,4-dinitrofluorobenzene, THF (20 ml, freshly distilled from sodium benzophenone) and triethylamine (11.1 ml, 79.6 mmol). The reaction was cooled in an ice bath while 9.55 g (8.73 ml, 79.6 mmol) ethyl 2-mercaptoacetate dissolved in THF (10 ml) was added dropwise. The resulting nearly black solution was allowed to warm slowly to room temperature and stirred 18 hours. The reaction mixture was poured onto 150 ml ice and the resulting layers were separated. The aqueous phase was extracted with EtOAc (2×125 ml). The organic layers were combined and washed with water (100 ml), dried over $MgSO_4$ and concentrated to dryness in vacuo to yield 16.9 g of red-brown solid (74.1% yield).

b. 6-amino-2H-1,4-benzthiazin-3(4H)-one

To a suspension of iron powder (15 g, 0.27 mol) in 21.7 ml of 5% aqueous acetic acid was added dropwise via addition funnel, a solution of ethyl S-(2,4-dinitrophenyl) mercaptoacetate (5.91 g, 20.6 mmol) in 20.6 ml glacial acetic acid and 21 ml EtOAc. The reaction mixture was heated to 80° C. for 2 hours, then cooled to room temperature. The iron was removed by suction filtration and the filtrate was extracted with EtOAc (3×75 ml). The combined organic layers were washed once with 100 ml water and twice with 100 ml saturated aqueous sodium bicarbonate, dried ($MgSO_4$) and concentrated to dryness in vacuo to yield 2.3 g of a dark brown solid.

The 6-amino-2H-1,4-benzthiazin-3(4H)-one was alkylated with propargyl bromide as described in Example 13b, then converted to Compound 124 using the procedures described in Examples 1 and 2.

Compound 184 was prepared using the above procedure except that 2,4-dinitro-1,5-difluorobenzene was used in place of 2,4-dinitrofluorobenzene.

EXAMPLE 17

7-fluoro-4-isobutyl-6-N-(3-(trifluoromethyl) glutaramido))-2H-1,4-benzoxazin-3(4H)-one (Compound 128)

a. methyl 5-fluoro-2-nitrophenoxyacetate

To 10 g (63.7 mmol) of 5-fluoro-2-nitrophenol in 100 ml of methyl ethyl ketone was added 10.5 g (76.4 mmol) of finely ground potassium carbonate followed by 10.7 g (70.1 mmol) of methyl bromoacetate. The resulting suspension was refluxed for 6 hours and then stirred at room temperature overnight. During this time it went from a deep red color to pale yellow. The reaction was poured into one liter of water, the layers were separated and the aqueous layer was extracted twice more with EtOAc (2×100 ml). The organics were combined, dried ($Na_2SO_4$), filtered and evaporated to dryness in vacuo to give 13.3 g (91% yield) of methyl 5-fluoro-2-nitrophenoxyacetate as a light yellow solid (m.p. 85°–87° C.).

b. 7-fluoro-2H-1,4-benzoxazin-3(4H)-one

To 500 mg of 5% Pd/C in a Parr bottle was added 100 ml of EtOH followed by 5.0 g (21.8 mmol) of methyl 5-fluoro-2-nitrophenoxyacetate. The flask was placed in a Parr Apparatus, evacuated and then charged with hydrogen. The suspension was then shaken for 2 hours. After evacuating the flask and recharging with nitrogen, the solids were removed by vacuum filtration through Celite®. Since some product does precipitate, the filter cake is repeatedly rinsed with EtOAc (200 ml). The filtrate is refluxed for 4 hours and then evaporated to dryness in vacuo to give the desired material, 7-fluoro-2H-1,4-benzoxazin-3(4H)-one, as a white solid (m.p. 201°–202° C.) in quantitative yield.

c. 7-fluoro-4-isobutyl-2H-1,4-benzoxazin-3(4H)-one

To 3.96 g (99 mmol) of hexanes washed 60% sodium hydride in 150 ml of N,N-dimethylformamide was added portionwise as a solid 15 g (90 mmol) of 7-fluoro-2H-1,4-benzoxazin-3(4H)-one. When the addition was complete the reaction was stirred at room temperature for 10 min, after which time 19.8 g (108 mmol) of isobutyl iodide was added. The reaction was then stirred overnight before quenching into 200 ml of water. The aqueous phase was extracted with EtOAc (2×150 ml) and the combined organics were dried over $Na_2SO_4$, filtered and evaporated in vacuo to give the desired alkylated product, as a yellow oil (13 g, 65% yield).

d. 7-fluoro-4-isobutyl-6-nitro-1,4-benzoxazin-3(4H)-one

To 2.50 g (11.2 mmol) of 7-fluoro-4-isobutyl-2H-1,4-benzoxazin-3(4H)-one in 25 ml of acetic anhydride was added dropwise over 10 min. a solution of 2.5 g (26.9 mmol) of 70% nitric acid in 5 ml of glacial acetic acid. After the addition was complete, the reaction was stirred for 1 hour at room temperature then it was quenched by pouring into 50 ml of ice/water. The resulting white precipitate was collected by vacuum filtration and dried in a vacuum oven at 60° C. overnight to yield 2.71 g (90% yield) of the desired nitrated product, m.p. 108°–110° C.

e. 6-amino-7-fluoro-4-isobutyl-1,4-benzoxazin-3(4H)-one

To 2.82 g (50.5 mmol) of iron powder suspended in 30 ml of 5% glacial acetic acid was added dropwise over 0.5 hour a solution of 2.71 g (10.1 mmol) of 7-fluoro-4-isobutyl-6-nitro-1,4-benzoxazin-3(4H)-one in 60 ml of 1:1 EtOAc/ glacial acetic acid. After addition was complete, the reaction was refluxed for 2 hours then the solids were removed by vacuum filtration. The filtrate was extracted with EtOAc (2×100 ml) and the combined organic layers were washed with $NaHCO_3$ (sat'd, 2×150 ml) and dried over $Na_2SO_4$ before filtering and concentrating (in vacuo) to give 2.32 g (96% yield) of the desired aniline, 6-amino-7-fluoro-4-isobutyl-1,4-benzoxazin-3(4H)-one, as a red semisolid.

The 6-amino-7-fluoro-4-isobutyl-1,4-benzoxazin-3(4H)-one was reacted with 3-(trifluoromethyl)glutaric anhydride as described in Examples 1 and 2 to yield the desired product, m.p. 180°–181° C.

Using the appropriate alkylating agent in place of isobutyl iodide in step c, the above procedures were used to prepare Compounds 96, 98, 122, 126, 129, 131, 134, 143, 146, 149, 165, 166, 189 and 204. Compound 188 was prepared following essentially the same procedure but using the reaction conditions of Example 3a in place of part c.

Compound 238 was prepared using the above procedures except propargyl bromide was used in place of isobutyl iodide and the resulting 6-amino-7-fluoro-4-propargyl-1,4-benzoxazin-3(4H)-one was reacted with 3-(difluoromethyl) glutaric anhydride as described in Examples 1 and 2.

EXAMPLE 18

4-(n-propyl)-6-(N-(3-(trifluoromethyl)glutarimido))-1,4-benzoxazoline (Compound 136)

To a slurry of lithium aluminum hydride (1.2 g, 31.6 mmol) in 100 ml THF (freshly distilled from sodium/ benzophenone), was added dropwise via an addition funnel 6-amino-4-n-propyl-2H-1,4-benzoxazin-3(4H)-one (prepared using the procedure described in Example 13) (1.89 g, 9.16 mmol) dissolved in 60 ml THF. The slow addition produced a gentle reflux. Upon completion of the addition, the reaction was refluxed for 72 hours then cooled to room temperature. Water (1.2 ml) was cautiously added followed by 3.6 ml 15% aqueous NaOH then more water (1.2 ml). After the slight exotherm subsided, the reaction mixture was suction filtered and the solids were washed with 100 ml THF. The filtrate was concentrated to dryness in vacuo to yield 1.43 g (74% yield) of 6-amino-4-n-propyl-1,4-benzoxazoline as a brown oil.

The aniline was reacted as described in Examples 1 and 2 to afford the desired glutarimide.

EXAMPLE 19

N-[5'-(3-butynyloxy)-4'-chloro-2'-fluorophenyl]-3-(trifluoromethyl)glutarimide (Compound 140)

Potassium carbonate (7.8 g, 56 mmol) was added to a solution of 5-amino-2-chloro-4-fluorophenol (3.23 g, 19.9 mmol) in 50 ml methyl ethyl ketone and the reaction mixture was stirred at room temperature for 1 hour. Then 4.2 g (19.9 mmol) 4-phenylsulfonyloxy-1-butyne (prepared from benzenesulfonyl chloride and 3-butyn-1-ol according to known procedure) was added and the reaction mixture was refluxed for 24 hours. The reaction was poured into 50 ml water and the layers were separated. The aqueous layer was extracted with EtOAc (1×50 ml) and the combined organics were washed with $H_2O$ (3×50 ml), dried over $MgSO_4$, and concentrated. The residue was dissolved in 110 ml $CH_2Cl_2$ and filtered through a short pad of silica gel which was repeatedly rinsed with $CH_2Cl_2$ (4×100 ml). The combined organics were concentrated in vacuo to yield 0.95 g (22% yield) of the desired product as a brown oil.

The aniline was reacted with 3-(trifluoromethyl)glutaric anhydride as described in Examples 1 and 2 to yield the desired product, m.p. 89°–91° C.

Using the same procedure as used in this example, Compounds 141, 196, 216, 231, 232, 234 and 236 were prepared except the appropriate alkylating agent (prepared from methanesulfonyl chloride and an alcohol according to known procedures) was used in place of 4-phenylsulfonyloxy-1-butyne.

EXAMPLE 20

7-fluoro-4-methoxycarbonyl-6-(N-(3-(trifluoromethyl)glutarimido))-2H-1,4-benzoxazin-3(4H)-one (Compound 142)

To 0.165 g (4.13 mmol) of sodium hydride (washed with hexanes) in 10 ml DMF was added 1.3 g (3.75 mmol) of 7-fluoro-6-(N-(3-(trifluoromethyl)-glutarimido))-2H-1,4-benzoxazin-3(4H)-one (Compound 138) in 20 ml DMF. The reaction was stirred at room temperature for 10 minutes before 0.425 g (4.50 mmol) of methyl chloroformate was added. The mixture was stirred one hour then poured onto 50 ml ice/water and extracted with EtOAc (2×50 ml). The organic layers were combined, dried over anhydrous $Na_2SO_4$ and evaporated to dryness in vacuo. The residue was chromatographed (silica gel, 1:1 hexanes EtOAc) to yield 0.58 g (38% yield) of the desired compound as a yellow oil.

Compound 121, 179 and 200 were prepared using the same procedure except the appropriate alkylating agent was used in place of methyl chloroformate.

EXAMPLE 21

N-(3-acetamido-4-methoxyphenyl)-3-(trifluoromethyl)glutarimide (Compound 148)

2-Methoxy-5-nitroaniline was purchased and acetylated using $HOAc/Ac_2O$ in $H_2O$/THF according to known procedures to make 2-methoxy-5-nitroacetanilide. This was reduced using catalytic hydrogenation ($PtO_2$, $H_2$, EtOH) to afford 3-acetamido-4-methoxyaniline which was reacted as described in Examples 1 and 2 to yield the desired glutarimide.

EXAMPLE 22

4-methoxymethyl-6-(N-(3-(trifluoromethyl)glutaramido))-2H-1,4-benzoxazin-3(4H)-one (Compound 151)

a. 6-nitro-2H-1,4-benzoxazin-3(4H)-one

To a slurry of 2-amino-4-nitrophenol (10.7 g, 69.4 mmol) in 150 ml of $CH_2Cl_2$ was added 19.37 ml (139 mmol) of triethylamine and the mixture was stirred until homogenous. The reaction flask was then cooled to 0° C. while a solution of chloroacetyl chloride (11.06 ml, 139 mmol) in $CH_2Cl_2$ (50 ml) was added dropwise. The reaction was allowed to warm to room temperature and stirred for 16 hours after which time it was poured onto 250 ml of ice. The resulting white precipitate was collected by vacuum filtration, washed with $CH_2Cl_2$ (25 ml) and dried in a vacuum oven at 50° C. to yield 20.56 g (90% yield) of the desired intermediate product.

To a solution of 7.82 g (25.6 mmol) of N,O-bis-(chloromethylcarbonyl)-2-amino-4-nitrophenol in 25 ml of THF was added 2.67 ml (51.2 mmol) of 50% NaOH and 10 ml of water. The two phase reaction mixture was stirred at room temperature for 16 hours then the solvents were removed in vacuo. The residue was partitioned between $Et_2O$ (100 ml) and water (100 ml) and the layers were separated. The aqueous layer was extracted sequentially with $Et_2O$ (2×100 ml) and EtOAc (2×100 ml) and the combined organic phases were dried over $MgSO_4$ and concentrated in vacuo to give 1.3 g (26% yield) of the desired product (m.p. 223°–228° C.) as a yellow solid.

b. 4-methoxymethyl-6-nitro-2H-1,4-benzoxazin-3(4H)-one

To 0.976 g (5.02 mmol) of 6-nitro-2H-1,4-benzoxazin-3(4H)-one in 100 ml of chloroform was added 2 ml of dimethoxymethane. Phosphorous pentoxide (5 g, 35 mmol) was added portionwise and the reaction mixture was stirred at room temperature for 16 hours. TLC analyses showed the starting material was still present; therefore, additional dimethoxymethane (2 ml) was added along with several batches of phosphorous pentoxide (2×1.2 g and 2.0 g) and chloroform (50 ml). The reaction was stirred for an additional 16 hours then cautiously quenched with water (50 ml). The reaction mixture was slowly neutralized with 50 ml of 1N NaOH during which time an exotherm occurred. When the reaction mixture had cooled to room temperature, the layers were separated and the aqueous phase was extracted with chloroform (2×50 ml). The combined organic phases were washed with water (2×50 ml), dried over $MgSO_4$ and concentrated to afford the desired intermediate product (0.5 g, 42% yield) as a pale yellow solid.

The nitro compound was reduced using the procedure described in Example 13c to yield 6-amino-4-methoxymethyl-2H-1,4-benzoxazin-3-one which was reacted with 3-(trifluoromethyl)glutaric anhydride as described in Examples 1 and 2 to yield the desired product, m.p. 138°–140° C.

Using the procedure as described in this example, except the procedure of 13b was used in place of part b, Compounds 105, 147, 154, 157, 167, 211 and 217 were prepared using the appropriate alkylating agent.

EXAMPLE 23

N-(4'-chloro-5'-cyano-2'-fluorophenyl)-3-(trifluoromethyl)glutarimide (Compound 169)

To 1.07 g (3.03 mmol) of N-[4'-chloro-2'-fluoro-5'-(N'-oximylphenyl)]-3-(trifluoromethyl)glutarimide (Compound 159) in $CH_2Cl_2$ (30 ml) containing 2.0 g anhydrous $MgSO_4$ was added 0.40 g (0.25 ml, 3.36 mmol) of thionyl chloride. The reaction mixture was stirred vigorously for 3 days at room temperature after which time TLC analysis indicated that the starting material was still present. Additional thionyl chloride (0.1 ml) was added and the reaction was refluxed for 3 hours. TLC now showed that all of the starting material had reacted. The $MgSO_4$ was filtered and the solvent was removed in vacuo to leave a pale yellow solid (0.90 g, 89% yield) identified by NMR to be the desired cyano compound, m.p. 210°–212° C.

EXAMPLE 24

N-[5'-(isopropylaminium carboxylate)-4'-chloro-2'-fluorophenyl]-3-(trifluoromethyl)glutarimide (Compound 177)

To N-(5'-carboxy-4'-chloro-2'-fluorophenyl)-3-(trifluoromethyl)glutarimide (Compound 62) (1.3 g, 3.6 mmol) dissolved in 10 ml EtOAc was added 0.31 ml (0.21 g, 3.6 mmol) isopropyl amine. After stirring at room temperature for 15 minutes, a white precipitate formed. The fine powder was filtered and dried in vacuo to afford 0.95 g (75% yield) of the desired salt, m.p. 168°–173° C. (dec).

EXAMPLE 25

N-[5'-(potassium carboxyalte)-4'-chloro-2'-fluorophenyl]-3-(trifluoromethyl)glutarimide (Compound 213)

To a suspension of KH (0.6 g of 35% wt dispersion on mineral oil, washed 2×5 ml hexanes) in 5 ml of THF was added dropwise a solution of N-(5'-carboxy-4'-chloro-2'-fluorophenyl)-3-(trifluoromethyl)glutarimide (Compound 62) (1.8 g, 5.1 mmol) in 20 ml THF. When the hydrogen evolution subsided, the clear solution was stirred for 10 minutes and then filtered to remove remaining particulate matter. Concentration of the filtrate afforded 1.8 g (90% yield) of the desired potassium salt as a white solid, m.p. 133°–143° C.

EXAMPLE 26

N-[3'-(N-methylacetamido)-4'-chlorophenyl]-3-(trifluoromethyl)glutarimide (Compound 183)

a. N-methyl-2-chloro-5-nitroacetanilide

While being kept under $N_2$, 3.12 g (78 mmol, 60% dispersion in oil) sodium hydride was washed with pentanes (2×2.5 ml) and then suspended in 150 ml anhydrous DMF. To the suspension was added 14.0 g (65.1 mmol) 2-chloro-5-nitroacetanilide followed by 50 ml of DMF for rinsing. The reaction was stirred at room temperature for 15 minutes then methyl iodide (20 ml, 45 g, 32 mmol) was added and the reaction was heated to 45° C. for 3 hours and stirred at room temperature for another 85 hours. The reaction mixture was poured into 500 ml water and extracted with 500 ml EtOAc. The organic layer was washed with water (3×200 ml) and brine (1×200 ml), dried ($MgSO_4$) and concentrated in vacuo to yield 13.3 g (89% yield) of N-methyl-2-chloro-5-nitroacetanilide as a yellow solid.

b. N-methyl-4-amino-2-chloroacetanilide

To 300 ml absolute ethanol in a Parr bottle was added 12.55 g (54.9 mmol) N-methyl-2-chloro-5-nitroacetanilide. After bubbling nitrogen through the solution for 15 minutes, 300 mg platinum (IV) oxide was added. The flask was placed in a Parr apparatus and shaken for 20 minutes under a $H_2$ atmosphere. The catalyst was removed by filtration through Celite and the filtrate was concentrated in vacuo to give 10.25 g (94% yield) of the desired aniline as a yellow solid.

The N-methyl-4-amino-2-chloroacetanilide was reacted with 3-(trifluoromethyl)glutaric anhydride as described in Examples 1 and 2 to yield the desired product, m.p. 203°–204° C.

EXAMPLE 27

N-[4'-chloro-2'-fluoro-5'-(1,3-dioxanyl)phenyl]-3-(trifluoromethyl)glutarimide (Compound 193)

To 3.4 g (10 mmol) N-(4'-chloro-2'-fluoro-5'-formylphenyl)-3-(trifluoromethyl)glutarimide (Compound 94) in 110 ml toluene was added 0.94 g (15 mmol) ethylene glycol and a catalytic amount of p-toluenesulfonic acid monohydrate (0.48 g, 2 mmol). The mixture was refluxed for 72 h with removal of water via a Dean-Stark trap. The solvent was removed in vacuo and the residue was partitioned between EtOAc and water. The organics were washed with water and brine, dried over $MgSO_4$, then filtered and concentrated to leave 4.1 g (105% yield) of an oily taffy containing mostly product by NMR analysis. Recrystallization from $Et_2O$ afforded 1.0 g of the 1,3-dioxane as a pale yellow solid, m.p. 158°–161° C.

EXAMPLE 28

N-(5'-isobutylsulfonyl-4'-chloro-2'-fluorophenyl)-3-(trifluoromethyl)glutarimide (Compound 202)

a. 4-chloro-2-fluoro-5-(isobutylthio)acetanilide

Potassium carbonate (26 g, 188 mmol) was added to a solution of 5-acetamido-2-chloro-4-fluorothiophenol (11.35 g, 52.4 mmol) in 50 ml anhydrous DMF and the reaction mixture was stirred at room temperature for 10 minutes. Then 6.63 ml (57.0 mmol) 1-iodo-2-methylpropane was added and the reaction was heated to 50° C. for 18 hours. The reaction was poured into 200 ml water, then suction filtered to isolate a nearly white solid which was dried in vacuo to yield 13.31 g (93% yield) of the alkylated product as an off-white solid.

b. 4-chloro-2-fluoro-5-(isobutylsulfonyl)acetanilide

Meta-chloroperoxybenzoic acid (7.7 g, 36.6 mmol) was added to a solution of 4-chloro-2-fluoro-5-(isobutylthio) acetanilide (4.9 g, 17.8 mmol) in 50 ml $CH_2Cl_2$. After the reaction was stirred at room temperature for 2.5 hours, additional meta-chloroperoxybenzoic acid (4.6 g, 21.9 mmol) was added and the reaction was stirred for an additional 30 minutes before it was poured into 50 ml water. The organic layer was isolated and washed successively with saturated aqueous sodium bicarbonate (aq. NaHCO$_3$) (2×50 ml), water (1×50 ml) and aq. NaHCO$_3$ (2×50 ml). The solvent was removed in vacuo and the residue was dissolved in 100 ml CH$_2$Cl$_2$ then washed with 10% aqueous sodium sulfite (1×100 ml) and aq. NaHCO$_3$ (1×100 ml). The organic layer was concentrated to dryness in vacuo to yield 5.5 g of a yellow solid identified by NMR to contain mostly the desired product. The crude material was used in the next reaction.

c. 4-chloro-2-fluoro-5-(isobutylsulfonyl)aniline

Concentrated hydrochloric acid (16.65 ml, 200 mmol) was added to a slurry of 4-chloro-2-fluoro-5-(isobutylsulfonyl)acetanilide (5.46 g, 17.7 mmol) in water (24.85 ml) and ethanol (19.08 ml). The reaction mixture was refluxed for 2 hours, poured onto 200 ml ice and made strongly basic by the addition of 50% NaOH. The aqueous phase was extracted with Et$_2$O (2×100 ml) and the combined organic layers were washed with water (1×100 ml) and brine (1×100 ml), dried (Na$_2$SO$_4$) and concentrated in vacuo. The brown solid obtained (3.8 g, 81% yield) was shown by NMR to contain the desired aniline as the main component.

The 4-chloro-2-fluoro-5-(isobutylsulfonyl)aniline from above was reacted with 3-(trifluoromethyl)glutaric anhydride as described in Examples 1 and 2 to prepare Compound 202, m.p. 48°–51° C.

EXAMPLE 29

N-(5'-bis-acetamido4'-chloro-2'-fluorophenyl)-3-(trifluoromethyl)glutarimide (Compound 225)

To 100 ml absolute ethanol in a Parr bottle was added 3.21 g (8.61 mmol) N-(4'-chloro-2'-fluoro-5'-nitrophenyl)-3-(trifluoromethyl)glutaramic acid (prepared from 4-chloro-2-fluoro-5-nitroaniline and 3-(trifluoromethyl)glutaric anhydride using the procedure of Example 1). After bubbling nitrogen through the solution for 15 minutes, 100 mg platinum (IV) oxide was added. The flask was placed on a Parr apparatus and shaken for 1 hr under an atmosphere of hydrogen. The solids were removed by filtration through Celite and the filtrate was concentrated to dryness to give 3.1 g (100% yield) of an off-white solid containing N-(5'-amino-4'-chloro-2'-fluorophenyl)-3-(trifluoromethyl)glutaramic acid.

Using the procedure of Example 2, N-(5'-amino-4'-chloro-2'-fluorophenyl)-3-(trifluoromethyl)glutaramic acid was converted to Compound 225, m.p. 164°–160° C.

EXAMPLE 30

N-[4'-chloro-2'-fluoro-5'-(4",4"-dimethyl-2-oxazolin-2-yl)phenyl]-3-(trifluoromethyl)glutarimide (Compound 227)

a. 2-chloro-4-fluoro-5-nitrobenzoyl chloride

To solution of 2-chloro-4-fluoro-5-nitrobenzoic acid (4.0 g, 18 mmol) in 65 ml toluene was added 2 drops of DMF followed by 1.8 ml (25 mmol) thionyl chloride. The mixture was heated to reflux for 18 hr, cooled to ambient temperature and the solvent was removed in vacuo to afford 4.0 g (93% yield) of a white solid identified by IR and NMR as the desired benzoyl chloride. The crude material was used directly in the following procedure.

b. N-(1,1-dimethyl-2-hydroxyethyl)-2-chloro-4-fluoro-5-nitrobenzamide

To a cooled (0° C.) solution of 2-amino-2-methyl-1-propanol (2.4 ml, 2.2 g, 25 mmol) in CH$_2$Cl$_2$ (10 ml), was added dropwise via an addition funnel 3.0 g (12 mmol) 2-chloro-4-fluoro-5-nitrobenzoyl chloride in 20 ml CH$_2$Cl$_2$. Following the addition, the mixture was allowed to warm to room temperature and a white precipitate formed. After 1.5 hr, 10 ml water was added and the mixture was filtered to afford 2.1 g of a pale yellow solid identified by NMR to be the desired product. The filtrate was extracted with EtOAc (3×75 ml) and the combined organic phases were washed with brine, saturated sodium bicarbonate, again with brine and then dried over MgSO$_4$. Concentration gave 1.0 g of additional product (3.1 g, 86% total yield).

c. 2-(2'-chloro-4'-fluoro-5'-nitrophenyl)-4,4-dimethyl-2-oxazoline

To a suspension of N-(1,1-dimethyl-2-hydroxyethyl)-2-chloro-4-fluoro-5-nitrobenzamide (2.0 g, 6.9 mmol) in 30 ml EtOAc was added dropwise 1.6 ml (2.6 g, 22 mmol) thionyl chloride. The resulting clear, yellow solution was stirred at room temperature for 25 minutes during which time a white precipitate formed. The reaction was then treated with 30 ml 10% NaOH causing a slight exotherm as the solids dissolved. The aqueous phase was extracted with EtOAc (3×25 ml) and the combined organics were washed with brine and dried (MgSO$_4$). Concentration afforded 1.85 g (98% yield) of product as a yellow solid.

The 2-(2'-chloro-4'-fluoro-5'-nitrophenyl)-4,4-dimethyl-2-oxazoline was reduced as described in Example 13c to the corresponding aniline which was converted to the glutarimide (Compound 227) using the procedures of Examples 1 and 2.

EXAMPLE 31

6-fluoro-3-n-propyl-5-N-(3-(trifluoromethyl)glutarimido))-1,3-benzoxazalin-2(3H)-one (Compound 181)

a. 2-amino-5-fluorophenol

To 500 mg of 10% palladium on carbon in a Parr bottle containing 50 ml of anhydrous ethanol was added a solution of 10 g (64 mmol) 5-fluoro-2-nitrophenol in 150 ml ethanol. The flask was evacuated, charged with hydrogen and shaken on a Parr apparatus for 1 hour. The catalyst was removed by filtration through Celite® and the filtrate was evaporated to dryness in vacuo to give 7.54 g (93% yield) of a dark solid.

b. 6-fluoro-1,3-benzoxazolin-2(3H)-one

To 5.0 g (39.3 mmol) 2-amino-5-fluorophenol in 150 ml of CH$_2$Cl$_2$ at 0° C. was added 13.4 (98 mmol) of potassium carbonate and 23 g (47 mmol) of 20 wt % phosgene in toluene. After warming to room temperature, the reaction was stirred an additional hour before quenching onto 200 ml ice/water. The layers were separated and the aqueous phase was extracted with EtOAc (1×100 ml) before the organics were combined and dried over Na$_2$SO$_4$. The solvent was removed in vacuo to give 5.76 g (96% yield) of the desired product as determined by $^1$H NMR.

c. 6-fluoro-3-n-propyl-1,3-benzoxazolin-2(3H)-one

To 670 mg (16.74 mmol) of hexanes washed sodium hydride in 20 ml DMF was added a solution of 2.33 g (15.22 mmol) 6-fluoro-1,3-benzoxazolin-2(3H)-one in 40 ml DMF. The reaction was stirred for 10 minutes before 3.11 g (18.3 mmol) 1-iodopropane was added and then stirred for 3 hr at room temperature. After quenching onto 50 ml of ice/water, the aqueous phase was extracted with EtOAc (2×100 ml). The combined organic layers were washed with water (1×100 ml), dried over Na$_2$SO$_4$ and evaporated to dryness in vacuo to give 2.2 g (75% yield) of the alkylated product as a brown solid.

51 d. 6-fluoro-5-nitro-3-n-propyl-1,3-benzoxazolin-2(3H)-one

To 2.0 g (10.3 mmol) 6-fluoro-3-n-propyl-1,3-benzoxazolin-2(3H)-one in 25 ml acetic anhydride was added dropwise a solution of 2.3 g (24.7 mmol) 70% nitric acid in 2 ml glacial acetic acid. After addition was completed, the reaction was stirred at room temperature for 2 hours and then poured onto 50 ml ice/water. The aqueous phase was extracted with EtOAc (2×70 ml) and the combined organics were dried over $Na_2SO_4$ and evaporated to dryness in vacuo to give 1.66 g (67% yield) of the nitrated product as a yellow oil.

The 6-fluoro-5-nitro-3-n-propyl-1,3-benzoxazolin-2(3H)-one prepared above was reduced to the corresponding aniline following the procedure of Example 17e and the aniline was reacted with 3-(trifluoromethyl)glutaric anhydride as described in Examples 1 and 2 to yield the desired product, m.p. 148°–152° C.

EXAMPLE 32

N-(6-fluoro-1-n-propyl-4H-3,1-benzoxazin-2(1H)-one-7-yl)-3-(trifluoromethyl)glutarimide (Compound 198)

a. 3,1,4-benzoxazin-2(1H)-one

To 4.0 g (32.5 mmol) 2-aminobenzyl alcohol in 200 ml $CH_2Cl_2$ at 0° C. was added 11.12 g (81.2 mmol) potassium carbonate followed by 19.3 g (39.0 mmol) 20 wt % phosgene in toluene. The reaction was slowly warmed to room temperature and then stirred for 5 hours. The reaction mixture was poured into 200 ml saturated $NaHCO_3$, the layers were separated and the organic phase was dried over $Na_2SO_4$. Concentration gave 4.55 g (84% yield) of the desired product as a white solid.

This 3,1,4-benzoxazin-2(1H)-one was converted to the desired glutarimide (m.p. 158°–160° C.) as described in Examples 17c–e and Examples 1 and 2 except that 1-iodopropane was used in place of isobutyl iodide.

EXAMPLE 33

7-fluoro-4-epoxypropyl-6-N-(3-trifluoromethyl)glutarimido))-2H-1,4-benzoxazin-3(4H)-one (Compound 239)

To 1.0 g (2.6 mmol) 4-allyl-7-fluoro-6-N-(3-trifluoromethyl)glutarimido))-2H-1,4-benzoxazin-3(4H)-one (Compound 97) in 50 ml $CH_2Cl_2$ was added 2.45 g (7.8 mmol) m-chloroperoxybenzoic acid. The mixture was stirred at room temperature overnight and then poured into 50 ml saturated $NaHCO_3$. The layers were separated and the organic phase was dried over $Na_2SO_4$ before evaporating to dryness in vacuo. The crude product was chromatographed by preparative thin layer chromatography using 60/40 hexanes/EtOAc to give 400 mg (38% yield) of the desired epoxide as a clear oil.

Compound 245 was prepared using the above procedure except the starting material was N-(5'-allyloxy-4'-chloro-2'-fluorophenyl)-3-(trifluoromethyl)glutarimide (Compound 9) and the reaction was refluxed overnight in $CHCl_3$.

EXAMPLE 34

N-[4'-chloro-5'-(3,3-dichloroallyloxy)-2'-fluorophenyl]-3-(trifluoromethyl)glutarimide (Compound 244)

Potassium hydroxide (1.95 g, 34.8 mmol) dissolved in 5 ml water was added to a solution of 5-amino-2-chloro-4-fluorophenol (5.65 g, 34.8 mmol) in 40 ml dimethylsulfoxide. The resulting mixture was stirred at room temperature for 18 hours, poured into 100 ml water and extracted with $Et_2O$ (2×100 ml). The combined organic layers were washed with water (2×100 ml), dried over $Na_2SO_4$, and filtered through a short pad of neutral alumina with $Et_2O$ (3×50 ml rinses). The filtrate was concentrated in vacuo to yield 7.56 g (74% yield) of a brown oil containing mostly the desired product as identified by $^1H$ NMR.

This crude aniline was reacted with 3-(trifluoromethyl)glutaric anhydride as described in Examples 1 and 2 to yield the desired product, m.p. 106°–108° C.

Using the same procedure as used in this example, Compound 240 was prepared except the alkylating agent was 2-chloro-1-butene. Compound 243 was also prepared using this procedure only propargyl bromide was the alkylating agent and the aniline was reacted with 3-(difluoromethyl)glutaric anhydride instead of 3-(trifluoromethyl)glutaric anhydride.

EXAMPLE 35

N-(4'-chloro-2'-fluoro-5'-nitrophenyl)-3-(trifluoromethyl)glutarimide (Compound 222)

a. 4-chloro-2-fluoro-5-nitroacetanilide

Into a 500 ml, 3-necked round-bottomed flask equipped with a mechanical stirrer was placed 4-chloro-2-fluoroacetanilide (56.3 g, 0.3 mmol) and conc. $H_2SO_4$ (100 ml). While cooling to 0° C., fuming nitric acid (21 g, 0.33 mol) was added over 30 minutes and then the reaction mixture was poured onto 2 liters of ice. When the ice had melted the solid product was collected by filtration, washed with water and dried in vacuo to give 44 g (63% yield) of the nitrated material as a tan solid.

b. 4-chloro-2-fluoro-5-nitroaniline

A mixture of 4-chloro-2-fluoro-5-nitroacetanilide (10.88 g, 46.8 mmol), 50.4 ml ethanol, 65.7 ml water, and 43.8 ml (526 mmol) concentrated hydrochloric acid was refluxed for one hour and then poured onto 300 ml ice. The aqueous phase was made strongly basic by the addition of 50% aqueous sodium hydroxide and was extracted with 2×200 ml $Et_2O$. The combined organic layers were washed with water (200 ml) and brine (200 ml) then dried over $Na_2SO_4$ and concentrated to dryness in vacuo to give 8 g (90% yield) of the desired aniline as a yellow solid.

This aniline was reacted with 3-(trifluoromethyl)glutaric anhydride as described in Examples 1 and 2 to yield the desired glutarimide, m.p. 164°–167° C.

EXAMPLE 36

N-(5'-isobutylsulfoxy-4'-chloro-2'-fluorophenyl)-3-(trifluoromethyl)glutarimide (Compound 246)

To a solution of 4-chloro-2-fluoro-5-(isobutylthio) acetanilide (see Example 28a) (1.04 g, 3.8 mmol) in 30 ml ethanol, cooled to 0° C., was added sodium periodate (1.29 g, 6.0 mmol) in 6 ml water. The reaction was allowed to warm to room temperature and was stirred for 18 hours. The solids were removed by suction filtration and the filtrate was dissolved in 75 ml $CH_2Cl_2$ and then washed with water (50 ml). The organic layer was dried over $Na_2SO_4$ and concentrated to dryness to yield 1 g (90% yield) of the desired sulfoxide as a white solid.

The procedure of Example 28c was used to prepare the corresponding aniline which was reacted with 3-(trifluoromethyl)glutaric anhydride as described in Example 1 and 2 to give the desired glutarimide, m.p. 133°–134° C.

The compounds of the present invention are broad spectrum herbicides and may be advantageously employed to control selectively monocot and/or dicot weeds in agronomic and horticultural crops, forestry, orchards, turf, vines or for total weed control.

The compounds of the present invention are selective or non-selective, depending on the rate applied, the combination of plants to which they are applied and whether they are applied pre- or postemergent. Such variables are understood by those skilled in the art. At higher dosage rates they tend to be non-selective, while at lower dosage rates they tend to be selective. For example, the ether and thioether glutarimide compounds described above are active both preemergence and postemergence and have shown postemergent control of dicots in wheat; the ester glutarimides have shown preemergent and postemergent control of monocots and dicots, generally requiring lower doses to control dicots than to control monocots; and the heterocyclic glutarimides have shown selectivity preemergence and/or postemergence in crops such as, but not limited to, wheat, corn, rice, soybeans, sunflower, peanuts and cotton.

The present glutarimides may be applied in any amount which will give the required control of the undesired plants. Generally a rate of application of the herbicides of the invention is from about 0.0001 to about 12 pounds per acre and preferably from about 0.001 to about 5 pounds of the glutarimide compound per acre. Most preferably a rate from about 0.002 to about 2 pounds of the glutarimide per acre is used.

The compounds of the present invention are useful both as preemergence and as postemergence herbicides. Preemergence herbicides may be applied to the soil surface or incorporated into the soil. Postemergence herbicides are those which are applied after the plants have emerged and during their growth period. The glutarimides of the present invention may be applied to the soil surface prior to plant emergence or incorporated into the soil or other growth medium prior to planting. This incorporation can be carried out by any convenient means, including by simply mixing with the soil, by applying the glutarimide to the surface of the soil and then disking or dragging into the soil to the desired depth, or by employing a liquid carrier to accomplish the necessary penetration and impregnation.

A glutarimide of the present invention can be applied postemergence to the growth medium or to plants to be treated either by itself, or, as is generally done, as a component in a herbicidal composition or formulation which also comprises an agronomically acceptable carrier. The concentration of the glutarimide in the herbicidal composition can vary from about 1% to about 98%.

By agronomically acceptable carrier is meant any substance which can be used to dissolve, disperse or diffuse a herbicidal compound in the composition without impairing the effectiveness of the herbicidal compound and which by itself has no detrimental effect on the soil, equipment, crops or agronomic environment. Mixtures of the glutarimides of the present invention may also be used in any of these herbicidal formulations. The herbicidal compositions of the invention can be either solid or liquid formulations or solutions. For example, the glutarimides can be formulated as wettable powders, solutions, emulsifiable concentrates, dusts, granular formulations, aerosols, water dispersable granular formulations or flowable concentrates as is known to one skilled in the art. In such formulations, the compounds are extended with a liquid or solid carrier and, when desired, suitable surfactants or emulsifiers are incorporated.

Examples of solvents which are useful in the practice of this invention include water, alcohols, ketones, aromatic hydrocarbons, halogenated hydrocarbons, dimethylformamide, dioxane, dimethyl sulfoxide and the like. Mixtures of these solvents can also be used.

It is usually desirable, particularly in postemergence applications, to include adjuvants such as wetting agents, spreading agents, dispersing agents, sticking agents, adhesives and the like, in accordance with agricultural practices. Examples of adjuvants which are commonly used in the art can be found in the John W. McCutcheon, Inc. publication "Detergents and Emulsifiers Annual."

The glutarimides of the present invention can also be mixed with fertilizers or fertilizing materials before their application. In one type of solid fertilizing composition in which the glutarimides may be used, particles of a fertilizer or fertilizing ingredients, such as ammonium sulfate, ammonium nitrate or ammonium phosphate can be coated with one or more of the glutarimides. The solid glutarimide and solid fertilizing material may also be admixed in blending or mixing equipment, or they can be incorporated with fertilizers in granular formulations. Any relative proportion of glutarimide and fertilizer can be used which is suitable for the crops and weeds to be treated.

The glutarimides of the present invention may be applied as herbicidal sprays by methods commonly employed, such as conventional high-gallonage hydraulic sprays, low gallonage sprays, air blast spray, aerial sprays and dusts. For some applications two or more of the glutarimides of the instant invention may be combined, thereby providing additional advantages and effectiveness. When mixtures of the glutarimides of the invention are used, the relative proportion of each compound used will depend on the relative efficacy of the compounds in the mixture with respect to the plants to be treated.

For some applications, one or more other herbicides may be added to the glutarimides of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with the glutarimides of the present invention include:

Carboxylic Acids and Derivatives 2,3,6-trichlorobenzoic acid and its salts;
2,3,5,6-tetrachlorobenzoic acid and its salts;
2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;
4-(2-methyl-4-chlorophenoxy)butyric acid and its salts and esters;
2,3,6-trichlorophenylacetic acid and its salts;
3,6-endoxohexahydrophthalic acid and its salts;
dimethyl 2,3,5,6-tetrachloroterephthalate;
trichloroacetic acid and its salts;
2,2-dichloropropionic acid and its salts;
2,3-dichloroisobutyric acid and its salts;
isopropylammonium 2-(4-isopropyl-6-methyl-5-oxo-2-imidazolin-2-yl)nicotinate;

2-[4,5-dihydro-4-methyl-4-(1-methylethyl)-5-oxo-1H-imidazol-2-yl]-3-quinolinecarboxylic acid;
m-toluic acid, 6-(4-isopropyl-4-methyl-5-oxo-2-imidazolin-2-yl)-, methyl ester and p-toluic acid, 6-(4-isopropyl-4-methyl-5-oxo-2-imidazolin-2-yl)-, methyl ester;
N-(phosphonomethyl)glycine, isopropylammonium salt;
[3,5,6-trichloro-(2-pyridinyl)oxy]acetic acid;
3,7-dichloro-8-quinolinecarboxylic acid;
ammonium d1-homoalanin-4-yl(methyl)phosphinate;

Carbamic Acid Derivatives ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiolcarbamate;
2-chloroallyl N,N-diethyldithiocarbamate;
N-methyldithiocarbamic acid salts;
ethyl 1-hexamethyleneiminecarbothiolate;
isopropyl N-phenylcarbamate;
isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts;
S-(4-chlorobenzyl)-N,N-diethylthiolcarbamate;

Substituted Ureas 2-chloro-N-[(4-methoxy-6-methyl-1,3,5-triazin-2-yl)aminocarbonyl]benzenesulfonamide;
3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1-methylurea;
3-(4-chlorophenyl)-1-methoxy-1-methylurea;
3-(3,4-dichlorophenyl)-1,1,3-trimethylurea;
3-(3,4-dichlorophenyl)diethylurea;
dichloral urea;
methyl 2-[[[[(4,6-dimethyl-2-pyrimidinyl)amino]carbonyl]amino]sulfonyl]benzoate;
N-((6-methoxy-4-methyl-1,3,5-triazin-2-yl)aminocarbonyl)-2-(2-chloroethoxy)benzenesulfonamide;
2-[[[(4-chloro-6-methoxypyrimidine-2-yl)aminocarbonyl]amino]sulfonyl]benzoic acid, ethyl ester;
methyl 2-[[[[(4-methoxy-6-methyl-1,3,5-triazin-2-yl)amino]carbonyl]amino]sulfonyl]benzoate;
methyl 3-[[[[(4-methoxy-6-methyl-1,3,5-triazin-2-yl)amino]carbonyl]amino]sulfonyl]-2-thiophenecarboxylate;
methyl 2-[[[[[(4,6-dimethoxypyrimidin-2-yl)amino]carbonyl]amino]sulfonyl]methyl]benzoate;
methyl 2-[[[[(4-methoxy-6-methyl-1,3,5-triazin-2-yl)methylamino]carbonyl]amino]sulfonyl]benzoate;

Substituted Triazines 2-chloro-4,6-bis(ethylamino)-s-triazine;
2-chloro-4-ethylamino-6-isopropylamino-s-triazine;
2-chloro-4,6-bis(methoxy-n-propylamino)-s-triazine;
2-methoxy-4,6-bis(isopropylamino)-s-triazine;
2-chloro-4-ethylamino-6-(3-methoxy-n-propylamino)-s-triazine;
2-methylmercapto-4,6-bis(isopropylamino)-s-triazine;
2-methylmercapto-4,6-bis(ethylamino)-s-triazine;
2-methylmercapto-4-ethylamino-6-isopropylamino-s-triazine;
2-chloro-4,6-bis(isopropylamino)-s-triazine;
2-methoxy-4,6-bis(ethylamino)-s-triazine;
2-methoxy-4-ethylamino-6-isopropylamino-s-triazine;
2-methylmercapto-4-(2-methoxyethylamino)-6-isopropylamino-s-triazine;
4-amino-6-(t-butyl)-3-(methylthio)-1,2,4-triazine-5(4H)-one;

Diphenyl Ether Derivatives 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-4'-nitrodiphenyl ether;
2,4'-dinitro-4-(trifluoromethyl)diphenyl ether;
2,4-dichloro-3'-methoxy-4'-nitrodiphenyl ether;
sodium 5-(2-chloro-4-(trifluoromethyl)phenoxy)-2-nitrobenzoate;
2-chloro-1-(3-ethoxy-4-nitrophenoxy)-4-(trifluoromethyl)benzene;
1-(carboethoxy)ethyl 5-[2-chloro-4-(trifluoromethyl)phenoxy]-2-nitrobenzoate;
5-[2-chloro-4-(trifluoromethyl)phenoxy]-N-(methylsulphonyl)-2-nitrobenzamide;

Anilides 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-alpha,alpha-dimethylvaleramide;
N-isopropyl-N-phenylchloroacetamide;
N-n-butoxymethyl-N-(2,6-diethylphenyl)chloroacetamide;
N-methoxymethyl-N-(2,6-diethylphenyl)chloroacetamide;

Oxyphenoxy Herbicides 2-(4-(2,4-dichlorophenoxy)phenoxy)methyl propionate;
methyl 2-(4-(3-chloro-5-(trifluoromethyl)-2-pyridinyloxy)phenoxy)propanoate;
butyl (R)-2-[4-[5-(trifluoromethyl)-2-pyridinyloxy]phenoxy]propionate;
ethyl 2-[4-[(6-chloro-2-benzoxazolyl)oxy]phenoxy]propanoate;
butyl 2-[4-[[5-(trifluoromethyl)-2-pyridinyl]oxy]phenoxy]propionate;
2-[4-[(6-chloro-2-quinoxalinyl)oxy]phenoxy]propionic acid, ethyl ester;

Uracils 5-bromo-3-s-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil;

Nitriles 2,6-dichlorobenzonitrile; diphenylacetonitrile;
3,5-dibromo-4-hydroxybenzonitrile;
3,5-diiodo-4-hydroxybenzonitrile;

Other Organic Herbicides 2-chloro-N,N-diallylacetamide;
N-(1,1-dimethyl-2-propynyl)-3,5-dichlorobenzamide;
maleic hydrazide;

3-amino-1,2,4-triazole;
monosodium methanearsonate;
disodium methanearsonate;
N,N-dimethyl-alpha,alpha-diphenylacetamide;
N,N-di(n-propyl)-2,6-dinitro-4-(trifluoromethyl)aniline;
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol[1,2-a:2',1'-c]pyrazidiium salts;
1,1'-dimethyl-4,4'-bipyridinium salts;
3,4,5,6-tetrahydro-3,5-dimethyl-2-thio-2H-1,3,5-thiadiazine;
2-[1-(ethoxyimino)butyl]-5-[2-(ethylthio)propyl]-3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
-chloro-5-(methylamino)-2-(α,α,α-trifluoro-m-toluyl)-3 (2H)-pyridazinone;
2-(3,5-dichlorophenyl)-2-(2,2,2-trichloromethyl)oxirane.

The herbicidal activity of glutarimides of the present invention towards a number of common weeds was evaluated using a greenhouse method of testing. Using the procedures described below, the glutarimides of the present invention were evaluated for control of weeds selected from the following:

| Monocots | |
|---|---|
| Barnyardgrass (BYG) | *Echinochloa crus-galli* |

| Crabgrass (CRB) | *Digitaria sanguinilis* |
|---|---|
| Foxtail (FOX) | *Setaria viridis* |
| Johnsongrass (JON) | *Sorghum halepense* |
| Meadow Foxtail (MF) | *Alopecurus pratensis* |
| Nutsedge (NUT) | *Cyperus esculentus* |
| Wild Oat (WO) | *Avena fatua* |
| Dicots | |
| Beggartick (BID) | *Bidens pilosa* |
| Cocklebur (CKL) | *Xanthium strumarium* |
| Morningglory (MG) | *Ipomoea lacunosa* |
| Nightshade (NS) | *Solanum nigrum* |
| Pigweed (PIG) | *Amaranthus retroflexus* |
| Smartweed (SMT) | *Polygonum lapathifolium* |
| Velvetleaf (VEL) | *Abutilon theophrasti* |

The following test procedure was employed. Seeds of selected plants were planted in flats or pots. For preemergence tests, immediately after planting, the test compound was sprayed directly onto the soil surface. The flats or pots were then watered by overhead irrigation. For postemergence tests, the seeds were allowed to germinate and grow for 10 to 21 days. Each series of test plants were selected for uniformity, size and stage of development. The test plants were then treated with the test compound. The plants for postemergence tests were watered by subirrigation only.

The compound to be evaluated was dissolved in an appropriate solvent, usually acetone, and sprayed over the flats or pots using a carrier volume equivalent to 25 or 50 gallons per acre at the rate of application in pounds per acre (lb./A) specified in the table. About ten to twenty-one days after application of the test compound, the state of growth of the plant was observed. Each species was evaluated on a scale of 0–100 in which 0 equals no activity and 100 equals total control. The following tables (Tables VI and VII) shows the results obtained for the test compounds at the stated rate of application.

TABLE VI

HERBICIDAL ACTIVITY

| Compound No. | Rate (lb./A) | Type | CKL | MG | PIG | VEL | SMT | BYG | FOX | ION | NUT | WO |
|---|---|---|---|---|---|---|---|---|---|---|---|---|
| 1. | 2 | PRE | 100 | 100 | 100 | 100 | 100 | 100 | 100 | 100 | 100 | 100 |
|  | 2 | POST | 100 | 100 | 100 | 100 | —* | 100 | 100 | 99 | 98 | 100 |
| 3. | 2 | PRE | 100 | 100 | 100 | 100 | 100 | 100 | 100 | 100 | 100 | 100 |
|  | 2 | POST | 100 | 100 | 100 | 100 | — | 100 | 100 | 99 | 5 | 100 |
| 3. | 2 | PRE | 100 | 100 | 100 | 100 | — | 100 | 100 | 100 | 80 | 99 |
|  | 2 | POST | 100 | 100 | 100 | 100 | 100 | 100 | 100 | 99 | 80 | 90 |
| 4. | 2 | PRE | 0 | 100 | 100 | 100 | 100 | 100 | 100 | 85 | 10 | 90 |
|  | 2 | POST | 99 | 100 | 100 | 100 | 100 | 100 | 100 | 65 | 10 | 70 |
| 5. | 1 | PRE | 71 | 100 | 100 | 100 | 100 | 100 | 100 | 100 | 65 | 100 |
|  | 1 | POST | 100 | 100 | 100 | 100 | 100 | 99 | 100 | 90 | 90 | 100 |
| 6. | 1 | PRE | 100 | 100 | 100 | 100 | 100 | 100 | 100 | 98 | 100 | 100 |
|  | 1 | POST | 100 | 100 | 100 | 100 | 100 | 100 | 100 | 100 | 0 | 60 |
| 7. | 1 | PRE | 100 | 100 | 100 | 100 | 100 | 99 | 100 | 100 | 0 | 100 |
|  | 1 | POST | 100 | 99 | 100 | 100 | 100 | 100 | 100 | 100 | 0 | 35 |
| 8. | 1 | PRE | 0 | 90 | 0 | 100 | 15 | 41 | 98 | 0 | 0 | 0 |
|  | 1 | POST | 45 | 15 | 100 | 100 | 100 | 45 | 75 | 15 | 0 | 35 |
| 9. | 2 | PRE | 75 | 100 | 100 | 100 | — | 100 | 100 | 90 | 80 | 90 |
|  | 2 | POST | 100 | 100 | 100 | 100 | 100 | 100 | 100 | 70 | 65 | 100 |
| 10. | 1 | PRE | 100 | 100 | 100 | 100 | 100 | 100 | 100 | 100 | 30 | 100 |
|  | 1 | POST | 71 | 100 | 100 | 100 | 100 | 100 | 100 | 100 | 100 | 100 |
| 11. | 1 | PRE | 0 | 0 | 0 | 100 | 0 | 0 | 21 | 15 | 0 | 0 |
|  | 1 | POST | 70 | 60 | 95 | 100 | 100 | 15 | 25 | 5 | 0 | 0 |
| 12. | 1 | PRE | 0 | 100 | 100 | 100 | 100 | 99 | 100 | 95 | 80 | 98 |
|  | 1 | POST | 100 | 100 | 100 | 100 | 100 | 95 | 100 | 98 | 10 | 100 |
| 13. | 4 | PRE | — | 0 | 0 | 0 | 0 | 0 | 0 | 0 | 0 | 0 |
|  | 4 | POST | 15 | 45 | 100 | 45 | 15 | 10 | 30 | 10 | 0 | 10 |

TABLE VI-continued

HERBICIDAL ACTIVITY

| Compound No. | Rate (lb./A) | Type | CKL | MG | PIG | VEL | SMT | BYG | FOX | ION | NUT | WO |
|---|---|---|---|---|---|---|---|---|---|---|---|---|
| 14. | 4 | PRE | 80 | 100 | 100 | 100 | 100 | 100 | 100 | 100 | 100 | 100 |
|  | 4 | POST | 0 | 100 | 100 | 100 | 0 | 100 | 100 | 98 | 45 | 98 |
| 15. | 4 | PRE | 0 | 0 | 100 | 100 | 100 | 10 | 100 | 20 | 0 | 0 |
|  | 4 | POST | 5 | 35 | 20 | 60 | 10 | 15 | 90 | 10 | 0 | 5 |
| 16. | 4 | PRE | 0 | 95 | 100 | 100 | 0 | 0 | 95 | 0 | 0 | 27 |
|  | 4 | POST | 0 | 80 | 100 | 100 | 10 | 20 | 100 | 10 | 0 | 10 |
| 17. | 4 | PRE | 100 | 100 | 100 | 100 | 100 | 100 | 100 | 98 | 100 | 75 |
|  | 4 | POST | 100 | 100 | 100 | 100 | 100 | 100 | 99 | 25 | 65 | 65 |
| 18. | 4 | PRE | 0 | 100 | 100 | 100 | 50 | 100 | 100 | 70 | 98 | 65 |
|  | 4 | POST | 35 | 55 | 100 | 100 | 98 | 85 | 100 | 10 | 80 | 10 |
| 19. | 4 | PRE | 0 | 90 | 100 | 100 | 0 | 45 | 100 | 0 | 20 | 25 |
|  | 4 | POST | 100 | 90 | 98 | 100 | 20 | 100 | 100 | 25 | 10 | 85 |
| 20. | 4 | PRE | 0 | 0 | 100 | 100 | 50 | 0 | 0 | 0 | 0 | 0 |
|  | 4 | POST | 100 | 20 | 100 | 100 | 100 | 90 | 100 | 20 | 10 | 15 |
| 21. | 4 | PRE | 31 | 61 | 100 | 100 | 100 | 0 | 100 | 0 | 0 | 0 |
|  | 4 | POST | 15 | 10 | 100 | 95 | 100 | 0 | 0 | 0 | 0 | 0 |
| 22. | 4 | PRE | 98 | 100 | 100 | 100 | 100 | 100 | 100 | 80 | 75 | 51 |
|  | 4 | POST | 55 | 55 | 100 | 100 | 85 | 20 | 100 | 5 | 45 | 5 |
| 23. | 4 | PRE | 0 | 0 | 100 | 100 | 0 | 90 | 100 | 15 | 0 | 0 |
|  | 4 | POST | 0 | 0 | 25 | 0 | 0 | 0 | 0 | 0 | 0 | 0 |
| 24. | 1 | PRE | 0 | 100 | 100 | 100 | 100 | 70 | 100 | 85 | 70 | 10 |
|  | 1 | POST | 100 | 99 | 100 | 100 | 100 | 40 | 100 | 20 | 10 | 20 |
| 25. | 1 | PRE | 0 | 100 | 100 | 100 | 100 | 99 | 100 | 85 | 85 | 90 |
|  | 1 | POST | 40 | 100 | 100 | 100 | 100 | 100 | 100 | 30 | 10 | 25 |
| 26. | 4 | PRE | 0 | 0 | 100 | 15 | 0 | 15 | 100 | 20 | 0 | 0 |
|  | 4 | POST | 15 | 15 | 90 | 100 | 35 | 0 | 15 | 5 | 0 | 0 |
| 27. | 4 | PRE | 0 | 0 | 100 | 20 | — | 75 | 100 | 51 | 0 | 20 |
|  | 4 | POST | 0 | 70 | 100 | 35 | 100 | 70 | 45 | 15 | 0 | 15 |
| 28. | 4 | PRE | 0 | 90 | 100 | 100 | 100 | 98 | 100 | 95 | 25 | 85 |
|  | 4 | POST | 0 | 5 | 100 | 100 | 100 | 5 | 5 | 0 | 0 | 0 |
| 29. | 2 | PRE | 100 | 100 | 100 | 100 | 100 | 100 | 100 | 100 | 100 | 100 |
|  | 2 | POST | 100 | 100 | 100 | 100 | 100 | 100 | 100 | 85 | 95 | 99 |
| 30. | 1 | PRE | 0 | 100 | 100 | 100 | 100 | 100 | 100 | 80 | 85 | 80 |
|  | 1 | POST | 45 | 100 | 90 | 100 | 100 | 95 | 95 | 40 | 0 | 45 |
| 31. | 4 | PRE | 0 | 0 | 100 | 100 | — | 50 | 100 | 85 | — | 0 |
|  | 4 | POST | 0 | 0 | 5 | 0 | — | 0 | 0 | 0 | 0 | 0 |
| 32. | 4 | PRE | 0 | 15 | 100 | 100 | 80 | 75 | 100 | 0 | 60 | 21 |
|  | 4 | POST | 0 | 5 | 10 | 5 | 10 | 0 | 0 | 0 | 0 | 0 |
| 34. | 4 | PRE | 0 | 5 | 100 | 100 | 0 | 75 | 100 | 5 | 5 | 0 |
|  | 4 | POST | 5 | 45 | 90 | 100 | 98 | 20 | 15 | 5 | 0 | 5 |
| 35. | 4 | PRE | 0 | 0 | — | 100 | 0 | 0 | 21 | 0 | 0 | 0 |
|  | 4 | POST | 0 | 10 | 0 | 0 | 0 | 0 | 0 | 0 | 0 | 0 |
| 36. | 4 | PRE | 0 | 0 | 0 | 0 | 0 | 0 | 0 | 0 | 0 | 0 |
|  | 4 | POST | 0 | 20 | 15 | 25 | 0 | 10 | 5 | 0 | 0 | 0 |
| 37. | 4 | PRE | 0 | 0 | 0 | 21 | 51 | 21 | 51 | 51 | 51 | 61 |
|  | 4 | POST | 0 | 0 | 0 | 0 | 0 | 0 | 0 | 0 | 0 | 0 |
| 38. | 1 | PRE | 0 | 0 | 100 | 100 | 100 | 60 | 100 | 25 | 0 | 15 |
|  | 1 | POST | 5 | 10 | 15 | 10 | 10 | 0 | 0 | 0 | 0 | 0 |
| 39. | 4 | PRE | 0 | 0 | — | 45 | 0 | 0 | 0 | 0 | 0 | 0 |
|  | 4 | POST | 0 | 0 | 0 | 0 | 0 | 0 | 0 | 0 | 0 | 0 |
| 40. | 4 | PRE | 0 | 0 | 0 | 0 | 0 | 0 | 0 | 0 | 0 | 0 |
|  | 4 | POST | 0 | 0 | 0 | 0 | 10 | 0 | 0 | 0 | 0 | 0 |
| 41. | 1 | PRE | 0 | 100 | — | 100 | 100 | 98 | 100 | 100 | 0 | 98 |
|  | 1 | POST | 100 | 70 | 100 | 100 | 100 | 80 | 75 | 15 | 10 | 65 |
| 42. | 4 | PRE | 0 | 15 | 0 | 100 | 70 | 0 | 85 | 0 | 10 | 0 |
|  | 4 | POST | 15 | 25 | 10 | 5 | 10 | 10 | 25 | 0 | 0 | 5 |
| 43. | 2 | PRE | 100 | 100 | 100 | 100 | 100 | 100 | 100 | 90 | 100 | 100 |
|  | 2 | POST | 100 | 100 | 100 | 100 | 100 | 100 | 100 | 90 | 100 | 100 |
| 44. | 1 | PRE | 0 | 100 | 100 | 100 | 100 | 100 | 100 | 15 | 100 | 75 |
|  | 1 | POST | 100 | 100 | 100 | 100 | 100 | 80 | 100 | 70 | 0 | 30 |
| 45. | 1 | PRE | 100 | 100 | 100 | 100 | 100 | 100 | 100 | 99 | 55 | 100 |
|  | 1 | POST | 100 | 100 | 100 | 100 | 100 | 99 | 85 | 70 | 20 | 85 |
| 46. | 1 | PRE | 15 | 70 | 100 | 100 | 100 | 100 | 100 | 90 | 100 | 80 |
|  | 1 | POST | 100 | 80 | 100 | 100 | 100 | 80 | 60 | 45 | 10 | 25 |
| 47. | 1 | PRE | 10 | 100 | 100 | 100 | 100 | 98 | 100 | 45 | 11 | 90 |
|  | 1 | POST | 90 | 90 | 100 | 100 | 100 | 20 | 5 | 5 | 5 | 15 |
| 48. | 1 | PRE | 0 | 90 | 100 | 100 | 100 | 85 | 100 | 15 | 0 | 60 |
|  | 1 | POST | 95 | 90 | 100 | 100 | 100 | 25 | 10 | 10 | 0 | 10 |
| 49. | 4 | PRE | 0 | 0 | — | 90 | 20 | 0 | 15 | 0 | 0 | 0 |
|  | 4 | POST | 0 | 10 | 0 | 0 | — | 0 | 0 | 0 | 0 | 0 |
| 50. | 1 | PRE | 0 | 100 | 100 | 100 | 100 | 95 | 100 | 80 | 0 | 10 |
|  | 1 | POST | 100 | 100 | 70 | 100 | 100 | 80 | 40 | 30 | 0 | 20 |
| 51. | 1 | PRE | 100 | 100 | 100 | 100 | 100 | 100 | 100 | 80 | 65 | 100 |
|  | 1 | POST | 100 | 100 | 100 | 100 | 100 | 100 | 100 | 100 | 45 | 100 |

TABLE VI-continued

HERBICIDAL ACTIVITY

| Compound No. | Rate (lb./A) | Type | CKL | MG | PIG | VEL | SMT | BYG | FOX | ION | NUT | WO |
|---|---|---|---|---|---|---|---|---|---|---|---|---|
| 53. | 1 | PRE | 61 | 100 | 100 | 100 | 100 | 25 | 100 | 75 | 20 | 15 |
| | 1 | POST | 100 | 20 | 98 | 100 | 95 | 10 | 35 | 0 | 0 | 10 |
| 54. | 1 | PRE | 0 | 0 | 0 | 0 | 0 | 0 | 0 | 0 | 0 | 0 |
| | 1 | POST | 0 | 100 | 100 | 100 | 100 | 95 | 15 | 0 | 0 | 10 |
| 55. | 4 | PRE | 0 | 85 | 100 | 20 | 90 | 0 | 15 | 0 | 0 | 0 |
| | 4 | POST | 80 | 100 | 100 | 100 | 100 | 45 | 40 | 5 | 0 | 5 |
| 56. | 1 | PRE | 0 | 0 | — | 0 | — | 0 | 0 | 0 | 0 | 0 |
| | 1 | POST | 80 | 100 | 100 | 100 | 100 | 100 | 35 | 90 | 10 | 60 |
| 57. | 1 | PRE | 0 | 100 | 0 | 100 | 100 | 0 | 0 | — | 0 | 0 |
| | 1 | POST | 100 | 100 | 100 | 100 | 90 | 20 | 25 | 0 | 0 | 0 |
| 58. | 1 | PRE | 0 | 20 | 100 | 100 | 25 | 0 | 0 | — | 0 | 0 |
| | 1 | POST | 5 | 80 | 65 | 70 | 100 | 0 | 0 | 25 | 0 | 0 |
| 59. | 1 | PRE | 0 | 0 | 100 | 100 | 0 | 0 | 0 | 0 | 0 | 0 |
| | 1 | POST | 100 | 100 | 100 | 75 | 100 | 15 | 70 | 10 | 0 | 0 |
| 60. | 1 | PRE | 51 | 100 | 100 | 100 | 100 | 70 | 100 | 90 | 0 | 0 |
| | 1 | POST | 100 | 100 | 100 | 100 | 100 | 100 | 100 | 100 | 20 | 25 |
| 61. | 1 | PRE | 0 | 0 | 0 | 50 | 0 | 0 | 85 | 0 | 0 | 0 |
| | 1 | POST | 100 | 100 | 100 | 100 | 100 | 100 | 100 | 100 | 30 | 45 |
| 62. | 1 | PRE | 0 | 0 | 0 | 0 | 0 | 0 | 0 | 0 | 0 | 0 |
| | 1 | POST | 98 | 70 | 100 | 100 | 85 | 90 | 100 | 35 | 0 | 0 |
| 63. | 4 | PRE | 0 | 0 | 0 | 100 | 100 | 0 | 75 | 0 | 0 | 10 |
| | 4 | POST | 5 | 0 | 0 | 0 | 0 | 0 | 0 | 0 | 0 | 0 |
| 64. | 2 | PRE | 0 | 0 | 0 | 0 | 0 | 0 | 0 | 0 | 0 | 0 |
| | 2 | POST | — | 0 | 85 | 15 | 100 | 15 | 0 | 0 | 0 | 0 |
| 65. | 2 | PRE | — | 0 | 100 | 0 | 0 | 0 | 0 | 0 | 0 | 0 |
| | 2 | POST | 30 | 30 | 100 | 90 | 100 | 0 | 10 | 10 | 0 | 0 |
| 66. | 4 | PRE | 0 | 0 | 0 | 25 | 0 | 0 | 5 | 0 | 0 | 0 |
| | 4 | POST | 0 | 0 | 10 | 35 | 0 | 0 | 0 | 0 | 0 | 0 |
| 67. | 4 | PRE | — | 0 | 100 | 0 | 100 | — | 0 | 90 | 0 | 0 |
| | 4 | POST | 0 | 5 | 5 | 10 | 0 | 0 | 0 | 0 | 0 | 5 |
| 68. | 4 | PRE | 0 | 0 | — | 100 | 25 | 0 | 5 | 0 | 0 | 0 |
| | 4 | POST | 0 | 0 | 0 | 0 | 0 | 0 | 0 | 0 | 0 | 0 |
| 69. | 4 | PRE | 0 | 0 | 0 | 100 | 0 | 90 | 0 | 0 | 0 | 0 |
| | 4 | POST | 0 | 15 | 5 | 0 | 5 | 0 | 0 | 0 | 0 | 0 |
| 70. | 4 | PRE | 0 | 0 | — | 100 | 0 | 0 | 11 | 0 | 0 | 0 |
| | 4 | POST | 0 | 5 | 0 | 0 | 0 | 0 | 0 | 0 | 0 | 0 |
| 71. | 1 | PRE | 36 | 100 | 100 | 100 | — | 80 | 100 | 25 | 0 | 0 |
| | 1 | POST | 100 | 100 | 100 | 100 | 100 | 100 | 100 | 100 | 60 | 75 |
| 72. | 1 | PRE | 0 | 100 | — | 100 | — | 90 | 100 | 0 | 0 | 60 |
| | 1 | POST | 100 | 100 | 100 | 100 | 100 | 95 | 100 | 85 | 5 | 65 |
| 73. | 1 | PRE | 0 | 95 | — | 0 | — | 75 | 100 | 0 | 0 | 20 |
| | 1 | POST | 60 | 20 | 80 | 100 | 100 | 15 | 80 | 5 | 15 | 5 |
| 74. | 1 | PRE | 0 | 0 | 0 | 100 | 0 | 0 | 15 | 5 | 0 | 0 |
| | 1 | POST | 100 | 100 | 100 | 100 | 100 | 100 | 100 | 95 | 10 | 25 |
| 75. | 1 | PRE | 15 | 100 | 100 | 100 | 100 | 70 | 100 | 60 | 0 | 70 |
| | 1 | POST | 100 | 100 | 100 | 100 | 100 | 95 | 100 | 75 | 0 | 10 |
| 76. | 1 | PRE | 0 | 100 | 100 | 100 | 100 | 100 | 100 | 90 | 35 | 90 |
| | 1 | POST | 55 | 100 | 100 | 100 | 25 | 80 | 95 | 80 | 10 | 40 |
| 77. | 4 | PRE | 30 | 100 | 100 | 100 | 100 | 99 | 100 | 80 | 0 | 55 |
| | 4 | POST | 45 | 70 | 100 | 95 | 100 | 15 | 40 | 0 | 0 | 0 |
| 78. | 4 | PRE | 90 | 100 | 100 | 100 | 100 | 100 | 100 | 99 | 45 | 75 |
| | 4 | POST | 25 | 20 | 20 | 100 | 100 | 0 | 25 | 0 | 0 | 0 |
| 79. | 4 | PRE | 0 | 100 | 100 | 100 | 100 | 99 | 95 | 95 | 0 | 15 |
| | 4 | POST | 35 | 50 | 55 | 95 | 100 | 0 | 0 | 10 | 10 | 10 |
| 80. | 4 | PRE | 90 | 100 | 100 | 100 | 100 | 100 | 100 | 100 | 15 | 99 |
| | 4 | POST | 60 | 85 | 100 | 100 | 100 | 100 | 100 | 85 | 30 | 45 |
| 81. | 1 | PRE | 80 | 100 | 100 | 100 | 100 | 100 | 100 | 100 | 75 | 90 |
| | 1 | POST | 55 | 100 | 100 | 100 | 98 | 30 | 60 | 15 | 20 | 30 |
| 82. | 1 | PRE | 0 | 100 | 100 | 100 | 100 | 100 | 100 | 98 | 25 | 85 |
| | 1 | POST | 100 | 100 | 100 | 100 | 100 | 100 | 100 | 95 | 35 | 80 |
| 83. | 1 | PRE | 25 | 100 | 100 | 100 | 100 | 100 | 100 | 95 | 25 | 50 |
| | 1 | POST | 100 | 100 | 100 | 100 | 100 | 95 | 100 | 70 | 20 | 0 |
| 84. | 4 | PRE | 100 | 100 | 100 | 100 | 100 | 100 | 100 | 100 | 70 | 98 |
| | 4 | POST | 30 | 100 | 100 | 100 | 100 | 15 | 70 | 100 | 100 | 70 |
| 85. | 1 | PRE | 100 | 100 | 100 | 100 | 100 | 100 | 100 | 100 | 100 | 100 |
| | 1 | POST | 60 | 100 | 100 | 100 | 0 | 100 | 100 | 0 | 0 | 0 |
| 86. | 4 | PRE | 0 | 0 | — | 0 | 0 | 0 | 20 | 0 | 0 | 0 |
| | 4 | POST | 0 | 0 | 100 | 99 | 0 | 80 | 100 | 70 | 0 | 10 |
| 87. | 4 | PRE | 30 | 100 | 100 | 100 | 100 | 100 | 100 | 100 | 98 | 90 |
| | 4 | POST | 45 | 10 | 100 | 100 | 100 | 50 | 65 | 55 | 35 | 15 |
| 88. | 1 | PRE | 80 | 100 | 100 | 100 | 100 | 100 | 100 | 100 | 15 | 95 |
| | 1 | POST | 70 | 100 | 90 | 100 | 100 | 25 | 50 | 50 | 0 | 0 |
| 89. | 0.3 | PRE | 100 | 100 | 100 | 100 | 100 | 100 | 100 | 100 | 90 | 100 |
| | 0.3 | POST | 100 | 100 | 100 | 100 | 100 | 100 | 100 | 100 | 85 | 100 |

TABLE VI-continued

HERBICIDAL ACTIVITY

| Compound No. | Rate (lb./A) | Type | CKL | MG | PIG | VEL | SMT | BYG | FOX | ION | NUT | WO |
|---|---|---|---|---|---|---|---|---|---|---|---|---|
| 90. | 0.3 | PRE | 60 | 100 | 100 | 100 | 100 | 55 | 100 | 60 | 0 | 0 |
|  | 0.3 | POST | 100 | 100 | 100 | 100 | 100 | 20 | 35 | 25 | 15 | 25 |
| 91. | 4 | PRE | 0 | 0 | 100 | 60 | 100 | 0 | 100 | 15 | 0 | 20 |
|  | 4 | POST | 5 | 0 | 20 | 0 | 0 | 0 | 0 | 0 | 0 | 0 |
| 92. | 1 | PRE | 95 | 15 | 100 | 100 | 100 | 100 | 100 | 100 | 100 | 80 |
|  | 1 | POST | 100 | 75 | 100 | 100 | 100 | 100 | 100 | 95 | 100 | 40 |
| 96. | 1 | PRE | 100 | 100 | — | 100 | 100 | 100 | 100 | 100 | 100 | 100 |
|  | 1 | POST | 75 | 100 | 100 | 100 | 100 | 85 | 90 | 35 | 100 | 0 |
| 97. | 1 | PRE | 100 | 100 | 100 | 100 | 100 | 100 | 100 | 100 | 100 | 100 |
|  | 1 | POST | 100 | 100 | 100 | 100 | 100 | 100 | 100 | 100 | 100 | 75 |
| 98. | 1 | PRE | 100 | 100 | — | 100 | 100 | 100 | 100 | 100 | 100 | 100 |
|  | 1 | POST | 98 | 100 | 100 | 100 | 100 | 100 | 100 | 100 | 100 | 95 |
| 99. | 4 | PRE | 0 | 0 | 0 | 20 | — | 0 | 45 | 0 | 0 | 0 |
|  | 4 | POST | 0 | 25 | 45 | 70 | 0 | 5 | 10 | 0 | 0 | 0 |
| 100. | 1 | PRE | 0 | 20 | 100 | 100 | 65 | 0 | 30 | 10 | 0 | 0 |
|  | 1 | POST | 35 | 90 | 100 | 100 | 65 | 25 | 15 | 15 | 10 | 15 |
| 101. | 1 | PRE | 0 | 0 | 100 | 50 | 100 | 0 | 0 | 0 | 0 | 0 |
|  | 1 | POST | 20 | 25 | 10 | 65 | 100 | 25 | 0 | 0 | 0 | 0 |
| 102. | 1 | PRE | 100 | 100 | 100 | 100 | 100 | 90 | 100 | 85 | 0 | 15 |
|  | 1 | POST | 100 | 100 | 100 | 100 | 100 | 100 | 100 | 60 | 10 | 0 |
| 103. | 1 | PRE | 0 | 0 | 100 | 90 | 99 | 0 | 25 | 0 | 0 | 0 |
|  | 1 | POST | 100 | 98 | 100 | 100 | 100 | 50 | 98 | 20 | 0 | 0 |
| 104. | 1 | PRE | 100 | 100 | 100 | 100 | 100 | 95 | 100 | 95 | 0 | 50 |
|  | 1 | POST | 100 | 100 | 100 | 100 | 100 | 40 | 95 | 10 | 0 | 0 |
| 105. | 1 | PRE | 100 | 100 | 100 | 100 | 100 | 100 | 100 | 100 | 65 | 100 |
|  | 1 | POST | 85 | 100 | 100 | 100 | 100 | 55 | 85 | 85 | 35 | — |
| 106. | 1 | PRE | 0 | 50 | 100 | 100 | 100 | 85 | 100 | 60 | 0 | 95 |
|  | 1 | POST | 10 | 10 | 70 | 100 | 60 | 15 | 30 | 10 | 0 | 15 |
| 107. | 1 | PRE | 0 | 90 | 100 | 100 | 100 | 90 | 100 | 60 | 0 | 75 |
|  | 1 | POST | 15 | 30 | 100 | 100 | 95 | 15 | 20 | 15 | 0 | 15 |
| 108. | 1 | PRE | 10 | 20 | 100 | 100 | 100 | 55 | 100 | 70 | 0 | 10 |
|  | 1 | POST | 30 | 65 | 35 | 100 | 100 | 0 | 0 | 10 | 15 | 15 |
| 109. | 1 | PRE | 0 | 0 | 100 | 10 | 0 | 55 | 10 | 0 | 0 | 0 |
|  | 1 | POST | 40 | 65 | 10 | 99 | 95 | 0 | 0 | 0 | 0 | 0 |
| 110. | 1 | PRE | 10 | 20 | 100 | 100 | 100 | 90 | 100 | 30 | 5 | 10 |
|  | 1 | POST | 95 | 100 | 100 | 100 | 90 | 100 | 100 | 85 | 20 | 15 |
| 111. | 1 | PRE | 100 | 95 | 100 | 100 | 100 | 100 | 100 | 90 | 20 | 95 |
|  | 1 | POST | 100 | 100 | 100 | 100 | 100 | 100 | 100 | 100 | 80 | 95 |
| 112. | 1 | PRE | 15 | 90 | 100 | 100 | 100 | 100 | 100 | 45 | 10 | 45 |
|  | 1 | POST | 100 | 100 | 100 | 100 | 100 | 100 | 100 | 20 | 80 | 100 |
| 113. | 1 | PRE | 50 | 85 | — | 100 | 100 | 95 | 100 | 75 | 0 | 10 |
|  | 1 | POST | 75 | 90 | 100 | 100 | 100 | 100 | 100 | 30 | 15 | 90 |
| 114. | 1 | PRE | 90 | 100 | 100 | 100 | 100 | 100 | 100 | 95 | 25 | 99 |
|  | 1 | POST | 50 | 35 | 95 | 95 | 99 | 70 | 100 | 70 | 0 | 45 |
| 115. | 1 | PRE | 75 | 65 | 100 | 100 | 100 | 100 | 100 | 100 | 35 | 80 |
|  | 1 | POST | 100 | 100 | 100 | 100 | 100 | 100 | 100 | 100 | 15 | 80 |
| 116. | 1 | PRE | 100 | 100 | 100 | 100 | 100 | 98 | 100 | 85 | 15 | 98 |
|  | 1 | POST | 95 | 95 | 100 | 100 | 100 | 100 | 100 | 65 | 15 | 80 |
| 117. | 1 | PRE | 100 | 100 | 100 | 100 | 100 | 100 | 100 | 99 | 65 | 100 |
|  | 1 | POST | 100 | 100 | 100 | 100 | 100 | 100 | 100 | 100 | 55 | 100 |
| 118. | 1 | PRE | 100 | 100 | 100 | 100 | 100 | 100 | 100 | 100 | 100 | 100 |
|  | 1 | POST | 100 | 100 | 100 | 100 | 100 | 100 | 100 | 100 | 45 | 100 |
| 119. | 4 | PRE | 10 | 0 | 100 | 100 | 0 | 85 | 100 | 45 | 0 | 15 |
|  | 4 | POST | 0 | 0 | 0 | 0 | 0 | 0 | 0 | 0 | 0 | 0 |
| 120. | 4 | PRE | 0 | 0 | 95 | 100 | 85 | 95 | 100 | 80 | 0 | 15 |
|  | 4 | POST | 0 | 0 | 0 | 0 | 0 | 0 | 0 | 0 | 0 | 0 |
| 122. | 1 | PRE | 100 | 100 | 100 | 100 | 100 | 100 | 100 | 100 | 100 | 99 |
|  | 1 | POST | 100 | 100 | 100 | 100 | 100 | 100 | 100 | 100 | 100 | 100 |
| 124. | 1 | PRE | 85 | 100 | 100 | 100 | 100 | 100 | — | 100 | 100 | 70 |
|  | 1 | POST | 10 | 0 | 100 | 100 | 100 | 35 | 15 | 100 | 35 | 0 |
| 125. | 4 | PRE | 0 | 0 | 100 | 100 | 55 | 95 | 100 | — | 10 | 10 |
|  | 4 | POST | 0 | 0 | 70 | 100 | 0 | 0 | 20 | 0 | 0 | 0 |
| 126. | 1 | PRE | 95 | 100 | — | 100 | 100 | 100 | 100 | 100 | 100 | 100 |
|  | 1 | POST | 65 | 35 | 30 | 100 | 70 | 75 | 100 | 85 | 0 | 0 |
| 128. | 1 | PRE | 100 | 100 | — | 100 | 100 | 100 | 100 | 100 | 98 | 100 |
|  | 1 | POST | 55 | 98 | 100 | 100 | 100 | 100 | 100 | 98 | 75 | 90 |
| 129. | 1 | PRE | 100 | 100 | — | 100 | 100 | 100 | 100 | 100 | 100 | 100 |
|  | 1 | POST | 80 | 100 | 100 | 100 | 100 | 100 | 95 | 65 | 40 | 80 |
| 131. | 1 | PRE | 100 | 100 | — | 100 | 100 | 100 | 100 | 100 | 100 | 95 |
|  | 1 | POST | 25 | 100 | 100 | 100 | 65 | 95 | 30 | 100 | 60 | 0 |
| 132. | 4 | PRE | 80 | 100 | — | 100 | 100 | 100 | 100 | 85 | 98 | 95 |
|  | 4 | POST | 25 | 100 | 100 | 100 | 60 | 85 | 98 | 25 | 0 | 35 |
| 134. | 1 | PRE | 100 | 90 | — | 100 | 100 | 100 | 100 | 65 | 20 | 60 |
|  | 1 | POST | 75 | 50 | 100 | 80 | 100 | 0 | 25 | 15 | 0 | 0 |

TABLE VI-continued

HERBICIDAL ACTIVITY

| Compound No. | Rate (lb./A) | Type | CKL | MG | PIG | VEL | SMT | BYG | FOX | ION | NUT | WO |
|---|---|---|---|---|---|---|---|---|---|---|---|---|
| 136. | 1 | PRE | 35 | 55 | — | 100 | 100 | 100 | 100 | 100 | 30 | 85 |
|  | 1 | POST | 35 | 40 | 100 | 100 | 100 | 0 | 100 | 60 | 0 | 0 |
| 137. | 1 | PRE | 75 | 100 | — | 100 | 100 | 100 | 100 | 100 | 0 | 95 |
|  | 1 | POST | 55 | 70 | 100 | 75 | 100 | 0 | 15 | 10 | 40 | 0 |
| 138. | 1 | PRE | 85 | 100 | — | 100 | 100 | 100 | 100 | 100 | 0 | 95 |
|  | 1 | POST | 70 | 55 | 100 | 100 | 100 | 70 | 98 | 55 | 25 | 0 |

*"—"means not tested

TABLE VII

HERBICIDAL ACTIVITY

| Compound No. | Rate (lb./A) | Type | BID | NS | SMT | VEL | BYG | CRB | FOX | MF |
|---|---|---|---|---|---|---|---|---|---|---|
| 33. | 1 | PRE | 50 | 0 | 100 | 100 | 100 | 95 | 100 | 80 |
|  | 1 | POST | 40 | 100 | 100 | 100 | 95 | 20 | 75 | 20 |
| 52. | 2 | PRE | 100 | — | 100 | 100 | 95 | 100 | 100 | 100 |
|  | 1 | POST | 100 | 100 | 100 | 100 | 40 | 20 | 10 | 0 |
| 93. | 1 | PRE | 100 | 100 | 100 | 100 | 100 | 100 | 100 | 100 |
|  | 1 | POST | 100 | 100 | 100 | 100 | 100 | 100 | 100 | 100 |
| 94. | 1 | PRE | 95 | 40 | 100 | 100 | 0 | 100 | 90 | 0 |
|  | 1 | POST | 40 | 100 | 70 | 100 | 20 | 40 | 25 | 0 |
| 95. | 1 | PRE | 100 | 100 | 100 | 100 | 95 | 100 | 100 | 100 |
|  | 1 | POST | 100 | 100 | 100 | 100 | 95 | 100 | 100 | 95 |
| 121. | 1 | PRE | 100 | — | 100 | 100 | 100 | 100 | 100 | 75 |
|  | 1 | POST | 100 | 100 | 100 | 100 | 75 | 75 | 85 | 20 |
| 123. | 1 | PRE | 100 | 100 | 100 | 100 | 100 | 100 | 100 | 10 |
|  | 1 | POST | 75 | — | 75 | 100 | 20 | 20 | 90 | 0 |
| 127. | 1 | PRE | 100 | 100 | 100 | 100 | 100 | 100 | 100 | 100 |
|  | 1 | POST | 100 | 100 | 100 | 100 | 90 | 20 | 100 | 40 |
| 130. | 1 | PRE | 100 | 100 | 100 | 100 | 100 | 100 | 100 | 100 |
|  | 1 | POST | 100 | 100 | 100 | 100 | 100 | 60 | 100 | 20 |
| 133. | 1 | PRE | 100 | 100 | 100 | 100 | 95 | 100 | 100 | 100 |
|  | 1 | POST | 100 | — | 100 | 100 | 95 | 100 | 100 | 25 |
| 135. | 1 | PRE | 100 | 100 | 100 | 100 | 100 | 100 | 100 | 100 |
|  | 1 | POST | 100 | — | 100 | 100 | 100 | 100 | 100 | 95 |
| 139. | 3 | PRE | 100 | 100 | 100 | 100 | 100 | 100 | 100 | 100 |
|  | 3 | POST | 100 | 100 | 100 | 100 | 100 | 100 | 100 | 100 |
| 140. | 1 | PRE | — | 100 | 100 | 100 | 98 | — | 100 | — |
|  | 1 | POST | — | 100 | 15 | 100 | 100 | — | 70 | — |
| 141. | 1 | PRE | — | 100 | 100 | 100 | 99 | — | 100 | — |
|  | 1 | POST | — | 100 | 100 | 100 | 100 | — | 100 | — |
| 142. | 1 | PRE | 80 | 90 | 100 | 100 | 95 | 100 | 100 | 80 |
|  | 1 | POST | 90 | 100 | 100 | 100 | 25 | 40 | 50 | 0 |
| 143. | 1 | PRE | 100 | 100 | 100 | 100 | 100 | 100 | 100 | 100 |
|  | 1 | POST | 100 | 100 | 100 | 100 | 100 | 100 | 100 | 100 |
| 144. | 1 | PRE | 100 | 100 | 100 | 100 | 100 | 100 | 100 | 100 |
|  | 1 | POST | 95 | 100 | 100 | 100 | 100 | 100 | 100 | 100 |
| 145. | 1 | PRE | 100 | 100 | 100 | 100 | 100 | 100 | 100 | 100 |
|  | 1 | POST | 100 | — | 100 | 100 | 100 | 100 | 100 | 100 |
| 146. | 1 | PRE | 100 | 100 | 100 | — | 100 | — | 100 | 100 |
|  | 1 | POST | 100 | 100 | 100 | 100 | 100 | 100 | 100 | 95 |
| 147. | 1 | PRE | 100 | 100 | — | 100 | 95 | — | 100 | 100 |
|  | 1 | POST | 100 | 100 | 100 | 100 | 98 | 85 | 80 | 70 |
| 148. | 1 | PRE | 90 | 90 | 0 | 100 | 0 | 0 | 0 | 0 |
|  | 1 | POST | 0 | 0 | 0 | 0 | 0 | 0 | 0 | 0 |
| 149. | 1 | PRE | 100 | 100 | 100 | 100 | 100 | 100 | 100 | 100 |
|  | 1 | POST | 100 | 100 | 100 | 100 | 100 | 100 | 100 | 95 |
| 150. | 1 | PRE | 100 | 100 | 100 | 100 | 100 | 100 | 100 | 100 |
|  | 1 | POST | 100 | — | 100 | 100 | 100 | 100 | 100 | 70 |
| 151. | 1 | PRE | 100 | 100 | 100 | 100 | 100 | 100 | 100 | 100 |
|  | 1 | POST | 100 | — | 100 | 100 | 100 | 100 | 100 | 90 |
| 152. | 1 | PRE | 100 | 60 | 80 | 100 | 40 | 0 | 0 | 0 |
|  | 1 | POST | 80 | — | 0 | 100 | 0 | 40 | 20 | 0 |
| 153. | 1 | PRE | 75 | 50 | 100 | 100 | 25 | 80 | 70 | 0 |
|  | 1 | POST | 75 | 80 | 0 | 20 | 10 | 0 | 20 | 0 |
| 154. | 1 | PRE | 100 | 100 | 100 | 100 | 100 | 100 | 100 | 100 |
|  | 1 | POST | 100 | 100 | 100 | 100 | 100 | 100 | 100 | 100 |
| 155. | 1 | PRE | 100 | 100 | 100 | 100 | 100 | 100 | 100 | 100 |
|  | 1 | POST | 100 | 100 | 100 | 100 | 100 | 100 | 100 | 100 |

TABLE VII-continued

HERBICIDAL ACTIVITY

| Compound No. | Rate (lb./A) | Type | BID | NS | SMT | VEL | BYG | CRB | FOX | MF |
|---|---|---|---|---|---|---|---|---|---|---|
| 156. | 1 | PRE | 90 | 100 | 100 | 100 | 0 | 100 | 100 | 90 |
| | 1 | POST | 40 | 100 | 80 | 100 | 10 | 0 | 0 | 30 |
| 157. | 1 | PRE | 100 | 100 | 100 | 100 | 100 | 100 | 100 | 100 |
| | 1 | POST | 100 | 100 | 100 | 100 | 100 | 100 | 90 | 60 |
| 158. | 1 | PRE | 100 | 100 | 100 | 100 | 100 | 100 | 100 | 100 |
| | 1 | POST | 100 | 100 | 100 | 100 | 100 | 100 | 100 | 100 |
| 159. | 1 | PRE | 95 | 100 | 100 | 100 | 10 | 100 | 100 | 10 |
| | 1 | POST | 80 | 100 | 100 | 100 | 10 | 80 | 20 | 10 |
| 160. | 1 | PRE | 100 | 100 | 100 | 100 | 100 | 100 | 100 | 100 |
| | 1 | POST | 100 | 100 | 100 | 100 | 100 | 100 | 100 | 100 |
| 161. | 1 | PRE | 100 | 100 | 100 | 100 | 0 | 95 | 100 | 0 |
| | 1 | POST | 35 | 100 | 100 | 100 | 40 | 80 | 50 | 0 |
| 162. | 1 | PRE | 100 | 100 | 100 | 100 | 50 | 100 | 100 | 95 |
| | 1 | POST | 95 | 100 | 100 | 100 | 100 | 85 | 90 | 60 |
| 163. | 1 | PRE | 100 | 100 | 100 | 100 | 90 | 100 | 100 | 100 |
| | 1 | POST | 100 | 100 | 100 | 100 | 100 | 80 | 90 | 50 |
| 164. | 1 | PRE | 100 | 100 | 100 | 100 | 85 | 95 | 100 | 95 |
| | 1 | POST | 75 | 100 | 100 | 100 | 60 | 80 | 60 | 20 |
| 165. | 1 | PRE | 100 | 100 | 100 | 100 | 100 | 100 | 100 | 100 |
| | 1 | POST | 100 | 100 | 100 | 100 | 100 | 100 | 100 | 100 |
| 166. | 1 | PRE | 100 | 100 | 100 | 100 | 100 | 100 | 100 | 100 |
| | 1 | POST | 100 | 100 | 100 | 100 | 100 | 100 | 100 | 100 |
| 167. | 1 | PRE | 100 | 100 | 100 | 100 | 100 | 100 | 100 | 100 |
| | 1 | POST | 100 | 100 | 100 | 100 | 100 | 95 | 100 | 95 |
| 168. | 1 | PRE | 100 | 100 | 100 | 100 | 100 | 100 | 100 | 100 |
| | 1 | POST | 100 | 100 | 100 | 100 | 100 | 100 | 100 | 100 |
| 169. | 1 | PRE | 100 | 100 | 100 | 100 | 80 | 100 | 100 | 10 |
| | 1 | POST | 75 | 100 | 100 | 100 | 10 | 90 | 25 | 10 |
| 170. | 1 | PRE | 0 | 0 | 0 | 0 | 0 | 0 | 0 | 0 |
| | 1 | POST | 40 | 60 | 0 | 0 | 0 | 0 | 0 | 0 |
| 171. | 1 | PRE | 100 | 100 | 100 | 100 | 100 | 100 | 100 | 100 |
| | 1 | POST | 75 | — | 100 | 100 | 100 | 100 | 100 | 60 |
| 172. | 1 | PRE | 100 | 100 | 100 | 100 | 100 | 100 | 100 | 100 |
| | 1 | POST | 100 | 100 | 100 | 100 | 100 | 100 | 100 | 100 |
| 173. | 1 | PRE | 95 | 100 | 100 | 100 | 80 | 100 | 100 | 50 |
| | 1 | POST | 100 | 100 | 100 | 100 | 100 | 100 | 100 | 50 |
| 174. | 1 | PRE | 85 | 100 | 100 | 100 | 90 | 100 | 100 | 100 |
| | 1 | POST | 100 | 100 | 100 | 100 | 100 | 100 | 100 | 100 |
| 175. | 1 | PRE | 25 | 100 | 100 | 100 | 0 | 100 | 100 | 100 |
| | 1 | POST | 30 | — | 100 | 100 | 60 | 90 | 80 | 75 |
| 176. | 1 | PRE | 95 | 100 | 100 | 100 | 95 | 100 | 100 | 95 |
| | 1 | POST | 95 | — | 100 | 100 | 95 | 100 | 95 | 75 |
| 177. | 1 | PRE | 90 | 100 | 100 | 100 | 95 | 100 | 100 | 40 |
| | 1 | POST | 100 | — | 100 | 100 | 95 | 100 | 100 | 50 |
| 178. | 1 | PRE | 40 | 0 | 100 | 90 | 0 | 100 | 100 | 25 |
| | 1 | POST | 100 | 100 | 100 | 100 | 75 | 60 | 90 | 50 |
| 179. | 1 | PRE | 100 | 100 | 100 | 100 | 100 | 100 | 100 | 100 |
| | 1 | POST | 100 | 100 | 100 | 100 | 100 | 100 | 95 | 100 |
| 180. | 1 | PRE | 10 | 100 | 0 | 95 | 0 | 95 | 95 | 0 |
| | 1 | POST | 75 | 80 | 0 | 40 | 0 | 90 | 40 | 0 |
| 181. | 1 | PRE | 100 | 100 | 100 | 100 | 75 | 100 | 100 | 95 |
| | 1 | POST | 100 | 100 | 100 | 100 | 100 | 100 | 100 | 75 |
| 182. | 1 | PRE | 100 | 100 | 100 | 100 | 100 | 100 | 100 | 100 |
| | 1 | POST | 100 | 100 | 100 | 100 | 100 | 100 | 100 | 100 |
| 183. | 1 | PRE | 0 | 0 | 0 | 0 | 0 | 0 | 0 | 0 |
| | 1 | POST | 10 | 20 | 20 | 0 | 0 | 0 | 0 | 0 |
| 184. | 1 | PRE | 100 | 0 | 100 | 100 | 95 | 100 | 100 | 100 |
| | 1 | POST | 100 | 100 | 100 | 100 | 100 | 100 | 100 | 70 |
| 185. | 1 | PRE | 0 | 0 | 0 | 50 | 0 | 0 | 0 | 0 |
| | 1 | POST | 50 | 75 | 0 | 35 | 0 | 20 | 0 | 0 |
| 186. | 1 | PRE | 95 | 100 | 100 | 100 | 100 | 100 | 100 | 100 |
| | 1 | POST | 100 | 100 | 100 | 100 | 100 | 100 | 100 | 60 |
| 187. | 1 | PRE | 90 | 100 | 100 | 100 | 95 | 100 | 100 | 95 |
| | 1 | POST | 95 | 100 | 100 | 100 | 100 | 100 | 100 | 50 |
| 188. | 1 | PRE | 100 | 100 | 100 | 100 | 100 | 100 | 100 | 100 |
| | 1 | POST | 100 | 100 | 100 | 100 | 100 | 100 | 100 | 100 |
| 189. | 1 | PRE | 100 | 100 | 100 | 100 | 95 | 100 | 100 | 100 |
| | 1 | POST | 95 | 100 | 100 | 100 | 95 | 95 | 100 | 80 |
| 190. | 1 | PRE | 100 | 100 | 100 | 100 | 90 | 100 | 100 | 95 |
| | 1 | POST | 100 | 100 | 95 | 100 | 95 | 100 | 100 | 95 |
| 191. | 1 | PRE | 100 | 50 | 0 | 100 | 0 | 100 | 95 | 25 |
| | 1 | POST | 80 | 95 | 20 | 95 | 20 | 50 | 40 | 0 |
| 192. | 1 | PRE | 100 | 100 | 100 | 100 | 100 | 100 | 100 | 100 |
| | 1 | POST | 100 | 100 | 100 | 100 | 100 | 100 | 100 | 100 |

TABLE VII-continued

HERBICIDAL ACTIVITY

| Compound No. | Rate (lb./A) | Type | BID | NS | SMT | VEL | BYG | CRB | FOX | MF |
|---|---|---|---|---|---|---|---|---|---|---|
| 193. | 1 | PRE | 100 | 100 | 95 | 100 | 95 | 100 | 100 | 95 |
| | 1 | POST | 100 | 100 | 100 | 100 | 95 | 90 | 95 | 75 |
| 194. | 1 | PRE | 95 | 100 | 100 | 100 | 100 | 100 | 100 | 95 |
| | 1 | POST | 100 | 100 | 100 | 100 | 100 | 100 | 100 | 95 |
| 195. | 1 | PRE | 100 | 100 | 100 | 100 | 100 | 100 | 100 | 100 |
| | 1 | POST | 100 | 100 | 100 | 100 | 100 | 100 | 100 | 100 |
| 196. | 1 | PRE | 100 | 100 | — | 100 | 95 | 100 | 100 | 100 |
| | 1 | POST | 100 | 100 | 100 | 100 | 100 | 100 | 100 | 100 |
| 197. | 1 | PRE | 100 | 80 | 100 | 100 | 100 | 100 | 100 | 95 |
| | 1 | POST | 100 | 100 | 100 | 100 | 100 | 95 | 100 | 95 |
| 198. | 1 | PRE | 75 | 90 | 0 | 100 | 0 | 60 | 0 | 0 |
| | 1 | POST | 0 | 0 | 0 | 0 | 0 | 0 | 0 | 0 |
| 199. | 1 | PRE | 100 | 0 | 100 | 100 | 95 | 100 | 100 | 75 |
| | 1 | POST | 100 | 100 | 100 | 100 | 100 | 95 | 100 | 95 |
| 200. | 1 | PRE | 100 | 100 | 100 | 100 | 100 | 100 | 100 | 100 |
| | 1 | POST | 90 | 100 | 100 | 100 | 80 | 50 | 90 | 10 |
| 201. | 1 | PRE | 100 | 100 | 100 | 100 | 100 | 100 | 100 | 100 |
| | 1 | POST | 100 | 100 | 100 | 100 | 100 | 95 | 100 | 100 |
| 202. | 1 | PRE | 50 | 85 | 100 | 100 | 10 | 95 | 100 | 90 |
| | 1 | POST | 20 | 20 | 60 | 20 | 0 | 0 | 0 | 0 |
| 203. | 1 | PRE | 100 | 100 | 100 | 100 | 80 | 100 | 100 | 90 |
| | 1 | POST | 100 | 100 | 100 | 100 | 95 | 95 | 100 | 95 |
| 204. | 1 | PRE | 95 | 100 | 100 | 100 | 95 | 100 | 100 | 100 |
| | 1 | POST | 95 | 100 | 100 | 100 | 80 | 0 | 60 | 50 |
| 205. | 1 | PRE | 90 | 90 | 90 | 100 | 20 | 80 | 95 | 40 |
| | 1 | POST | 10 | 100 | 90 | 50 | 0 | 0 | 0 | 0 |
| 206. | 1 | PRE | 100 | 100 | 100 | 100 | 100 | 100 | 100 | 100 |
| | 1 | POST | 100 | 100 | 100 | 100 | 100 | 100 | 100 | 100 |
| 207. | 1 | PRE | 95 | 100 | 100 | 100 | 95 | 95 | 100 | 100 |
| | 1 | POST | 100 | 100 | 100 | 100 | 100 | 85 | 100 | 95 |
| 208. | 1 | PRE | 100 | 100 | 100 | 100 | 100 | 100 | 100 | 100 |
| | 1 | POST | 100 | 100 | 100 | 100 | 95 | 75 | 100 | 100 |
| 209. | 1 | PRE | 40 | 20 | 100 | 100 | 0 | 95 | 100 | 80 |
| | 1 | POST | 85 | 100 | 95 | 100 | 60 | 60 | 85 | 40 |
| 210. | 1 | PRE | 100 | 100 | 100 | 100 | 95 | 100 | 100 | 100 |
| | 1 | POST | 95 | 100 | 100 | 100 | 95 | 80 | 95 | 90 |
| 211. | 1 | PRE | 100 | 40 | 100 | 100 | 40 | 100 | 100 | 90 |
| | 1 | POST | 90 | 60 | 100 | 95 | 60 | 10 | 40 | 10 |
| 212. | 1 | PRE | 100 | 100 | 100 | 100 | 100 | 100 | 100 | 100 |
| | 1 | POST | 100 | 100 | 100 | 100 | 100 | 100 | 100 | 100 |
| 213. | 1 | PRE | 0 | 0 | 0 | 100 | 0 | 0 | 0 | 0 |
| | 1 | POST | 100 | 100 | 100 | 100 | 100 | 95 | 100 | 75 |
| 214. | 1 | PRE | 0 | 0 | 100 | 0 | 0 | 0 | 0 | 0 |
| | 1 | POST | 0 | 0 | 0 | 0 | 0 | 0 | 0 | 0 |
| 215. | 1 | PRE | 95 | 90 | 100 | 100 | 35 | 90 | 100 | 90 |
| | 1 | POST | 100 | 100 | 100 | 100 | 95 | 100 | 100 | 90 |
| 216. | 1 | PRE | 100 | 100 | 100 | 100 | 100 | 100 | 100 | 100 |
| | 1 | POST | 100 | 100 | 100 | 100 | 100 | 100 | 100 | 100 |
| 217. | 1 | PRE | 100 | 95 | 100 | 100 | 100 | 100 | 100 | 100 |
| | 1 | POST | 100 | 100 | 100 | 100 | 100 | 75 | 100 | 80 |
| 218. | 1 | PRE | 100 | 90 | 100 | 100 | 100 | 100 | 100 | 95 |
| | 1 | POST | 100 | 100 | 100 | 100 | 100 | 100 | 100 | 95 |
| 219. | 1 | PRE | 80 | 70 | 100 | 100 | 95 | 100 | 100 | 50 |
| | 1 | POST | 100 | 100 | 100 | 100 | 95 | 100 | 100 | 70 |
| 220. | 1 | PRE | 80 | 0 | 95 | 100 | 80 | 100 | 100 | 40 |
| | 1 | POST | 100 | 95 | 100 | 100 | 60 | 30 | 100 | 20 |
| 221. | 1 | PRE | 0 | 10 | 100 | 100 | 25 | 80 | 95 | 0 |
| | 1 | POST | 100 | 100 | 100 | 100 | 70 | 95 | 100 | 25 |
| 222. | 1 | PRE | 0 | 0 | 0 | 0 | 0 | 0 | 0 | 0 |
| | 1 | POST | 25 | 80 | 0 | 95 | 0 | 0 | 0 | 0 |
| 223. | 1 | PRE | 70 | 10 | 100 | 100 | 100 | 100 | 100 | 80 |
| | 1 | POST | 100 | 100 | 100 | 100 | 100 | 100 | 100 | 50 |
| 224. | 1 | PRE | 100 | 100 | 100 | 100 | 100 | 100 | 100 | 100 |
| | 1 | POST | 100 | 100 | 100 | 100 | 100 | 100 | 100 | 100 |
| 225. | 1 | PRE | 0 | 0 | 0 | 75 | 0 | 0 | 0 | 0 |
| | 1 | POST | 90 | 100 | 80 | 100 | 0 | 0 | 20 | 0 |
| 226. | 1 | PRE | 70 | 10 | 20 | 75 | 40 | 80 | 100 | 25 |
| | 1 | POST | 90 | 100 | 100 | 90 | 25 | 0 | 60 | 10 |
| 227. | 1 | PRE | 95 | 90 | 80 | 100 | 70 | 100 | 100 | 80 |
| | 1 | POST | 100 | 100 | 100 | 100 | 80 | 100 | 100 | 90 |
| 228. | 1 | PRE | 90 | 95 | 100 | 100 | 95 | 100 | 100 | 100 |
| | 1 | POST | 75 | 100 | 100 | 100 | 95 | 90 | 70 | 70 |
| 229. | 1 | PRE | 95 | 100 | 0 | 95 | 0 | 70 | 90 | 0 |
| | 1 | POST | 80 | 100 | 10 | 100 | 10 | 20 | 25 | 0 |

TABLE VII-continued

HERBICIDAL ACTIVITY

| Compound No. | Rate (lb./A) | Type | BID | NS | SMT | VEL | BYG | CRB | FOX | MF |
|---|---|---|---|---|---|---|---|---|---|---|
| 230. | 1 | PRE | 100 | 100 | 100 | 100 | 100 | 100 | 100 | 100 |
|  | 1 | POST | 100 | 100 | 100 | 100 | 100 | 100 | 100 | 100 |
| 231. | 1 | PRE | 70 | 80 | 90 | 100 | 90 | 100 | 100 | 95 |
|  | 1 | POST | 0 | 0 | 0 | 0 | 0 | 0 | 0 | 0 |
| 232. | 1 | PRE | 85 | 100 | 100 | 100 | 100 | 100 | 100 | 100 |
|  | 1 | POST | 95 | 100 | 100 | 100 | 100 | 75 | 100 | 80 |
| 233. | 1 | PRE | 85 | 100 | 100 | 100 | 100 | 100 | 100 | 100 |
|  | 1 | POST | 40 | 100 | 100 | 95 | 100 | 25 | 90 | 40 |
| 234. | 1 | PRE | 95 | 100 | 100 | 100 | 10 | 90 | 100 | 90 |
|  | 1 | POST | 40 | 100 | 100 | 100 | 0 | 0 | 50 | 0 |
| 235. | 1 | PRE | 100 | — | — | 100 | 95 | 100 | 100 | 100 |
|  | 1 | POST | 95 | 100 | 100 | 100 | 100 | 70 | 95 | 80 |
| 236. | 1 | PRE | 100 | 100 | 100 | 100 | 95 | 100 | 100 | 100 |
|  | 1 | POST | 100 | 100 | 100 | 100 | 85 | 75 | 80 | 20 |
| 237. | 1 | PRE | 100 | 100 | 100 | 100 | 95 | 100 | 100 | 100 |
|  | 1 | POST | 100 | 100 | 100 | 100 | 100 | 100 | 100 | 100 |
| 238. | 1 | PRE | 100 | 100 | 100 | 100 | 100 | 100 | 100 | 100 |
|  | 1 | POST | 100 | 100 | 100 | 100 | 100 | 100 | 100 | 100 |
| 239. | 1 | PRE | 95 | 100 | 100 | 100 | 25 | 100 | 100 | 10 |
|  | 1 | POST | 100 | 100 | 100 | 100 | 60 | 75 | 85 | 0 |
| 240. | 1 | POST | 100 | 100 | 100 | 100 | 100 | 100 | 100 | 100 |
| 241. | 1 | POST | 95 | 100 | 100 | 100 | 95 | 95 | 60 | 95 |
| 242. | 1 | POST | 100 | 100 | 100 | 100 | 100 | 100 | 100 | 95 |
| 243. | 1 | PRE | 100 | 100 | 100 | 100 | 80 | 100 | 90 | 100 |
|  | 1 | POST | 100 | 100 | 100 | 100 | 100 | 95 | 50 | 80 |
| 244. | 1 | PRE | 60 | 95 | 0 | 95 | 40 | 100 | 80 | 85 |
|  | 1 | POST | 70 | 100 | 100 | 100 | 10 | 10 | 35 | 20 |
| 245. | 1 | PRE | 0 | 80 | 0 | 90 | 0 | 95 | 80 | 0 |
|  | 1 | POST | 90 | 100 | 85 | 100 | 10 | 25 | 30 | 0 |
| 246. | 1 | PRE | 60 | 90 | 40 | 100 | 0 | 80 | 20 | 10 |
|  | 1 | POST | 75 | 95 | 95 | 50 | 0 | 0 | 10 | 0 |

*"—"means not tested

The glutarimide compounds of the instant invention are also useful as algicides. The compounds may be advantageously used to either prevent or control the growth of algae. The exact amount of glutarimide required will, of course, vary with the medium being protected, the algae being controlled, the particular glutarimide being employed and other factors known to one skilled in the art.

The glutarimides of the present invention, when used for the control of algae, can be used in any of the types of formulations disclosed above for the control of undesired plants. These formulations include liquid solutions, such as emulsifiable concentrates and dilute sprays, and dry powders such as wettable powders and dusts.

The algicidal and algistatic activities of the compounds of the instant invention were determined by the following procedure.

In separate wells of a microtiter plate (Plate A) were placed 100 μl serial dilutions of the compound to be tested in modified Allen's medium, described below. In addition, one well contained only modified Allen's medium (no compound) as a control. Each well of the plate was then inoculated with a mixed algae culture. After 4 hours, a 5 μl aliquot of each well was removed and placed in a different microtiter plate well (Plate B) containing 100 μl of Allen's modified medium. The plates were covered with clear plastic lids and placed in a clear plastic bag along with several moistened paper towels to create high humidity and prevent evaporation from the plates.

The plastic bags containing the plates were placed in high light conditions (200–700 foot candles) at room temperature. After 5 or 14 days the minimal inhibitory concentration (MIC) needed to inhibit growth was determined from Plate A. The effect of inhibiting growth is defined as the static effect. After 8–10 days, the 4-hour cidal effect (killing of the organism) of the compound was determined from Plate B. To read the microtiter plates for static or cidal activity, a stereoscope was used at low magnification to observe growth or no growth in each well. Plate readers were also used to read growth or no growth.

The following procedure was used to prepare modified Allen's medium.

Seven stock solutions were prepared as follows:

| | |
|---|---|
| $NaNO_3$ | 10.0 g in 400 ml deionized water |
| $CaCl_2$ | 1.0 g in 400 ml deionized water |
| $MgSO_4.7H_2O$ | 3.0 g in 400 ml deionized water |
| $K_2HPO_4$ | 3.0 g in 400 ml deionized water |
| $KH_2PO_4$ | 7.0 g in 400 ml deionized water |
| NaCl | 1.0 g in 400 ml deionized water |
| $FeCl_3$ | 1.0 g in 100 ml deionized water |

Each of the above stock solutions was filter sterilized.

To 940 ml of sterile deionized water, was added 1 drop of the $FeCl_3$ solution and 10.0 ml of all the other stock solutions. The ambient pH of this medium was about 6.1 and the water hardness was about 65 ppm, expressed as calcium carbonate. The pH and hardness was adjusted to the pH value of Table VIII with sterile 1 normal (N) KOH or HCl for pH and the water hardness of Table VIII with a sterile $NaHCO_3$ solution (56.03 g $NaHCO_3$ in 1.0 liter of boiled and distilled water, then filtered and sterilized.

The mixed algae culture was obtained from an industrial cooling tower in Spring House, Pa. and maintained in the laboratory by means commonly known. The mixed culture contained green algae and blue-green bacteria.

The algicidal activity (in ppm) of compounds of the present invention in modified Allen's medium under 750 foot candles of light is shown in Table VIII.

TABLE VIII

| Compound No. | No. of Days | pH 6.1 393 ppm* static | pH 6.1 393 ppm* cidal | pH 8 200 ppm static |
|---|---|---|---|---|
| Test 1  10 | 5 | <0.015 | <2 | —** |
| Test 2  10 | 5 | 0.25 | — | — |
| 85 | 5 | 0.125 | — | — |
| 51 | 5 | 0.25 | — | — |
| Test 3  2 | 14 | | | 32 |
| 12 | 14 | | | 32 |
| 19 | 14 | | | 125 |
| 27 | 14 | | | 125 |
| 34 | 14 | | | 125 |
| 38 | 14 | | | 63 |
| 41 | 14 | | | 63 |
| 45 | 14 | | | <2 |
| 46 | 14 | | | 4 |
| 49 | 14 | | | 32 |
| 56 | 14 | | | 250 |
| 57 | 14 | | | 32 |
| 62 | 14 | | | 63 |
| 64 | 14 | | | 125 |
| 76 | 14 | | | 125 |
| 78 | 14 | | | 250 |
| 80 | 14 | | | 63 |
| 81 | 14 | | | 63 |
| 87 | 14 | | | 125 |
| 91 | 14 | | | 63 |
| 92 | 14 | | | 125 |
| 99 | 14 | | | 250 |
| 110 | 14 | | | 63 |
| 114 | 14 | | | <2 |
| 148 | 14 | | | 125 |

*ppm water hardness, expressed as calcium carbonate
**not tested

It is to be understood that changes and variations may be made without departing from the spirit and scope of the invention as defined by the appended claims.

What is claimed is:

1. A herbicidal compound of the formula

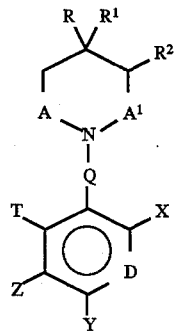

I wherein
A is carbonyl, or thiocarbonyl;
$A^1$ is carbonyl;
D is CH;
Q is $(CH_2)_n$, where n is 0 or 1;
R is $(C_1-C_4)$alkyl, $(C_1-C_4)$haloalkyl containing from one to nine halo atoms, or phenyl;
$R^1$ is hydrogen or $(C_1-C_2)$alkyl;
$R^2$ is hydrogen; or
R, $R^1$ and $R^2$ taken together form a fused phenyl ring; provided $R^1$ is hydrogen when X and Z are independently hydrogen or halogen and Y is halogen;
X is hydrogen, cyano or halogen;
Y is hydrogen, halogen, cyano, $(C_1-C_3)$alkylthio, halo$(C_1-C_3)$alkylthio, $(C_1-C_3)$alkyl, halo$(C_1-C_3)$alkyl, nitro, halo$(C_1-C_3)$alkoxy or $(C_1-C_3)$alkoxy;
provided when Y is hydrogen, R is trifluoromethyl, $R^1$ and $R^2$ are hydrogen and Z is not hydrogen;
T is hydrogen or fluorine; and
Z is formyl; carboxy; alkylcarbonyl; alkoxycarbonyl; (alkylthio)carbonyl; alkoxycarbonylalkoxycarbonyl; phenoxycarbonyl; alkoxyalkoxycarbonyl; alkenyloxycarbonyl; alkynyloxycarbonyl; cycloalkoxycarbonyl; cycloalkylalkoxycarbonyl; (alkenylthio)carbonyl; (alkynylthio)carbonyl; (cycloalkylthio)carbonyl; (cycloalkylalkylthio)carbonyl; heterocyclylalkoxycarbonyl; heterocyclyloxycarbonyl; trialkylsilylalkoxycarbonyl; dialkoxyphosphonylalkoxycarbonyl; dialkyliminooxycarbonyl; alkyliminooxycarbonyl; alkyl(alkoxy)iminooxycarbonyl; alkyl(alkylthio)iminooxycarbonyl; phenylaminocarbonyl; aminocarbonyl; alkylaminocarbonyl; alkenylaminocarbonyl; alkynylaminocarbonyl; alkoxyaminocarbonyl; and the agronomically acceptables salts thereof.

2. The compound of claim 1 wherein
A is C=O, or C=S;
$A^1$ is C=O;
D is CH;
Q is $(CH_2)_n$, where n is 0 or 1;
R is $(C_1-C_4)$alkyl, $(C_1-C_4)$haloalkyl or phenyl;
$R^1$ is H or $(C_1-C_2)$alkyl, provided R1 is H when X and Z are independently hydrogen or halogen and Y is halogen;
$R^2$ is H or, together with R and $R^1$, fused phenyl;
X is H, Cl, Br, CN or F;
Y is H, Cl, Br, F, I, $CH_3$, $SCH_3$, nitro, or $OCH_3$;
provided when Y is hydrogen, R is trifluoromethyl, $R^1$ and $R^2$ are hydrogen and Z is not hydrogen;
T is H or F;
Z is $(C_1-C_6)$alkylcarbonyl; $(C_1-C_6)$alkoxycarbonyl; $((C_1-C_6)$alkylthio)carbonyl; $(C_1-C_6)$alkoxycarbonyl$(C_1-C_6)$alkoxycarbonyl; cyano$(C_1-C_6)$alkoxycarbonyl; $(C_1-C_6)$alkoxy$(C_1-C_6)$alkoxycarbonyl; $(C_1-C_6)$alkenyloxycarbonyl; $(C_1-C_6)$alkynyloxycarbonyl; $(C_1-C_6)$cycloalkyloxycarbonyl; heterocyclyloxycarbonyl; tri$(C_1-C_6)$alkylsilyl$(C_1-C_6)$alkoxycarbonyl; di$(C_1-C_6)$alkoxyphosphonyl$(C_1-C_6)$alkoxycarbonyl; di$(C_1-C_6)$alkyliminooxycarbonyl; mono$(C_1-C_6)$alkylaminocarbonyl; mono$(C_1-C_6)$alkynylaminocarbonyl; phenylaminocarbonyl; mono$(C_1-C_6)$alkoxyaminocarbonyl; and the agronomically acceptable salts thereof.

3. The compound of claim 2 wherein
A is C=O;
$A^1$ is C=O;
D is CH;
Q is $(CH_2)$n, where n is 0 or 1;
R is $(C_1-C_4)$alkyl, $(C_1-C_4)$haloalkyl or phenyl;
$R^1$ is H or $(C_1-C_2)$alkyl;
$R^2$ is H or, together with R and $R^1$, fused phenyl;
X is H, Cl, Br or F;
Y is H, Cl, Br, F or $CH_3$;
T is H or F;
Z is carboxy; formyl; $(C_1-C_6)$alkoxycarbonyl$(C_1-C_6)$alkoxycarbonyl $(C_1-C_6)$alkoxycarbonyl; cyano ($C_1$–$C_6$)alkoxycarbonyl; $C_1$–$C_6$)alkoxy ($C_1$–$C_6$) alkoxycarbonyl; (($C_1$–$C_6$)alkylthio)carbonyl; ($C_1$–$C_6$) alkylcarbonyl; ($C_3$–$C_6$)alkenyloxycarbonyl; halo ($C_3$–$C_6$)alkenyloxycarbonyl; ($C_1$–$C_6$) alkynyloxycarbonyl; ($C_1$–$C_6$)cycloalkoxycarbonyl; heterocylyloxycarbonyl; tri($C_1$–$C_6$)alkylsilyl($C_1$–$C_6$) alkoxycarbonyl; di($C_1$–$C_6$)alkyliminooxycarbonyl; monoalkylaminocarbonyl; monoalkoxyaminocarbonyl; mono($C_1$–$C_6$)alkynylaminocarbonyl; or phenylaminocarbonyl; and the agronomically acceptable salts thereof.

4. The compound of claim 3 wherein A and A1 are C=O; D is CH; Q is $(CH_2)_n$; n is 0; R is $CH_3$, $CHF_2$ or CF3; $R^1$ is H; $R^2$ is H; X is Cl or F; Y is Br, F, or Cl; T is H; and Z is, ($C_1$–$C_6$)alkoxycarbonyl, ($C_1$–$C_6$)cycloalkoxycarbonyl; ($C_3$–$C_6$)alkenyloxycarbonyl or ($C_3$–$C_6$) alkynyloxycarbonyl; and the agronomically acceptable salts thereof.

5. The compound of claim 4 wherein R is $CF_3$, $R^1$ and $R^2$ are hydrogen, X is fluoro, Y is chloro and Z is carboxy, methoxycarbonyl, n-propyloxycarbonyl, isopropyloxycarbonyl, s-butyloxycarbonyl, cyclobutyloxycarbonyl or ethoxycarbonyl and the agronomically acceptable salts thereof.

6. The compound of claim 4 wherein R is $CH_3$, $R^1$ and $R^2$ are hydrogen, X is fluoro, Y is chloro, and Z is isopropyloxycarbonyl.

7. The compound of claim 4 wherein R is $CF_3$, $R^1$ and $R^2$ are hydrogen, X is fluoro, Y is bromo, and Z is isopropyloxycarbonyl.

8. The compound of claim 4 wherein R is $CHF_2$, $R^1$ and $R^2$ are hydrogen, X is fluoro, Y is chloro, and Z is isopropyloxycarbonyl.

9. A method for controlling unwanted plants which comprises applying to the plant or growth medium therefore the compound of claim 1.

10. A method for controlling unwanted plants which comprises applying to the plant or growth medium therefore the compound of claim 2.

11. A method for controlling unwanted plants which comprises applying to the plant or growth medium therefore the compound of claim 3.

12. A method for controlling unwanted plants which comprises applying to the plant or growth medium therefore the compound of claim 4.

13. A method for controlling unwanted plants which comprises applying to the plant or growth medium therefore the compound of claim 5.

14. A method for controlling unwanted plants which comprises applying to the plant or growth medium therefore the compound of claim 6.

15. A method for controlling unwanted plants which comprises applying to the plant or growth medium therefore the compound of claim 7.

16. A method for controlling unwanted plants which comprises applying to the plant or growth medium therefore the compound of claim 8.

17. The method of claim 9 wherein the compound is applied at a rate of from about 0.0001 to about 12 pounds per acre.

18. The method of claim 9 wherein the compound is applied preemergence.

19. The method of claim 9 wherein the compound is applied postemergence.

20. A method for inhibiting the growth of algae in a locus subject to contamination by algae which comprises incorporating onto or into the locus, in an amount effective to adversely affect the growth of algae, the compound of claim 1.

* * * * *